US009212155B2

(12) United States Patent
Pesyan et al.

(10) Patent No.: US 9,212,155 B2
(45) Date of Patent: *Dec. 15, 2015

(54) COMPOUNDS ADVANTAGEOUS IN THE TREATMENT OF CENTRAL NERVOUS SYSTEM DISEASES AND DISORDERS

(75) Inventors: Amir Pesyan, Park City, UT (US); Manuel F. Balandrin, Sandy, UT (US)

(73) Assignee: AURIMMED PHARMA, INC., Salt Lake City, UT (US)

(*) Notice: Subject to any disclaimer, the term of this patent is extended or adjusted under 35 U.S.C. 154(b) by 89 days.

This patent is subject to a terminal disclaimer.

(21) Appl. No.: 12/881,068

(22) Filed: Sep. 13, 2010

(65) Prior Publication Data
US 2011/0046128 A1 Feb. 24, 2011

Related U.S. Application Data

(63) Continuation-in-part of application No. 12/922,068, filed as application No. PCT/US2009/037558 on Mar. 18, 2009.

(60) Provisional application No. 61/243,110, filed on Sep. 16, 2009, provisional application No. 61/334,356, filed on May 13, 2010, provisional application No. 61/037,987, filed on Mar. 19, 2008.

(51) Int. Cl.
| | | |
|---|---|---|
| A61K 31/165 | (2006.01) |
| C07C 233/11 | (2006.01) |
| C07D 295/155 | (2006.01) |
| A61K 31/353 | (2006.01) |
| A61K 31/36 | (2006.01) |
| A61K 31/44 | (2006.01) |
| A61K 31/445 | (2006.01) |
| A61K 31/495 | (2006.01) |
| A61K 31/5375 | (2006.01) |
| A61K 45/06 | (2006.01) |

(52) U.S. Cl.
CPC .......... *C07D 295/155* (2013.01); *A61K 31/165* (2013.01); *A61K 31/353* (2013.01); *A61K 31/36* (2013.01); *A61K 31/44* (2013.01); *A61K 31/445* (2013.01); *A61K 31/495* (2013.01); *A61K 31/5375* (2013.01); *A61K 45/06* (2013.01)

(58) Field of Classification Search
CPC .............................. A61K 31/165; C07C 233/11
USPC .............. 564/347, 374, 155, 167, 175, 182; 514/553, 557, 613, 625, 231.2, 617, 514/522, 622
See application file for complete search history.

(56) References Cited

U.S. PATENT DOCUMENTS

| | | | |
|---|---|---|---|
| 4,537,773 A | 8/1985 | Shenvi | |
| 5,169,841 A | 12/1992 | Kleeman et al. | |
| 5,187,157 A | 2/1993 | Kettner et al. | |
| 5,463,125 A | 10/1995 | Sandoval | |
| 5,502,079 A | 3/1996 | Dostert et al. | |
| 5,506,268 A | 4/1996 | Balandrin et al. | |
| 6,255,528 B1 * | 7/2001 | Muller et al. | 564/347 |
| 6,589,994 B1 | 7/2003 | Artman | |
| 6,617,358 B1 | 9/2003 | Balandrin | |
| 6,617,638 B2 * | 9/2003 | Chiang et al. | 257/316 |
| 7,265,155 B2 | 9/2007 | Artman | |
| 8,228,139 B2 | 7/2012 | Lindmark | |
| 2001/0041700 A1 | 11/2001 | Bekkali | |
| 2004/0209858 A1 | 10/2004 | Bennani et al. | |
| 2006/0025477 A1 * | 2/2006 | Artman et al. | 514/553 |
| 2006/0287397 A1 | 12/2006 | Meza Toledo | |

FOREIGN PATENT DOCUMENTS

| | | |
|---|---|---|
| CA | 2718723 | 9/2009 |
| CN | 102164488 | 8/2011 |
| EP | 1787981 | 5/2007 |
| EP | 2268140 | 1/2011 |
| GB | 1445283 | 8/1976 |
| JP | 50049262 | 5/1975 |
| JP | 2001342179 | 12/2001 |
| JP | 2001342180 | 12/2001 |
| JP | 2001342183 | 12/2001 |
| JP | 2003506364 | 2/2003 |
| JP | 2003160549 | 6/2003 |
| JP | 2011529022 | 12/2011 |

(Continued)

OTHER PUBLICATIONS

Muller et al. "Process and . . . " CA134:71393 (2001).*
Muller et al. "Process and" CA134:71393 (2001).*
Improper Markush "Examination guidelines" p. 1,64-67 (2011).*
WHO "classification of mental and b. . . " p. 1-268 (1993.*
U.S. Appl. No. 12/992,068, filed Nov. 10, 2010, Pesyan et al.
International Search Report and Written Opinion from PCT/US2010/048764 dated Oct. 29, 2010.
International Search Report and Written Opinion from PCT/US2009/037558 dated Jan. 12, 2010.
Chemcats RN 771529-83-0 (2012).
U.S. Appl. No. 12/922,068, Dec. 3, 2013, Office Action.
U.S. Appl. No. 12/922,068, Aug. 6, 2013, Final Office Action.

(Continued)

*Primary Examiner* — Celia Chang
(74) *Attorney, Agent, or Firm* — Workman Nydegger

(57) ABSTRACT

A series of novel compounds showing anticonvulsant, chemical countermeasure(s), and analgesic activities is described. Such pharmaceutically active compounds may also show utility in the treatment of other central nervous system ("CNS") diseases and disorders, such as anxiety, depression, insomnia, migraine headaches, schizophrenia, Parkinson's disease, spasticity, Alzheimer's disease, and bipolar disorder. Furthermore, such compounds may additionally find utility as analgesics (e.g., for the treatment of chronic or neuropathic pain) and as neuroprotective agents useful in the treatment of stroke(s), chronic neurodegenerative diseases (such as Alzheimer's disease and Huntington's disease), and/or traumatic brain and/or spinal cord injuries. Moreover, these/such compounds may also be useful in the treatment of status epilepticus and/or as chemical countermeasures.

5 Claims, 25 Drawing Sheets

(56) References Cited

FOREIGN PATENT DOCUMENTS

| | | |
|---|---|---|
| KR | 20110025734 | 3/2011 |
| MX | 2011009035 | 9/2011 |
| SG | 188916 | 4/2013 |
| WO | 9509364 | 4/1995 |
| WO | 9941229 | 8/1999 |
| WO | WO03037274 | 5/2003 |
| WO | 03091201 | 11/2003 |
| WO | 2005085182 | 9/2005 |
| WO | 2005094531 | 10/2005 |
| WO | WO2006008193 | 1/2006 |
| WO | WO2006008194 | 1/2006 |
| WO | 2006012603 | 2/2006 |
| WO | 2007025144 | 3/2007 |
| WO | WO2007060164 | 5/2007 |
| WO | WO2007/141009 | * 12/2007 |
| WO | 2009117515 | 9/2009 |
| WO | 2011034849 | 3/2011 |

OTHER PUBLICATIONS

Satoshi et al. Rhodium(I), catalyzed assymmetric 1 4-addition or arylboronic acids. . . . The Journal of Organic Chemistry, 2001, vol. 66, p. 8944-8946.
Bellrau et al. A new route to the allenolic acid type of compound. Journal of the American Chemical Society, 1951, vol. 73, p. 5443-5444.
Behrens, O. K. et al. "Biosynthesis of Penicillins. III. Preparations and Evaluation of Precursors for New Penicillins," Journal of Biological Chemistry, The American Society of Biological Chemists, Inc. U.S. vol. 175, Jan. 1, 1948, pp. 771-792.
Boggs, "Pain Drugs Have Different Heart Risks", Reuters Health, Jul. 16, 2007.
Brauer et al. "Novel P,N Ligands Derived from R- and S-1-Phenylethylamine with (2R,5R)-2, 5-Dimethylphospholanyl Groups (DuPHAMIN) for Asymmetric Catalysis" Eur. J. Inorg. Chem. 2003, pp. 1748-1755.
Brunton et al., "Goodman and Gilman's: The Pharmacological Basis of Therapeutics" Eleventh Edition, 2006.
Bunlaksananusorn et al. "New P,N Ligands for Asymmetric Ir-Catalyzed Reactions," Angewandte Chemie, Int. Ed. Engl. 2003, 42, p. 3941.
Dichter et al. "New Antiepileptic Drugs; Drug Therapy", The New England Journal of Medicine, Jun. 13, 1996, vol. 34, No. 24 pp. 1583-1590.
Dr. Duke's Phytochemical and Ethnobotanical Databases [Agricultural Research Service, USDA], http://wlivw.ars-grin.gov/duke/index.html (2015).
Drury, et al. "Synthesis of Versatile Chiral N,P Ligands Derived from Pyridine and Quinoline," Angew. Chem., Int. Ed. Engl. 2004, 43, pp. 70-74.
Eby et al. "Rapid Recovery from Major Depression Using Magnesium Treatment", Medical Hyptheses [ Elsevier ] 67(2): 362-370 (2006).
Emrich et al. "The Use of Sodium Valproate, Carbamazepine and Oxcarbazepine in Patients with Affective Disorders," Journal of Affective Disorders, 1985, vol. 8, pp. 243-250.
Farkough et al. "Cardiovasucalr Outcomes in High Risk Patients with Osteoarthritis Treated with Ibuprofen, Naproxen or Lumiracoxib," Annals of the Rheumatic Diseases, 2007, 66:764-770.
Fox, "Painkiller Naproxen Safe for Heart", Reuters Nov. 14, 2006.
Fox, "Popular Painkiller May Pose Heart Danger", Reuters, Nov. 17, 2006.
Goldberg et al., "Racial Background and Lidocaine Pharmacokinetics", J. Clin. Pharmacol. 22 ( Aug.- Sep. 8-9,): 391-394 (1982).
Hering et al. "Sodium Valporate in the Prophylactic Treatment of Migraine: A Double-Bilnd Study Versus Placebo," Cephalagia 12: 81-84 (1992).
Hering et al. "Sodium Valporate in the Treatment of Cluster Headache: an Open Clinical Trial," Cephalalgia, 9:195-198 (1989).
Hoffer A., "Vitamin B-3:Niacin and Its Amide", Townsend Letter for Doctors and Patients, 147:3039, 1995.
Hou et al. "Enantioselective Hydrogenations of Arylalkenes Mediated by [Ir(cod)(JM-Phos)]+Complexes," Chem. Eur. J (2001), vol. 7, No. 24, pp. 5391-5400.
"Ibuprofen May Affect Heart in High-Risk Patients," Reuters, Apr. 2007.
Kallstrom et al. "Rationally Designed Ligands for Asymmetric Iridium-Catalyzed Hydrogenation of Olefins," Journal of the American Chemical Society, 2004, 126, 14308-14309.
Kohl, et al. "The NMDA Recept Complex: A Promising Target for Novel Antiepileptic Strategies," Current Medicinal Chemistry, 2001, pp. 1275-1289.
Kong et al., "Effects of Taurine on Rate Behaviors in Three Anxiety Models", Pharmacology, Biochemistry, and Behavior 83(2): 271-276 (2006).
Matthew et al. "Valporate in the Treatment of Persistent Chronic Daily Headache: An Open Label Study," Headache, 31:71-74 (1991).
Menges et al. "Synthesis and Application of Chiral Phosphino-Imidazoline Ligands: Ir-Catalyzed Enantioselective Hydrogenation," Organic Letters, 2002, 4:26, pp. 4713-4716.
Mohler et al. "Nicotinamide is a Brain Constituent with Benzodiazepine-like Actions", Nature 278: 563-565 (1979).
Nelson et al., :A Pharmacological Study of Some New Synthetic Hypnotics, Journal of the American Pharmaceutical Association, Sci. Ed. (1941) 30:180-182.
O'Keefe, "Restless Legs Syndrome," Arch. Intern. Med., 156:243-248 (1996).
Pfaltz et al. "Iridium-Catalyzed Enantioselective Hydrogenation of Olefins," Adv. Synth. Catal. 2003, 345, pp. 33-43.
"Pozen Confirms FDA Issues Second Approvable Letter for Trexima", Reuters, Aug. 2, 2007.
Prousky J.E., "Niacinamide's Potential Role in Alleviating Anxiety with its Benzodiazepine-like Properties: A Case Report", J. Orthomolec. Med. 19(2): 104-110 (2004).
Ryabukhin et al. "One-Pot Synthesis of β-Imidazolylpropionamides," Tetrahedron Letters, vol. 49, 2008, pp. 3997-4002.
Sachdev et al. "Restlessness: The Anatomy of a Neuropsychiatric Symptom," Australian and New Zealand Journal of Psychiatry, (1996), 30:38-53.
Specter et al., "Diphenhydramine in Orientals and Caucasians", Clin. Pharmacol. Therap. 48(Jul. 1): 10-17 (1990).
Sun et al. "Rh-Catalyzed Highly Enantioselective Synthesis of 3-Arylbutanoic Acids," Angewandte Chemie International Education 2007, 46, 2623-2626.
Swerdlow, "Anticonvulsant Drugs and Chronic Pain," Clinical Neuropharmacology, vol. 7, No. 1 pp. 51-82 (1984).
Tang et al. "Phospholane-Oxazoline Ligands for Ir-Catalyzed Asymmetric Hydrogenation," Angew. Chem., Int. Ed. 2003, 42(8), pp. 943-946.
USDA's Phytochemical and Ethno Botanical Databases (2015).
Volwiler, et al. Some Alkyl and Aryl Amides and Ureides as Hypnotics, Journal of the American Chemical Society, (1936) 58:1352-1354.
Werbach M.R., "Anxiety and the Vitamin B Complex", Townsend Letter for Doctors and Patients, Issue 255, pp. 164-163, 2004.
White et al., "Discovery and preclinical development of antiepileptic drugs," in Antiepileptic Drugs, 5th ed. (2002).
Xu, et al. "Asymmetric Hydrogenation of Aromatic Olefins Catalyzed by Iridium Complexesof Proline Derived Phosphine-Oxazoline Ligands," Tetrahedron Letters, 2003, 44, 953.
http://en.wikipedia.org/wiki/glycine (2015).
http://en.wikipedia.org/wiki/taurine (2015).
International Search Report for PCT/US94/11280 dated Jan. 10, 1995.
International Search Report for PCT/US2009/037558 dated Jan. 12, 2010.
Office Action of U.S. Appl. No. 12/922, 068, mailed Jul. 10, 2014.
Notice of Allowance of U.S. Appl. No. 12/922,068, mailed Mar. 12, 2015.

* cited by examiner

1. ED$_{50}$ < 100 mg/kg:

2. ED$_{50}$ < 300 mg/kg:

3. No activity or motor impairment:

4. No activity, but with minimal motor impairment:

Scheme 1:

Ref.: *Synth. Commun.* 31(5): 679–684 (2001).

Scheme 2:

Scheme 3:

Ref.: Gharpure *et al.*, *J. Chem. Soc., Perkin Trans. 1*, 1990(10): 2759-2761.

Scheme 4:

Ref.: Trenkle *et al.*, *Organometallics* 25(15): 3548-3551 (2006).

Scheme 5:

Ref.: Davis *et al.*, *Synthesis* 2004(12): 1959-1962.

Scheme 6:

HOBT.H$_2$O = 1-Hydroxybenzotriazole hydrate
EDC.HCl = 1-(3-Dimethylaminopropyl)-3-ethylcarbodiimide hydrochloride

Scheme 7:

Ref.: Tang et al., Angew. Chem., Intl. Ed. 42(8): 943-946 (2003).

Scheme 8:

Ref.: Hiller et al., Org. Lett. 6(4): 573-576 (2004).

Scheme 9:

Ref.: Oisaki et al., J. Am. Chem. Soc. 128(22): 7164-7165 (2006).

Scheme 10:

Scheme 11:

Ref.: Concellon *et al.*, *J. Org. Chem.* 71(12): 4428-4432 (2006).

Scheme 12:

Ref.: Concellon *et al.*, *J. Org. Chem.* 71(12): 4428-4432 (2006).

Scheme 13:

Scheme 14:

Ref.: * Shu et al., Synth. Commun. 29(4): 567-572 (1999).

Scheme 15:

COMPOUNDS ADVANTAGEOUS IN THE TREATMENT OF CENTRAL NERVOUS SYSTEM DISEASES AND DISORDERS

RELATED APPLICATIONS

This application claims the benefit of and priority to U.S. Provisional Patent Application Ser. No. 61/243,110 filed 16 Sep. 2009 entitled "NOVEL COMPOUNDS ADVANTAGEOUS IN THE TREATMENT OF CENTRAL NERVOUS SYSTEM DISEASES AND DISORDERS" and U.S. Provisional Patent Application Ser. No. 61/334,356 filed 13 May 2010 entitled "NOVEL COMPOUNDS ADVANTAGEOUS IN THE TREATMENT OF CENTRAL NERVOUS SYSTEM DISEASES AND DISORDERS." This application is also a continuation-in-part of U.S. patent application Ser. No. 12/922,068 filed 10 Sep. 2010 entitled "NOVEL COMPOUNDS ADVANTAGEOUS IN THE TREATMENT OF CENTRAL NERVOUS SYSTEM DISEASES AND DISORDERS," which claims the benefit of and priority to PCT Application Serial No. PCT/US09/37558 filed 18 Mar. 2009 entitled "NOVEL COMPOUNDS ADVANTAGEOUS IN THE TREATMENT OF CENTRAL NERVOUS SYSTEM DISEASES AND DISORDERS" and U.S. Provisional Patent Application Ser. No. 61/037,987 filed 19 Mar. 2008 "NOVEL COMPOUNDS ADVANTAGEOUS IN THE TREATMENT OF CENTRAL NERVOUS SYSTEM DISEASES AND DISORDERS." The above listed applications are incorporated by reference in their entirety.

BACKGROUND OF THE INVENTION

1. The Field of the Invention

The present invention relates to novel compounds showing activity in the central nervous systems (CNS). More specifically, the present invention relates to novel compounds with anticonvulsant activity that exhibit increased/improved toxicological safety (i.e., decreased toxicity), increased/improved metabolic stability, longer half-life, and/or a superior side effect profile, while producing similar or increased biological activity (i.e., efficacy), when compared to currently available CNS therapeutic agents.

2. The Related Technology

A number of pathological conditions (e.g., epilepsy, stroke, bipolar affective disorder, migraine headaches, anxiety, depression, insomnia, schizophrenia, chronic or neuropathic pain, spasticity, spinal cord injury, and chronic neurodegenerative disorders), and diseases (e.g., Parkinson's disease, Huntington's disease, and Alzheimer's disease) are characterized by abnormalities in the normal function of the central nervous system (CNS). These conditions and diseases typically respond to pharmacologic intervention with compounds or substances that modulate CNS activity. Compounds with this activity include the compounds of the present invention, which are herein disclosed to treat abnormalities of the CNS, such as epilepsy. While currently available therapeutants often have good CNS activity, they frequently exhibit other undesirable properties, such as chronic toxicity, severe and/or unpleasant side effects, and inadequate pharmacokinetic properties, such as a short pharmacologic half-life. For example, a short half-life in a CNS therapeutant may require its frequent administration in order to sustain therapeutic concentrations of the drug without eliciting adverse effects, and where frequent dosing schedules are required, the cost of therapy may increase. In addition, as the required dosing frequency increases, patient compliance tends to decrease. It would therefore be desirable to provide additional compounds that modulate CNS activity and have improved properties, such as, e.g., an increased half-life, increased activity (i.e., improved efficacy), and/or increased metabolic stability (e.g., fewer toxic metabolites) when compared to those of currently available therapies. Furthermore, improved and simpler/simplified synthetic and chemical manufacturing processes can be developed which can help to make the useful compounds of the invention more widely available to a larger portion of the patient population.

Related art may be found in U.S. Pat. No. 5,463,125 (Sandoval et al., "Phenyl alcohol amides having anticonvulsant activity"), WO9941229 [Carvajal Sandoval et al., "Halogenated phenyl alcohol amides (ligands of GABAB receptor) having an anticonvulsant activity"], WO03091201 (Carvajal Sandoval et al., "DL-Hydroxy-alkyl-phenylamides having anticonvulsive activity"), WO2005085182 (Meza Toledo, "DL-Hydroxybenzamides having anticonvulsive activity"), and U.S. Patent Application 20060287397 (Meza Toledo, "Dl-Hydroxy-alkyl-phenylamides having anticonvulsive activity"). An important distinction between the art cited above and that of the present invention is that the cited art contains and refers to compounds which are structurally related to gamma-hydroxybutyric acid (gamma-hydroxybutyrate, or GHB), whereas the compounds of the present invention are structurally related to 3-methylbutyramide.

It is noteworthy that the derivatization (N-alkylation) of the nitrogen atom of amide groups has produced compounds such as N,N-diethylisovaleramide (A. Liebrecht, German Patent 129,967, issued 1902), which has been marketed previously as a sedative ("Valyl") (see various editions of *The Merck Index*). However, this compound has been shown instead to exhibit CNS-stimulating, anxiogenic, and convulsant properties (U.S. Pat. No. 5,506,268). Indeed, N-methylated amide derivatives can show either CNS-stimulating or -depressing properties, whereas N-ethyl and larger derivatives generally possess CNS-stimulating properties [Volwiler, E. H. and D. L. Tabern, *J. Am. Chem. Soc.* (1936) 58:1352-1354; Nelson et al., *J. Am. Pharm. Assoc., Sci. Ed.* (1941) 30:180-182].

Thus, N,N-disubstituted amide compounds such as cropropamide, crotethamide, ethamivan, nikethamide, N,N-diethylisovaleramide (U.S. Pat. No. 5,506,268), and the insect repellent, DEET (N,N-diethyl-m-toluamide), have all been shown to exhibit CNS-(proconvulsant-) and respiratory-stimulating properties in mammals (including humans). Cropropamide, crotethamide, ethamivan, and niketamide have been used as CNS and respiratory stimulants in humans, e.g., to counteract the potentially life-threatening CNS- and respiratory-depressing effects of barbiturate poisoning (overdose) (various editions of *The Merck Index* and W. O. Foye's *Principles of Medicinal Chemistry*).

It is also noteworthy that the primary amide, modafinil (ProVigil) has been shown to possess CNS-stimulant and pro-alertness (pro-vigilance) properties [see the current (14th) edition of *The Merck Index*].

BRIEF SUMMARY

A series of novel amides with anticonvulsant, chemical countermeasure(s), and analgesic activities are herein disclosed. These amides modulate CNS activity, by enhancing inhibitory, or decreasing excitatory, neurotransmission centrally, without complete suppression of all activity. Pursuant to the present invention, therefore, a subject who receives such an agent is not overtly sedated, anesthetized, or paralyzed in the context of, for example, decreasing seizures (no anesthesia), decreasing muscle tone (no paralysis), eliciting a calmative effect (no sedation), or ameliorating an ambulatory syndrome such as spasticity (no weakness or flaccidity).

Many of the amides disclosed herein have a phenyl group attached to the amide moiety via a short and variously branched/substituted aliphatic linker. Other compounds of the invention are amide derivatives of optically active amino acids (e.g., D or L), such as alanine, valine, leucine, isoleucine, or phenylalanine, or the optically inactive amino acids, glycine or taurine.

In one embodiment, a CNS-active compound having Formula I is disclosed.

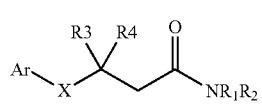

FORMULA I

In Formula I, Ar can be an optionally substituted phenyl, optionally substituted naphthyl, optionally substituted tetrahydronaphthyl, optionally substituted indane, or an optionally substituted heterocyclic aryl, wherein up to 5 substituents may be present. Each substituent on Ar can be independently selected from the group consisting of alkyl, cycloalkyl, halogen, alkoxy, thioalkyl, sulfoxyalkyl, sulfonylalkyl, alkylene dioxy, haloalkyl, haloalkoxy, OH, $CH_2OH$, $CONH_2$, CN, acetoxy, $N(alkyl)_2$, benzyl, benzyloxy, α,α-dimethylbenzyl, $NO_2$, CHO, $CH_3CH(OH)$, acetyl, $OCH_2COOH$, and combinations thereof. Also, the Ar can include an optionally substituted aromatic ring system attached to one or two atoms of the Ar, such aromatic rings being selected from the group consisting of phenyl, phenoxy, heterocyclic aryl, and combinations thereof. The Ar and/or substituent thereon can have up to 5 substituents, and each substituent can be independently selected from the group consisting of alkyl, cycloalkyl, halogen, alkoxy, thioalkyl, sulfoxyalkyl, sulfonylalkyl, alkylene dioxy, haloalkyl, haloalkoxy, OH, $CH_2OH$, $CONH_2$, CN, acetoxy, $N(alkyl)_2$, $NO_2$, CHO, $CH_3CH(OH)$, acetyl, and $OCH_2COOH$. Optionally, the Ar and/or aromatic rings can include bifunctional substituents that form a ring with the Ar and/or aromatic rings, wherein the bifunctional substituents are an optionally substituted alkyl, cylcoalkyl, methylenedioxy, ethylenedioxy, or other alkylenedioxy, and combinations thereof.

In Formula I, $R_1$ and $R_2$ can each be independently at least one of H, long- or short-chain substituted or unsubstituted alkyl, substituted or unsubstituted cycloalkyl, $CW_2$phenyl, or combinations thereof. Each W is independently selected from the group consisting of H, methyl and ethyl (except that both Ws cannot be ethyl). Up to 5 substituents may be present in the phenyl group, and each substituent is independently selected from the group consisting of halogen, alkoxy, thioalkyl, sulfoxyalkyl, sulfonylalkyl, haloalkyl, haloalkoxy, $CONH_2$, CN, acetoxy, $N(alkyl)_2$, $NO_2$, and acetyl.

In another embodiment, when $R_1$ is H, $R_2$ can be $(CH_2)_2SO_3H$ or CHZCOOH, wherein Z is one of the group consisting of H, $CH_3$, $CH(CH_3)_2$, $CH_2C_6H_5$, $CH_2CH(CH_3)_2$, and $CH(CH_3)CH_2CH_3$. Such compounds are amide derivatives of optically inactive amino acid (taurine and glycine) or optically active amino acids (alanine, valine, phenylalanine, leucine, isoleucine). Optionally, $R_1$ and $R_2$ together are cycloalkyl.

In Formula I, $R_3$ is either hydroxy, substituted or unsubstituted alkyl, substituted or unsubstituted cycloalkyl, or together with $R_4$ cycloalkyl, or together with Ar forms an additional aliphatic ring, with the proviso that when $R_3$ is OH, then $R_4$ is not an ethyl.

In Formula I, $R_4$ is one of a substituted or unsubstituted alkyl, substituted or unsubstituted cycloalkyl, or together with $R_3$ cycloalkyl.

In Formula I, X is one of nothing, substituted or unsubstituted alkylene, methylene, ketone, CHOH, oxygen, $NR_1$, sulfur, sulfone, or sulfoxide.

In another embodiment, a CNS-active compound having Formula II is disclosed.

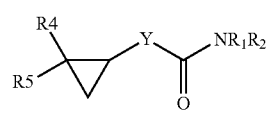

FORMULA II

In Formula II, $R_1$ and $R_2$ are each independently at least one of H, long- or short-chain substituted or unsubstituted alkyl, substituted or unsubstituted, cycloalkyl, $CW_2$phenyl, or combinations thereof. W is independently selected from the group consisting of H, methyl and ethyl, except that both Ws cannot be ethyl. Up to 5 substituents may be present in the phenyl group or cylcoalkyl group, and each substituent is independently selected from the group consisting of halogen, alkoxy, thioalkyl, sulfoxyalkyl, sulfonylalkyl, haloalkyl, haloalkoxy, $CONH_2$, CN, acetoxy, $N(alkyl)_2$, $NO_2$, and acetyl. Optionally, when $R_1$ is H, $R_2$ can be $(CH_2)_2SO_3H$, or CHZCOOH, wherein Z is one of the group consisting of H, $CH_3$, $CH(CH_3)_2$, $CH_2C_6H_5$, $CH_2CH(CH_3)_2$, and $CH(CH_3)CH_2CH_3$. In another option, or $R_1$ and $R_2$ together are cycloalkyl.

$R_4$ can be H, or $R_4$ and $R_5$ are each independently either optionally substituted phenyl or optionally substituted heterocyclic aryl, wherein up to 5 substituents may be present and each substituent is independently selected from the group consisting of halogen, alkoxy, thioalkyl, sulfoxyalkyl, sulfonylalkyl, haloalkyl, haloalkoxy, $CH_2OH$, $CONH_2$, CN, acetoxy, $N(alkyl)_2$, $NO_2$, acetyl, and $OCH_2COOH$.

Y is either nothing, substituted or unsubstituted methylene, or other substituted or unsubstituted alkylene.

In yet another embodiment, the present invention includes a CNS-active compound having one of Formulas 1-9 (shown below).

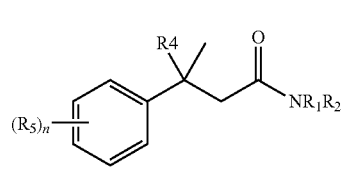

Formula 1

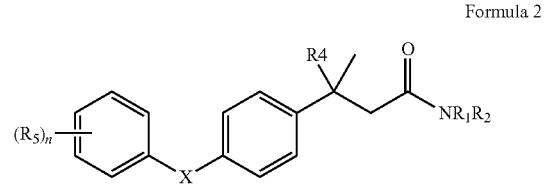

Formula 2

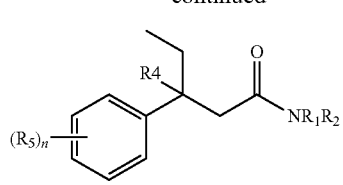

Formula 3

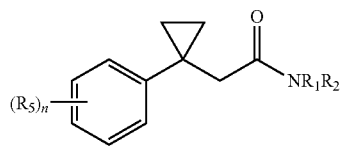

Formula 4

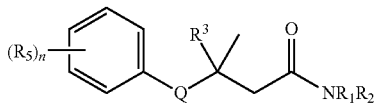

Formula 5

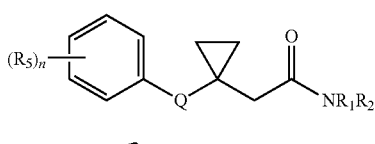

Formula 6

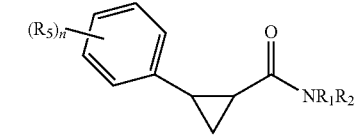

Formula 7

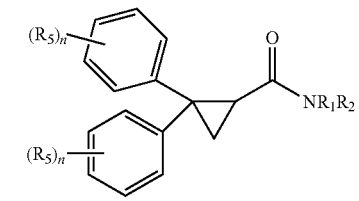

Formula 8

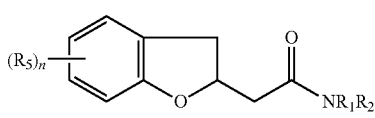

Formula 9

In one embodiment of Formulas 1-9, $R_1$ and $R_2$ are each independently at least one of H, long- or short-chain substituted or unsubstituted alkyl, substituted or unsubstituted, cycloalkyl, $CW_2$phenyl, or combinations thereof. W is independently selected from the group consisting of H, methyl and ethyl, except that both Ws cannot be ethyl. Up to 5 substituents may be present in the phenyl group or cylcoalkyl group, and each substituent is independently selected from the group consisting of halogen, alkoxy, thioalkyl, sulfoxyalkyl, sulfonylalkyl, haloalkyl, haloalkoxy, $CONH_2$, CN, acetoxy, $N(alkyl)_2$, $NO_2$, and acetyl. Optionally, when $R_1$ is H, $R_2$ can be $(CH_2)_2SO_3H$, or CHZCOOH, wherein Z is one of the group consisting of: H, $CH_3$, $CH(CH_3)_2$, $CH_2C_6H_5$, $CH_2CH(CH_3)_2$, and $CH(CH_3)CH_2CH_3$. In another option, $R_1$ and $R_2$ together are cycloalkyl.

In another embodiment of Formulas 1-9, when $R_1$ is H, $R_2$ can be $(CH_2)_2SO_3H$, or CHZCOOH, wherein Z is one of the group consisting of: H, $CH_3$, $CH(CH_3)_2$, $CH_2C_6H_5$, $CH_2CH(CH_3)_2$, and $CH(CH_3)CH_2CH_3$. Optionally, $R_1$ and $R_2$ together are cycloalkyl; $R_3$ is one of either H, hydroxy, substituted or unsubstituted alkyl, substituted or unsubstituted cycloalkyl, or together with the phenyl ring in Formula 5, form an additional aliphatic ring; $R_4$ is one of an H, OH, substituted or unsubstituted alkoxy, substituted or unsubstituted alkyl, substituted or unsubstituted cycloalkyl, or together with the adjacent phenyl ring form an additional aliphatic ring, with the proviso that $R_4$ cannot be OH in Formula 3; $R_5$ is one of H, Cl, F, $CF_3$, CN, C1-C5 alkyl, C1-C5 alkoxy, $OCF_3$, $CONR_1R_2$, halogen-substituted alkyl, halogen-substituted alkoxy; X is one of nothing, substituted or unsubstituted alkylene, methylene, ketone, CHOH, oxygen, $NR_1$, sulfur, sulfone, or sulfoxide; and n can be from 0-5, more preferably from 1-3, and most preferably from 1 to 2.

In yet another embodiment, any of Formulas 1-9 can be characterized as follows: $R_1$ is one of H, $CH_3$, $C_2H_5$, $(CH_2)_2SO_3H$, or CHZCOOH, wherein Z is one of the group consisting of: H, $CH_3$, $CH(CH_3)_2$, $CH_2C_6H_5$, $CH_2CH(CH_3)_2$, and $CH(CH_3)CH_2CH_3$, combination thereof, or derivative thereof; $R_2$, $R_3$, and $R_4$ are independently one of H, $CH_3$, substituted or unsubstituted alkyl, OH (with the proviso that $R_4$ cannot be OH in Formula 3), $OCH_3$, substituted or unsubstituted alkoxy, combination thereof, or derivative thereof; $R_5$ is one of H, Cl, F, $CF_3$, CN, C1-C5 substituted or unsubstituted alkyl, C1-C5 substituted or unsubstituted alkoxy, $OCF_3CONR_1R_2$, combination thereof, and derivative thereof; n=1-5, preferably 1-3; and X=O, $NR_1$, nothing, C=O, S, $SO_2$, combination thereof, and/or derivative thereof.

In yet another embodiment, any of Formulas 1-9 can be characterized as follows: $R_1$ is one of H, $CH_3$, $C_2H_5$, $(CH_2)_2SO_3H$, or CHZCOOH, wherein Z is one of the group consisting of: H, $CH_3$, $CH(CH_3)_2$, $CH_2C_6H_5$, $CH_2CH(CH_3)_2$, and $CH(CH_3)CH_2CH_3$; $R_2$ and $R_3$ are independently one of H or $CH_3$; $R_4$ is one of H, $CH_3$, OH (with the proviso that $R_4$ cannot be OH in Formula 3), or $OCH_3$; $R_5$ is one of H, Cl, F, $CF_3$, CN, C1-C5 alkyl, C1-C5 alkoxy, $OCF_3CONR_1R_2$; n=1-5; Q is one of O, $NR_2$, C=O, S, SO, or $SO_2$; and X=O, $NR_2$, nothing, C=O, S, or $SO_2$.

In a preferred embodiment, a CNS-active compound has the Formula 1 above, where $R_1$ and $R_2$ are H, $R_4$ is either H or $CH_3$, n=1, and $R_5$ is one of $CH_3$, $OCH_3$, $C_1$, $CF_3$ or $OCF_3$ in either the ortho (2'-), meta (3'-), or para (4'-) position on the phenyl ring; in other preferred embodiments, the compounds just described have either an R or S configuration when $R_4$ is H.

In another preferred embodiment, a CNS-active compound has the Formula 1 above, where $R_1$ and $R_2$ are H, $R_4$ is either H or $CH_3$, n=1, and $R_5$ is one of $C_1$, $CF_3$ or $OCF_3$ in either the ortho (2'-), meta (3'-), or para (4'-) position on the phenyl ring; in other preferred embodiments, the compounds just described have either an R or S configuration when $R_4$ is H.

In yet another preferred embodiment, a CNS-active compound has the Formula 1 above, where $R_1$ and $R_2$ are H, $R_4$ is either H or $CH_3$, n=1, and $R_5$ is one of $C_1$, $CF_3$ or $OCF_3$ in either the meta (3'-), or para (4'-) position on the phenyl ring; in other preferred embodiments, the compounds just described have either an R or S configuration when $R_4$ is H.

In a more preferred embodiment, a CNS-active compound has the Formula 1 above, where $R_1$ and $R_2$ are H, $R_4$ is either H or $CH_3$, n=1, and $R_5$ is one of $C_1$, $CF_3$ or $OCF_3$ in the para (4'-) position on the phenyl ring; in other more preferred embodiments, the compounds just described have either an R or S configuration when $R_4$ is H.

In another more preferred embodiment, a CNS-active compound has the Formula 1 above, where $R_1$, $R_2$, and $R_4$ are H, n=1, and $R_5$ is either $CF_3$ or $OCF_3$ in either the meta (3'-) or para (4'-) position on the phenyl ring; in other more preferred embodiments, the compounds just described have either an R or S configuration.

In a most preferred embodiment, a CNS-active compound has the Formula 1 above, where $R_1$, $R_2$, and $R_4$ are H, n=1, and $R_5$ is $OCF_3$ in the para (4'-) position on the phenyl ring; in other most preferred embodiments, the compound just described has either an R or S configuration.

Any one of the compounds described above or a combination of the compounds described above can be included in a pharmaceutical composition. In one embodiment, the pharmaceutical composition includes a therapeutically effective amount of at least one of the compounds described above blended with at least one of a pharmaceutically acceptable carrier or an excipient.

In one embodiment, the therapeutically effective amount is effective for at least one of the following: (a) to provide anticonvulsant activity to a subject, (b) to treat and/or prevent convulsions in a subject, (c) to treat and/or prevent seizures in a subject, (d) to treat and/or prevent spasticity in a subject, (e) to treat and/or prevent affective mood disorders in a subject, (f) to treat and/or prevent bipolar mood disorder in a subject, (g) to treat and/or prevent chronic headaches in a subject, (h) to treat and/or prevent cluster headaches in a subject, (i) to treat and/or prevent migraine headaches in a subject, (j) to treat and/or prevent restlessness syndromes in a subject, (k) to treat and/or prevent neuropathic pain in a subject, or (l) to treat and/or prevent movement disorders in a subject.

In still yet another embodiment, the present invention includes a CNS-active compound of Formula BX or Formula BY or a combination thereof.

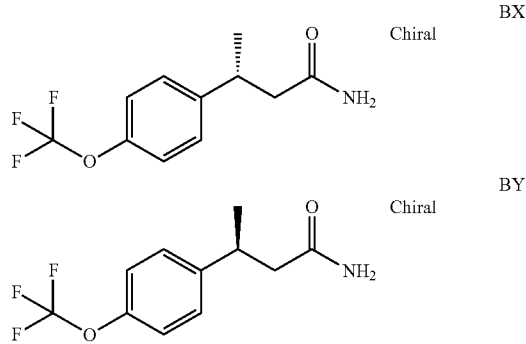

In one embodiment, the compound of Formula BX or BY can be included in a pharmaceutical composition. The pharmaceutical composition includes a therapeutically effective amount of at least one compound of Formula BX or BY blended with at least one of a pharmaceutically acceptable carrier or an excipient.

In one embodiment, the CNS-active compound is present in a therapeutically effective amount to modulate CNS activity. In another embodiment, the effective amount is effective for at least one of the following: (a) to provide anticonvulsant activity to a subject, (b) to treat and/or prevent convulsions in a subject, (c) to treat and/or prevent seizures in a subject, (d) to treat and/or prevent spasticity in a subject, (e) to treat and/or prevent affective mood disorders in a subject, (f) to treat and/or prevent bipolar mood disorder in a subject, (g) to treat and/or prevent chronic headaches in a subject, (h) to treat and/or prevent cluster headaches in a subject, (i) to treat and/or prevent migraine headaches in a subject, (j) to treat and/or prevent restlessness syndromes in a subject, (k) to treat and/or prevent neuropathic pain in a subject, or (l) to treat and/or prevent movement disorders in a subject.

In one embodiment, the compound of Formula BX or Formula BY is BX.

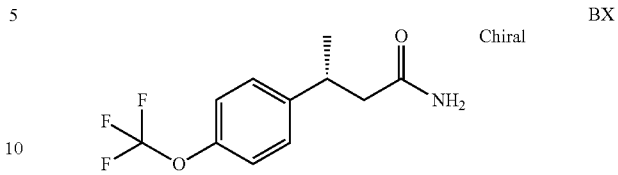

In one embodiment, the compound of Formula BX is active for at least one of the following: (a) to provide anticonvulsant activity to a subject, (b) to treat and/or prevent convulsions in a subject, (c) to treat and/or prevent seizures in a subject, or (d) to treat and/or prevent migraine headaches in a subject.

Any one of the compounds described above or a combination of the compounds described above can be included as a therapeutic agent in a in a method for modulating CNS activity in a subject. In one embodiment, the therapeutic agent is blended with at least one of the compounds described above blended with at least one of a pharmaceutically acceptable carrier or an excipient.

In addition the functions described above, the therapeutic agent may be sufficient to treat and/or prevent the symptoms of at least one of anxiety, depression, insomnia, migraine headaches, schizophrenia, Parkinson's disease, spasticity, Alzheimer's disease, bipolar disorder, chronic or neuropathic pain, stroke, chronic neurodegenerative diseases, cognitive impairment, attention deficit-hyper activity disorder, Huntington's disease, traumatic brain injury, spinal cord injury, or status epilepticus. In addition, the therapeutic agent may be sufficient for a chemical countermeasure.

In still yet another embodiment, the present invention includes a method for identifying a drug target using at least one of one of the compounds described above or derivatives thereof (e.g., a radiolabeled derivative). It is believed, for example, that owing to the unique mechanisms of action of the compounds described herein that the compounds described in the present application may interact with unique targets. As such, compounds described in the present application may be useful as probes for discovering unique targets for treating one or more of the disorders (e.g., neurological disorders, epilepsy, and the like) described herein.

These and other embodiments and features of the present invention will become more fully apparent from the following description and appended claims, or may be learned by the practice of the invention as set forth hereinafter.

DESCRIPTION OF THE ILLUSTRATED EMBODIMENTS

1. Overview

Figure 1:
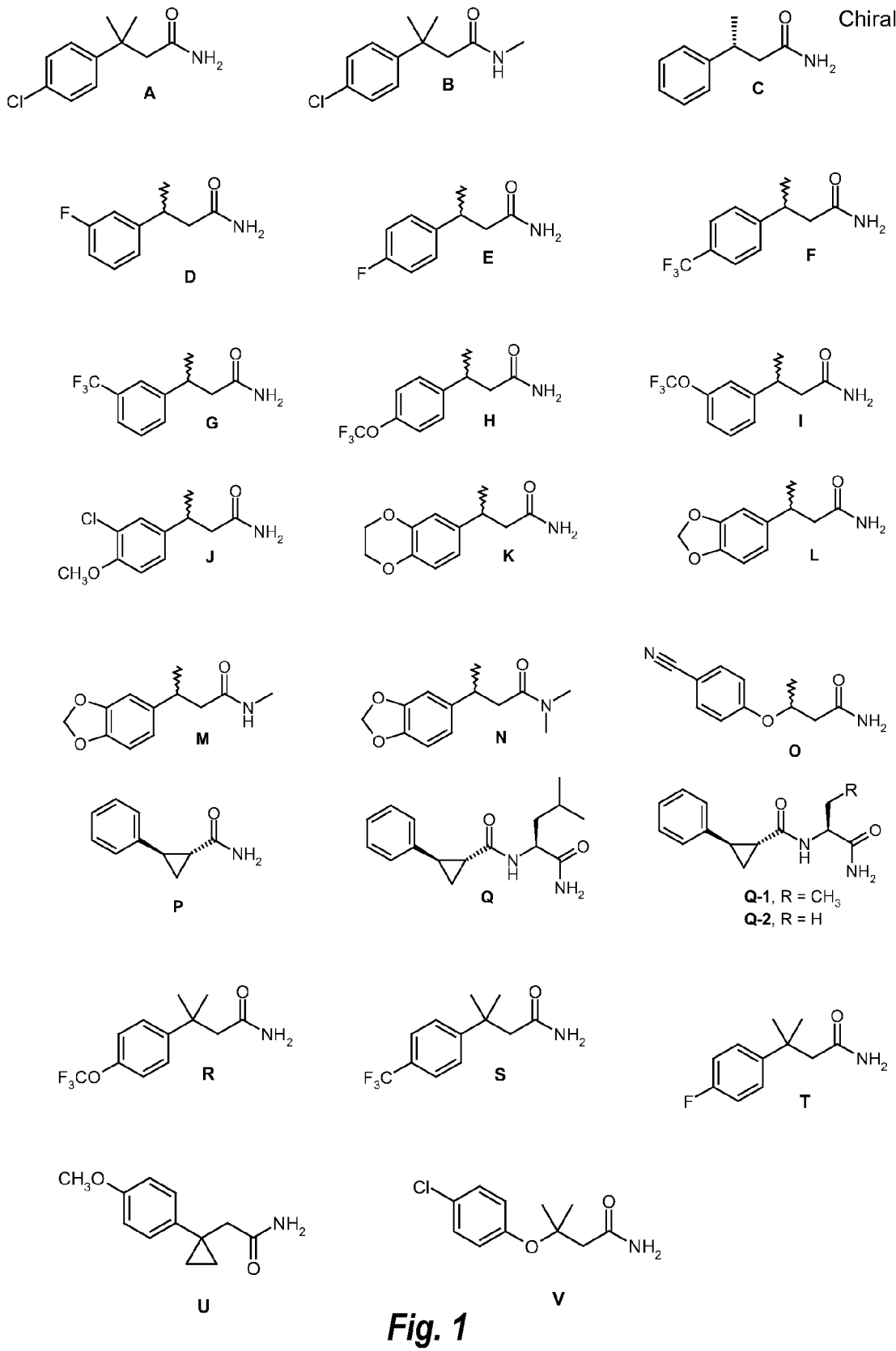
FIG. 1 shows the chemical structures of the novel compounds of the invention that are pharmacologically active in the central nervous systems (CNS) of (for example) mammals, and which exemplify embodiments of the present invention.
Figure 2:
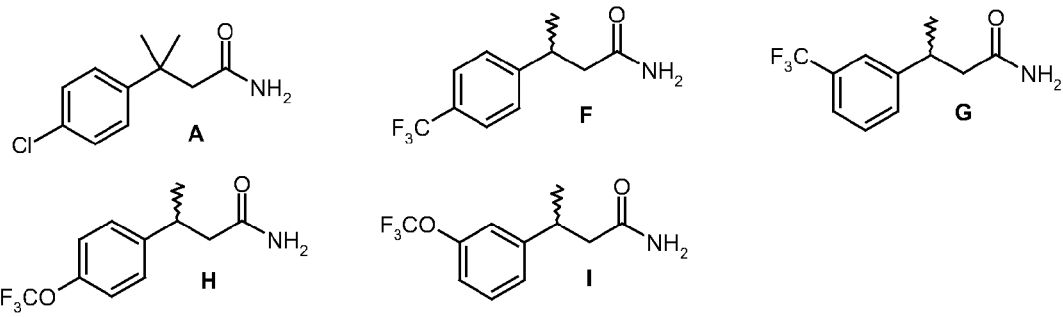
FIG. 2 shows the relative biological activity of the compounds of the invention, specifically showing those compounds which are preferred (second category, $ED_{50} < 300$ mg/kg) and most preferred (first category, $ED_{50} < 100$ mg/kg).
Figure 2:
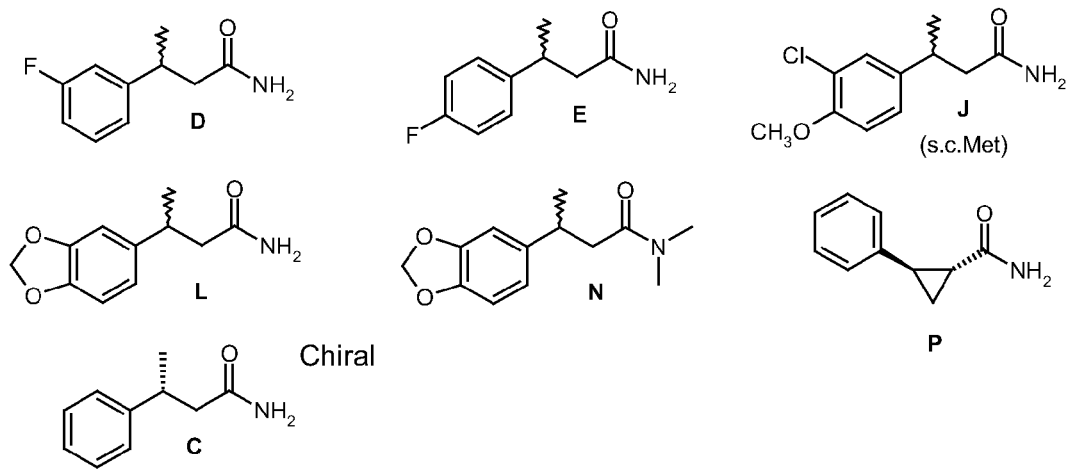
Figure 2:
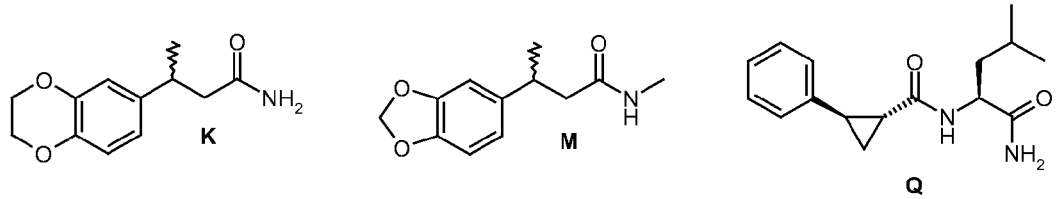
Figure 2:
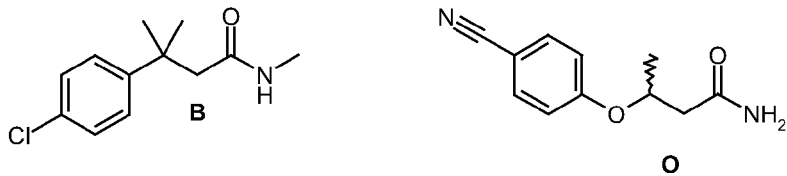
Figure 3A:
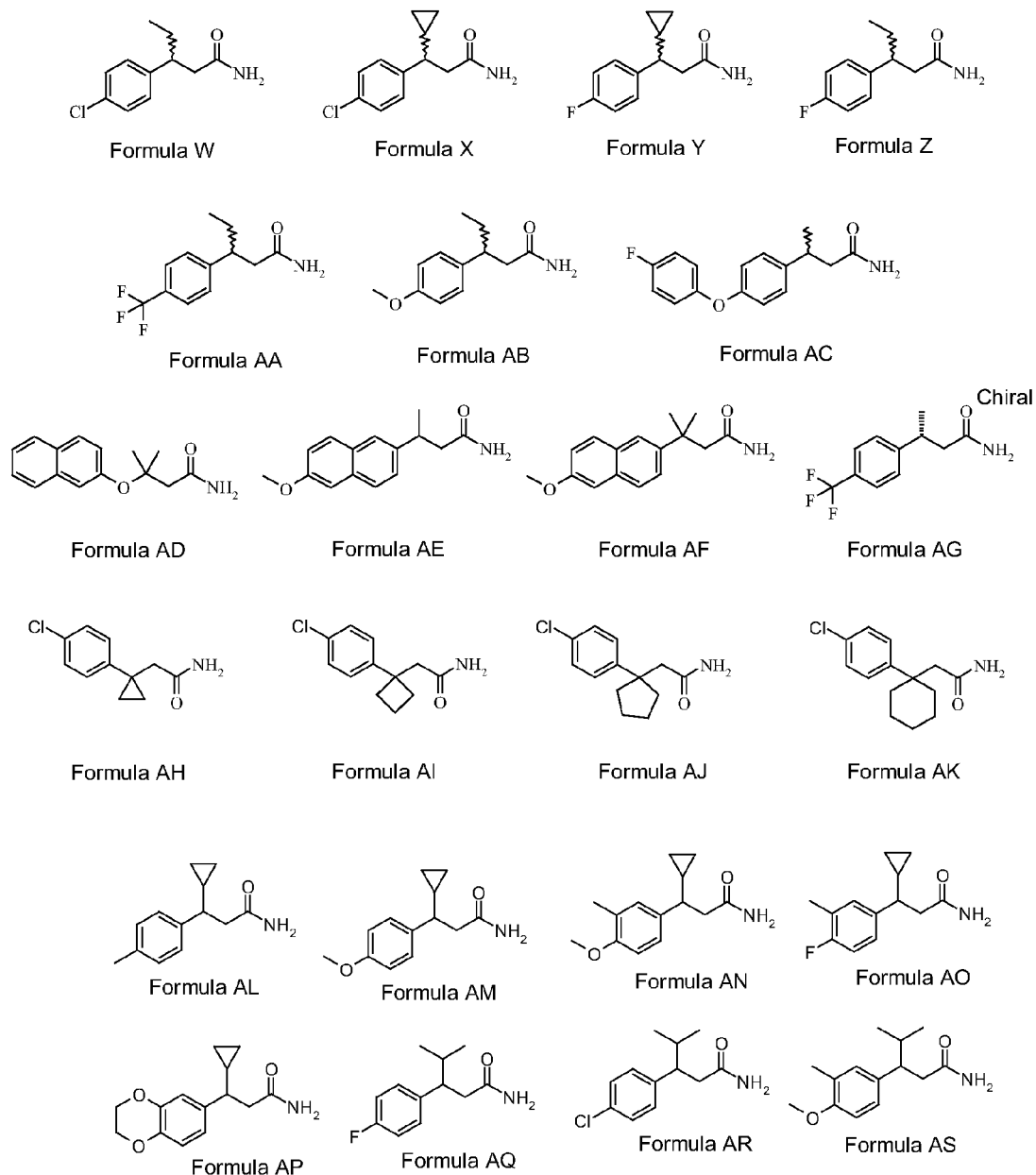
FIG. 3A shows the structures of further compounds of the invention, which are also in the category of most preferred compounds.
Figure 3B:
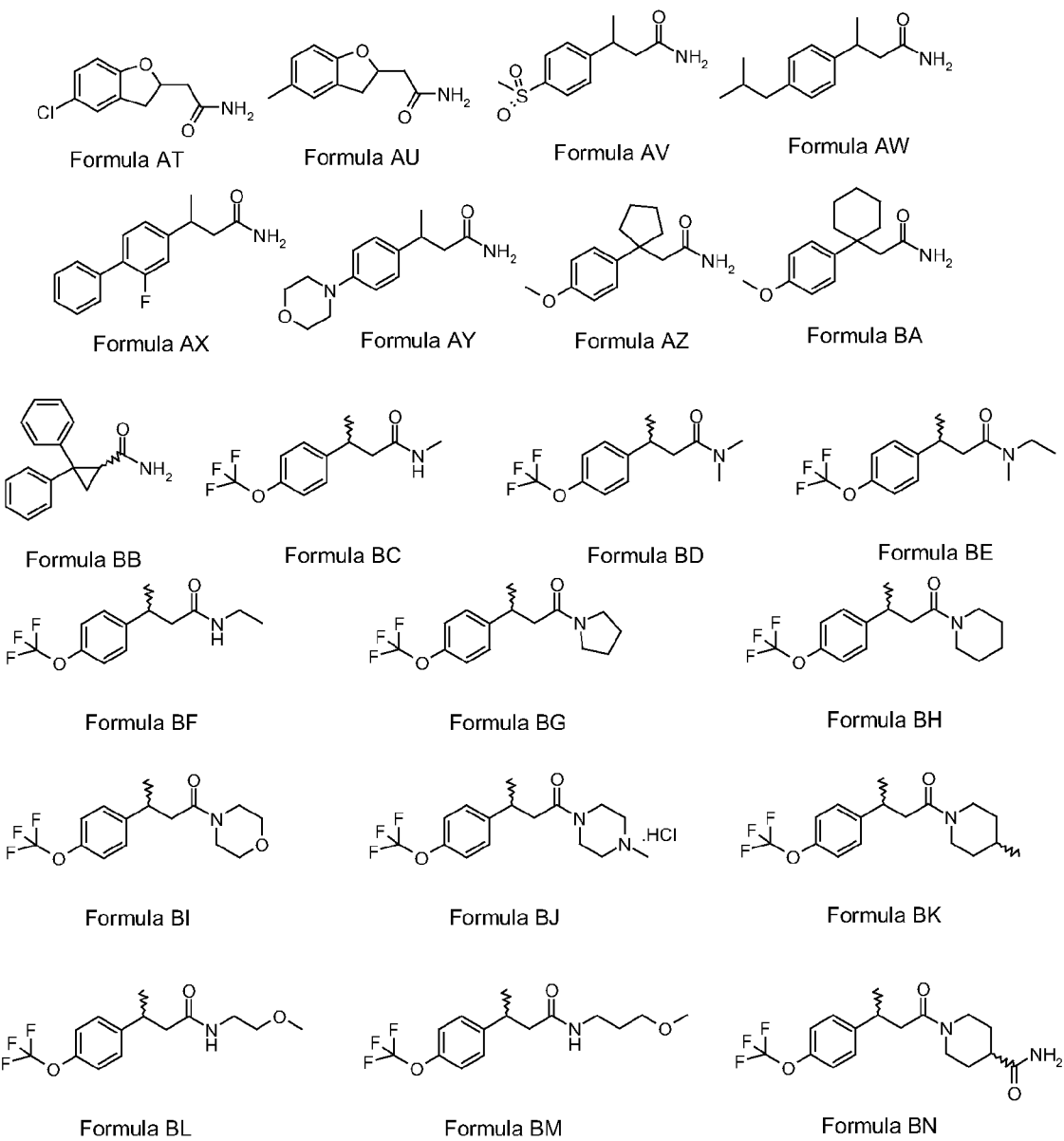
FIG. 3B shows the structures of further compounds of the invention, which are also in the category of most preferred compounds.
Figure 3C:
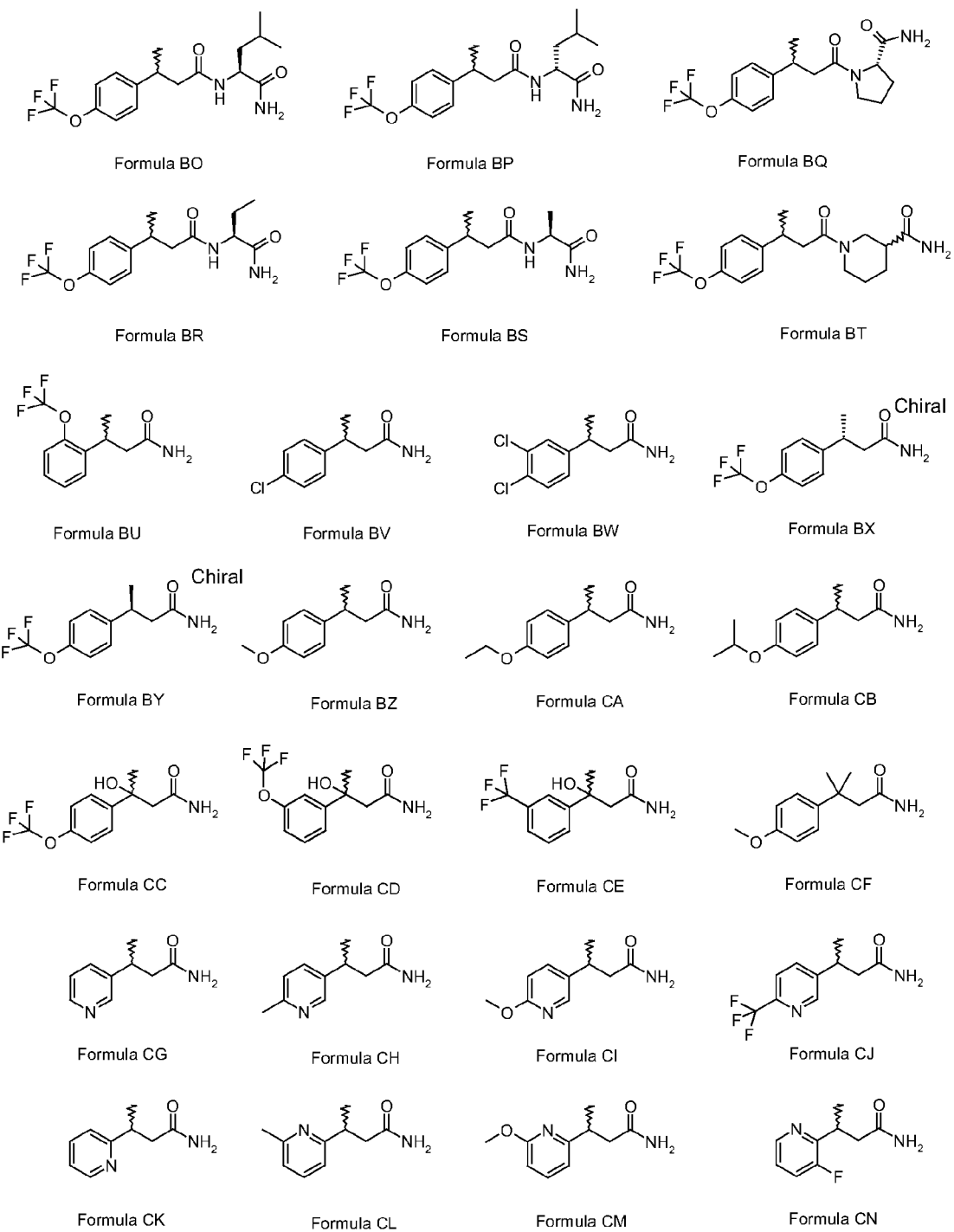
FIG. 3C shows the structures of additional compounds of the invention, which are also in the category of most preferred compounds.
Figure 3D:
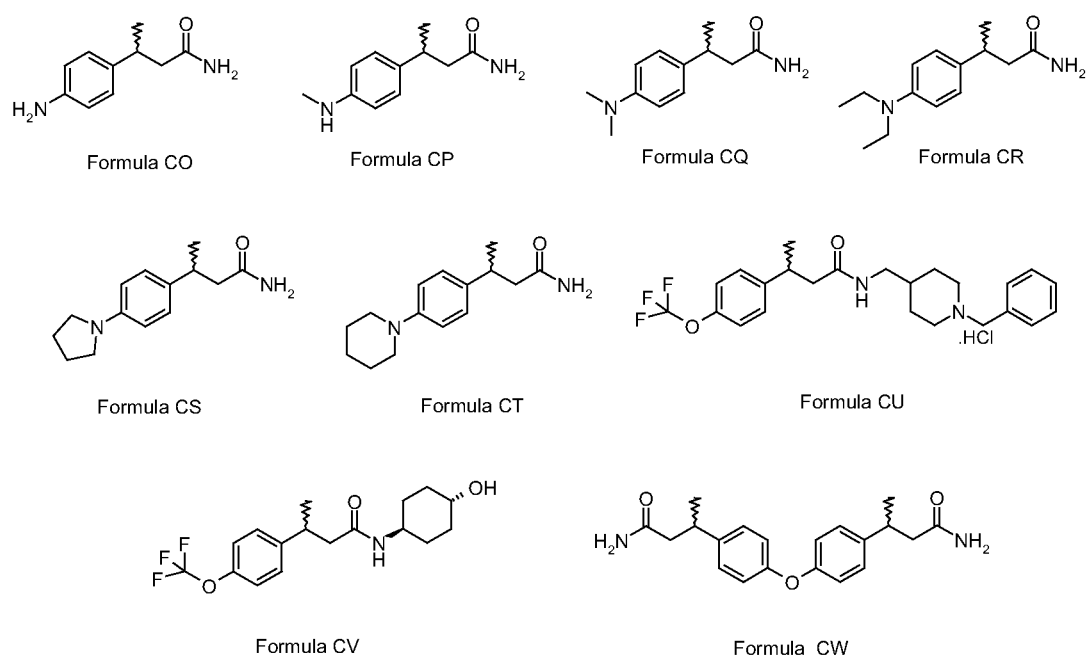
FIG. 3D shows the structures of additional compounds of the invention, which are also in the category of most preferred compounds.

The inventors have discovered that the compounds of the invention and certain of their pharmacologically active analogs and congeners can be administered in vivo to effect a modulation of CNS activity. That is, these agents modulate CNS activity, by enhancing inhibitory, or decreasing excitatory, neurotransmission centrally, without complete suppression of all activity. Pursuant to the present invention, therefore, a subject who receives such an agent is not overtly sedated, anesthetized, or paralyzed in the context of, for example, decreasing seizures (no anesthesia), decreasing muscle tone (no paralysis), eliciting a calmative effect (no sedation), or ameliorating an ambulatory syndrome such as spasticity (no weakness or flaccidity).

A number of pathologies, exemplified by convulsions (seizures), spasticity, affective mood disorders, such as bipolar mood disorder, headaches (chronic, cluster, migraine), restlessness syndromes, neuropathic pain, and movement disorders, have at least one symptom that is alleviated by a modulation of CNS activity. Accordingly, an individual who suffers from such a pathology is a candidate for therapy that entails, pursuant to the present invention, the individuals receiving a pharmaceutical formulation or composition containing the compounds of the invention or one of their structurally related analogs or congeners as one of the principal active ingredients.

2. Exemplary Pathologies Ameliorated by a Modulation of Central Nervous System (CNS) Activity CONVULSIONS: Epilepsy is a common disorder which has many causes, and it can be very difficult to control clinically, often requiring treatment for many years to keep seizures under control. Researchers have stated that "[a]t this time, there is no satisfactory treatment for epilepsy in a substantial proportion of patients. Clinical trials have shown that certain patients have a better response to one drug than another, even when the patients have similar types of seizures and the drugs have similar mechanisms of action. The frequency and severity of side effects also varies substantially. Thus, multiple medications with different mechanisms of action and attendant side effects will be needed for treatment of epilepsy until either epilepsy can be cured or a potent, safe new drug with broad activity is discovered" and developed. Dichter et al., *Drug Therapy* 334:1583 (1996).

Due to the widespread availability of reasonably predictive and experimentally accessible animal models of convulsant states, a number of clinically useful anticonvulsants have been prepared and developed. For example, see Cereghino et al., "Introduction," in ANTIEPILEPTIC DRUGS, 4th ed., pages 1-11 (Rave Press 1995), which states: "In many patients, seizures can be controlled with currently available antiepileptic drugs, but 25 to 30 percent of patients continue to have seizures despite optimal therapy, while many others experience unacceptable side effects." Dichter et al. (1996) supra.

Thus, many anticonvulsants in clinical use are plagued by the occurrence of significant side effects, including troublesome daytime sedation, muscular weakness, tolerance, gingival hyperplasia, and potentially fatal blood dyscrasias and hepatotoxicity. Many of these side effects are especially of concern in the clinical management (treatment) of epilepsy in children.

The present invention can be used to treat convulsive disorders such as epilepsy. That is, the compositions and pharmaceutical formulations and compositions of the invention display "anticonvulsant activity," which is evidenced by a reduction of the severity, number, or duration of convulsions in animal models of epilepsy. To alleviate convulsions includes reducing the severity, number of duration of convulsions in a patient. Accordingly, the novel compositions and pharmaceutical formulations and compositions should be useful in treating conditions such as, but not limited to, generalized tonic-clonic seizures, absence seizures, myoclonic seizures, simple partial seizures, complex partial seizures, secondarily generalized partial seizures, status epilepticus, and trauma-induced seizures, as occur following head injury or surgery.

SPASTICITY: Spasticity is a disorder characterized by an increase in tonic stretch reflexes (muscle tone) with exaggerated tendon jerks resulting from hyperexcitability of the stretch reflex. Lance, Symposia synopsis, in SPASTICITY—DISORDERED MOTOR CONTROL, Feldman et al. (Eds.) (1980). Major disease states and conditions associated with spasticity include multiple sclerosis, cerebral palsy, stroke, trauma or injury to the spinal cord, and head trauma. Symptoms that occur with spasticity include painful flexor and extensor spasms, increased or exaggerated deep-tendon reflexes, clonus, muscular weakness, fatigue, lack of dexterity, various degrees of loss of general motor function, paralysis, and impairment of sleep.

The pathological states observed in spasticity are fundamentally different at the physiological level from the commonly experienced acute muscular aches, strains, and sprains that occur from a localized external insult to a particular muscle, i.e., outside of or peripheral to the CNS. These pathological states also are different from the relatively common involuntary spasms or smooth muscle, such as vascular spasms, bladder spasms, and bronchial spasms. Such non-spastic (non-CNS), peripheral or localized symptoms are commonly treated with so-called "antispasmodic" or "spasmolytic" agents, but these generally are not useful in treating spasticity. Cedarbaum & Schleifer, "Drugs for Parkinson's Disease, Spasticity and Acute Muscle Spasms," in GOODMAN AND GILMAN'S THE PHARMACOLOGICAL BASIS OF THERAPEUTICS, 8th ed. [hereafter GOODMAN AND GILMAN'S], pages 463-484 (Pergamon Press 1990).

The compositions of matter and pharmaceutical formulations and compositions employed in accordance with the present invention can cause a centrally mediated decrease in muscle tone and, hence, are useful for the acute or chronic alleviation of one or more symptoms or side effects of spasticity. In this context, "spasticity" refers to a heightened tone of skeletal muscle with is manifested by symptoms such as, but not limited to, painful flexor or extensor spasms, increased or exaggerated deep-tendon reflexes, hyperreflexia, loss of dexterity, muscular weakness, exaggerated tendon jerks, and clonus. The phrase "antispasticity agent" refers here to a composition that is useful for the symptomatic treatment of spasticity, as demonstrated by the alleviation of at least one of the following manifestations or side effects of spasticity: painful flexor or extensor spasms, increased or exaggerated deep-tendon reflexes, hyperreflexia, loss of dexterity, muscular weakness, exaggerated tendon jerks, and clonus, or the reduction of the frequency of these manifestations or side effects.

Accordingly, the "alleviation" of spasticity refers here to the lessening of one or more symptoms of spasticity, including, but not limited to, painful flexor or extensor spasms, increased or exaggerated deep-tendon reflexes, hyperreflexia, loss of dexterity, muscle weakness, exaggerated tendon jerks, and clonus, or the reduction of the frequency of these manifestations or side effects.

AFFECTIVE MOOD DISORDERS: These include conditions ranging from depression to dysphoric mania, for example, mania, schizoaffective disorder, traumatic brain injury-induced aggression, post-traumatic stress disorder, bipolar mood disorder, panic states, and behavioral dyscontrol syndromes. See Emrich et al., *J. Affective Disorders* 8:243-250 (1985) and Bernasconi et al., in ANTICONVULSANTS IN AFFECTIVE DISORDERS, pages 14-32 (*Excerpta Medica* 1984). The novel compositions and pharmaceutical formulations and compositions according to the present invention are effective in the treatment of these diseases, disorders, and conditions, and should exhibit improved side effect profiles when compared to currently existing therapeutic agents in this therapeutic category.

NEUROPATHIC PAIN SYNDROMES: Conditions in this category, involving "neuropathic pain," affect a significant number of patients suffering from disorders of the brain or spinal cord, such as stroke, trauma, multiple sclerosis, and diabetes. Casey, in PAIN AND CENTRAL NERVOUS SYSTEM DISEASE (Raven 1991). The use of anticonvulsants to treat various pain states has been documented extensively. Swendlow, *J. Clin. Neuropharmacol.* 7: 51-82 (1984). Thus, a novel composition or pharmaceutical formulation or composition of the present invention can be applied in similar fashion to ameliorate neuropathic pain.

HEADACHES: Headaches of the migraine type [Hering and Kuritzky, *Cephalagia* 12: 81-84 (1992)], the cluster type [Hering and Kuritzky, loc. cit. 9:195-198 (1989)], and the chronic type [Mathew and Sabiha, *Headache* 31: 71-74 (1991)] have been treated with anticonvulsants. The compositions and formulations of the present invention can therefore be used to alleviate the symptoms associated with each of these three headache types, without the adverse side effects of current existing therapies.

RESTLESSNESS SYNDROME: The phrase "restlessness syndrome" denotes a somatic (non-mental) restlessness characterized by involuntary movement of the limbs, as well as by a sense of physical (rather than mental) agitation, which is independent of mood and, hence, is distinguished from restlessness per se. [See Sachev et al., *Austral. New Zealand J. Psychiatry* 30:38-53 (1996)].

Restlessness syndromes, inclusive of numerous indications, can be observed in association with many organic and non-organic psychiatric illnesses. For example, drug-induced restlessness (tardive, chronic, and withdrawal akathisias), such as drug-induced extrapyramidal symptoms, is one of the most common side effects of neuroleptic drug therapy. Also within the restlessness-syndrome rubric are the so-called "restless leg syndrome" and "sleep-related periodic leg movements," pathologies that can be associated with head and/or spinal cord trauma and with lesions of the spinal cord. Idiopathic restless leg syndrome follows an autosomal dominant inheritance, with a variable clinical expression of symptoms. See O'Keefe, *Arch. Intern. Med.* 156: 243-248 (1996); Danek et al., in NEUROLOGICAL DISORDERS: COURSE AND TREATMENT, pages 819-823 (Academic Press 1996); Mellick and Mellick, *Neurology* 45(suppl.): 285-286 (1995). The present invention provides an effective therapy for restlessness syndromes with minimal side effects.

MOVEMENT DISORDERS: Various agents are known to decrease the dyskinetic movement characterizing movement disorders such as Parkinson's disease, Huntington's chorea, Alzheimer's disease, tardive dyskinesia, and stiff-man syndrome. Lloyd and Morselli, in PSYCHOPHARMACOLOGY: THE THIRD GENERATION OF PROGRESS (Raven Press 1987). A therapy within the present invention alleviates one or more symptoms of a movement disorder.

The compounds of the invention may also be useful as anxiety-reducing (anxiolytic) agents.

By "neurological disorder or disease" is meant a disorder or disease of the nervous system including, but not limited to, epilepsy, anxiety, multiple sclerosis, strokes, head trauma, spinal cord injuries, and chronic neurodegenerative diseases such as Parkinson's and Huntington's diseases, Alzheimer's disease, and amyotrophic lateral sclerosis. Also meant by "neurological disorder or disease" are those disease states and conditions in which an antispastic or anticonvulsant may be indicated, useful, recommended and/or prescribed.

By "neurodegenerative disease" is meant diseases such as, but not limited to, Huntington's Disease, Parkinson's Disease, Alzheimer's Disease, and amyotrophic lateral sclerosis (ALS).

By "anticonvulsant" is meant a compound capable of reducing the severity, number, or duration of convulsions produced, observed, or found in conditions such as generalized tonic-clonic seizures, absence seizures, myoclonic seizures, simple partial seizures, complex partial seizures, secondarily generalized partial seizures, status epilepticus, and trauma-induced seizures as occur following head injury or surgery.

By "anticonvulsant activity" is meant efficacy in reducing the severity, number, or duration of convulsions produced, observed, or found in conditions such as generalized tonic-clonic seizures, absence seizures, myoclonic seizures, simple partial seizures, complex partial seizures, secondarily generalized partial seizures, status epilepticus, and trauma-induced seizures, as occur following head injury or surgery.

By "therapeutic dose" is meant an amount of a compound that relieves to some extent one or more symptoms of the disease or condition of the patient. Additionally, by "therapeutic dose" is meant an amount that returns to normal, either partially or completely, physiological or biochemical parameters associated with or causative of the disease or condition. Generally, it is an amount between about 0.1-15-20-30 mg/kg body weight, depending on the age, size, and disease associated with the patient. The dosing can be one to four times a day.

By "pharmaceutical composition" is meant a therapeutically effective amount of a compound of the present invention in a pharmaceutically acceptable carrier, i.e., a formulation to which the compound can be added to dissolve or otherwise facilitate administration of the compound. Examples of pharmaceutically acceptable carriers include water, saline, and physiologically buffered saline. Such a pharmaceutical composition is provided in a suitable dose. Such compositions are generally those which are approved for use in treatment of a specific disorder by the FDA or its equivalent in non-U.S. countries.

It is understood that certain of the compounds of the present invention have one or more chiral stereocenter(s). Such compounds may demonstrate preferred biological activity as a racemic (or diastereomeric) mixture, as a mixture of R and S enantiomers (or diastereomers), or as pure enantiomers (R or S) (or diastereomers). When one pure enantiomer shows preferred biological activity, it is this preferred enantiomer is referred to as the eutomer, whereas the less preferred, less biologically active enantiomer is referred to as the distomer.

METHODS FOR PREPARING PHARMACEUTICAL FORMULATIONS AND COMPOSITIONS, AND METHODS FOR ADMINISTRATION: As demonstrated herein, useful pharmaceutical formulations and compositions of this invention may be used to treat neurological disorders or diseases. While these preparations will typically be used in therapy for human patients, they may also be used to treat similar or identical diseases in other vertebrates such as other primates, domestic animals, farm animals such as swine, cattle, and poultry, and sports animals and pets such as horses, dogs, and cats.

The present invention also is directed to pharmaceutical formulations and compositions containing combinations of two or more of the active compounds described above. The compounds of the present invention can be prepared (formulated) according to known methods for preparing pharmaceutically useful compositions, whereby active agents are combined in a mixture with a pharmaceutically acceptable carrier(s). For instance, see Gennaro (Ed.), REMINGTON'S PHARMACEUTICAL SCIENCES, 18th ed. (Mack Publishing Co., Easton, Pa., 1990) and GOODMAN AND GILMAN'S THE PHARMACOLOGICAL BASIS OF THERAPEUTICS. A compound and/or a composition is said to be in a "pharmaceutically acceptable carrier" if its administration can be tolerated by a recipient patient. Sterile phosphate-buffered saline is one example of a pharmaceutically acceptable carrier. Other suitable carriers (e.g., saline and Ringer's solutions) are well known to those skilled in the art (see below).

The pharmaceutically acceptable carrier includes a suitable excipient and/or auxiliary whose administration is tolerated by the patient. Pharmaceutically acceptable carriers which are known in the art include, but are not limited to, calcium carbonate, calcium phosphate, calcium sulfate, sucrose, dextrose, lactose, fructose, xylitol, sorbitol, starch, starch paste, cellulose derivatives, gelatin, polyvinylpyrrolidone, sodium chloride, dextrins, stearic acid, magnesium stearate, calcium stearate, vegetable oils, polyethylene glycol, sterile phosphate-buffered saline, saline, and Ringer's solutions, and mixtures thereof. See, for example, REMINGTON'S PHARMACEUTICAL SCIENCES, supra.

Pharmaceutically acceptable salts of organic acids (such as amino acids) which have been approved by the U.S. Food and Drug Administration for commercial marketing include sodium, potassium, lithium, zinc, aluminum, calcium, and magnesium salts. See REMINGTON'S PHARMACEUTICAL SCIENCES, 18th ed., page 1445 (Mack Publishing Co. 1990).

The compounds of the present invention and pharmaceutical compositions thereof are formulated as known in the art. For instance, the compound(s) of the present invention may be combined with a pharmaceutically acceptable carrier(s) and processed into a desired dosage form. The pharmaceutical compositions of the present invention may be produced or manufactured in a manner that is itself known, e.g., by means of conventional mixing, dissolving, granulating, dragee-making, levigating, emulsifying, encapsulating, entrapping, or lyophilizing processes which involve both the pharmaceutical composition of interest and its pharmaceutically acceptable carrier.

In general, the dosages of the compounds, formulations, and compositions described herein will vary depending upon such factors as the patient's age, weight, height, sex, general medical condition, and previous medical history. For purposes of therapy, a composition of the present invention and a pharmaceutically acceptable carrier are administered to a subject in need of such treatment in a therapeutically effective amount. The combination of active agents and carrier (formulation or composition) is said to be administered in a "therapeutically effective amount" if the amount administered is physiologically significant. A pharmaceutical composition is physiologically significant if its presence results in a detectable change in the physiology of a recipient patient. In the present context, for example, an anticonvulsant composition is physiologically significant if the presence of the composition results in the alleviation of one or more symptoms of epilepsy, such as seizures and/or convulsions. Further, the dose and perhaps dose frequency, will also vary according to the age, body weight, and response of the individual patient. A program comparable to that discussed above may be used in veterinary medicine.

The compounds of the present invention can be administered orally using solid oral dosage forms such as, for example, enteric-coated tablets, caplets, gelcaps, sprinkles, or capsules, or via liquid oral dosage forms such as syrups or elixirs. Unit solid oral dosage forms preferably contain appropriate amounts of active compounds per tablet or capsule such that they can be taken 1-2 at a time for a maximum of two times per day. Liquid formulations can also be employed with active compounds so as to provide 1-2 teaspoonfuls per dose. Furthermore, corresponding reduced dosage pediatric chewable and liquid oral dosage forms can also be prepared and administered. These compounds can also be added to foods and beverages in the form of drops (with a dropper from a "concentrate" preparation) for oral administration. In addition, the compounds of the present invention may also be formulated into chewing gum to facilitate oral delivery and absorption. Appropriate dosages for each of the compounds used in the formulations and compositions of the present invention can be discerned from the foregoing descriptions by those skilled in the art.

Alternatively, the compounds of the present invention can be administered by injection or other systemic routes, such as transdermal or transmucosal administration, for example, nasally, sublingually, buccally, vaginally, or rectally, via suppositories. Other routes of administration (e.g., useful in veterinary applications) include intestinal and parenteral delivery, including intramuscular, subcutaneous, and/or intramedullary injections, as well as intrathecal, direct intracerebroventricular, intravenous, intraperitoneal, intranasal, or intraocular injections. Oral administration is much more convenient, however, and therefore is preferred.

The present invention thus contemplates a variety of compounds that are suitable for oral, parenteral, transdermal, transmucosal, intranasal, sublingual, buccal, or rectal administration. It is further understood that the compounds of the present invention can be used in combination with other pharmaceutically active ingredients to prepare still other novel pharmaceutical compositions.

DEMONSTRATING THERAPY-IMPLICATING AND THERAPEUTICALLY RELEVANT ACTIVITY: The suitability and therapeutic effectiveness of a given pharmaceutical formulation or composition for the alleviation of symptoms, as discussed above, can be demonstrated by using the animal models, testing, and screening methods which are described in, e.g., U.S. Pat. Nos. 6,589,994, 6,617,358, and 7,265,155, which are hereby incorporated herein in their entirety.

The therapeutic effects of the compounds of the invention described above, combined with a general lack of toxicity, make the compounds of the present invention ideal agents for the treatment of the conditions described above. With this background, the present invention will be understood more readily by those skilled in the art by reference to the examples below, which are provided for purposes of illustration and are not intended to be limiting of the invention.

EXAMPLES

Example 1

Preparation of Compound A
[3-(4-Chlorophenyl)-3-methylbutyramide]

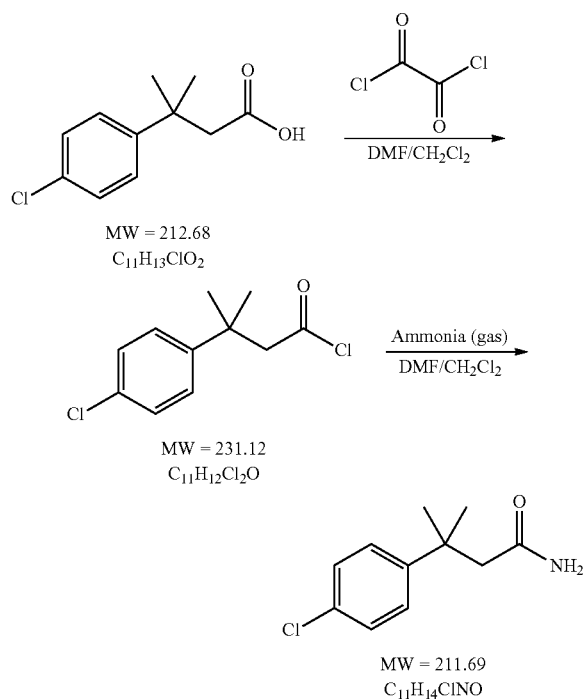

A solution of 3-(4-chlorophenyl)-3-methylbutyric acid (6.1 g, 41.9 mmol) in $CH_2Cl_2$ (100 mL) and DMF (0.2 mL) was treated with oxalyl chloride (5.2 mL, 7.45 mmol) at 0° C. under static nitrogen. The reaction solution was stirred at room temperature overnight under nitrogen. The excess dichloromethane was removed under reduced pressure. The resulting residue was azeotroped by toluene (50 mL).

Ammonia (gas) was bubbled through the solution of the acid chloride [3-(4-chlorophenyl)-3-methylbutyryl chloride] in anhydrous THF (100 mL) at 5 degrees Celsius for 15 minutes. The reaction mixture was stirred overnight at room temperature under static nitrogen.

The white precipitate (ammonium chloride) was filtered and washed with THF (100 mL). The filtrate and wash-solution were combined and evaporated under reduced pressure. The resulting white solid was re-dissolved in ethyl acetate (300 mL). The ethyl acetate layer was washed with $H_2O$, 1.0 M HCl, a saturated solution of sodium bicarbonate, and brine solution. The ethyl acetate solution was then dried over magnesium sulfate, filtered, and evaporated under reduced pressure. The resulting white solid was triturated with a chilled solution of diethyl ether and hexane (50:50). This afforded 4.22 g of white flakes [3-(4-chlorophenyl)-3-methylbutyramide] (69% yield). This material was determined to be 100% pure by GC/MS analysis. $^1H$ NMR spectroscopy gave signals consistent with the product's structure and indicated greater than 98% purity.

Example 2

Preparation of Compound B
[3-(4-Chlorophenyl)-3,N-dimethylbutyramide]

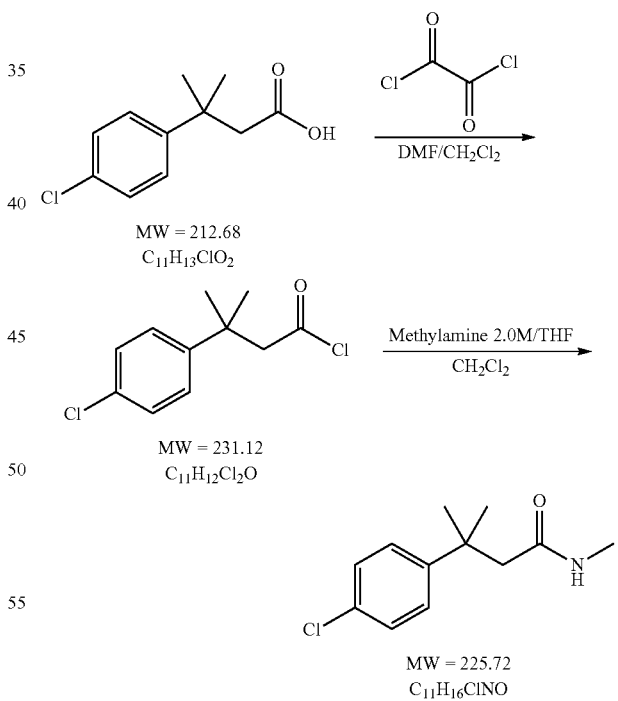

A solution of 3-(4-chlorophenyl)-3-methylbutyric acid (5.95 g, 28 mmol) in $CH_2Cl_2$ (100 mL) and DMF (0.2 mL) was treated with oxalyl chloride (5.2 mL, 7.45 mmol) at 0° C. under static nitrogen. The reaction solution was stirred at room temperature overnight under nitrogen. The excess dichloromethane was removed under reduced pressure. The resulting residue was azeotroped by toluene (50 mL).

The residue was dissolved in 150 mL of dry THF and treated with methylamine solution (2.0 M in THF, 45 mL, 84 mmol) at 5 degrees Celsius. The reaction mixture was stirred overnight at room temperature under static nitrogen.

The white precipitate was filtered and washed with THF (100 mL). The filtrate and wash-solution were combined and evaporated under reduced pressure. The resulting white solid was re-dissolved in diethyl ether (300 mL). The ether layer was washed with $H_2O$, 1.0 M HCl, a saturated solution of sodium bicarbonate, and brine solution. The ether solution was then dried over magnesium sulfate, filtered, and evaporated under reduced pressure. The resulting white solid was triturated with a chilled solution of diethyl ether and hexane (50:50). This afforded 5.46 g of white flakes [3-(4-chlorophenyl)-3,N-dimethylbutyramide] (86% yield). This material was determined to be 100% pure by GC/MS analysis. $^1$H NMR spectroscopy gave signals consistent with the product's structure and indicated greater than 98% purity.

The white precipitate (ammonium chloride) was filtered and washed with THF (100 mL). The filtrate and wash-solution were combined and evaporated under reduced pressure. The resulting white solid was re-dissolved in ethyl acetate (300 mL). The ethyl acetate layer was washed with $H_2O$, 1.0 M HCl, a saturated solution of sodium bicarbonate, and brine solution. The ethyl acetate solution was then dried over magnesium sulfate, filtered, and evaporated under reduced pressure. Crude material was purified using a Biotage SP4 System (Column Si 40+M 0344-1, 95:5, $CH_2Cl_2$: MeOH). The resulting off-white solid was triturated with a chilled solution of diethyl ether and hexane (50:50). This afforded 2.9 g of white solid [(R)-3-phenylbutyramide] (73% yield). This material was determined to be 100% pure by GC/MS analysis. $^1$H NMR spectroscopy gave signals consistent with the product's structure and indicated greater than 98% purity.

Example 3

Preparation of Compound C
[(R)-3-Phenylbutyramide]

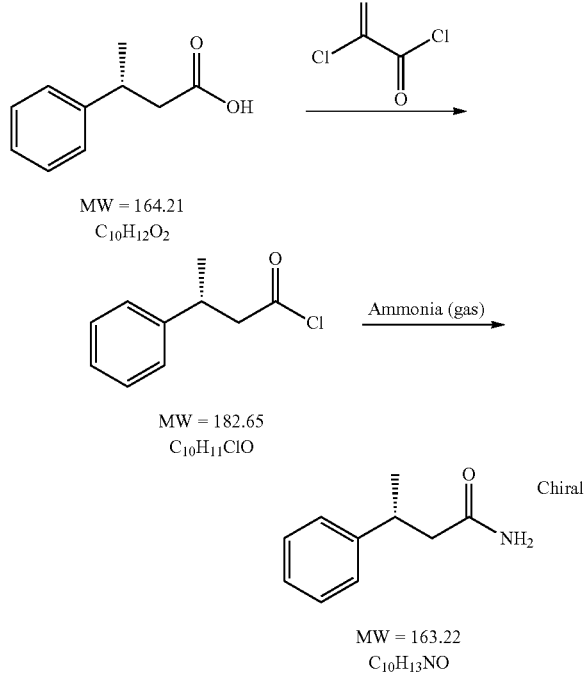

Example 4

Preparation of Compound D
[3-(3-Fluorophenyl)butyramide]

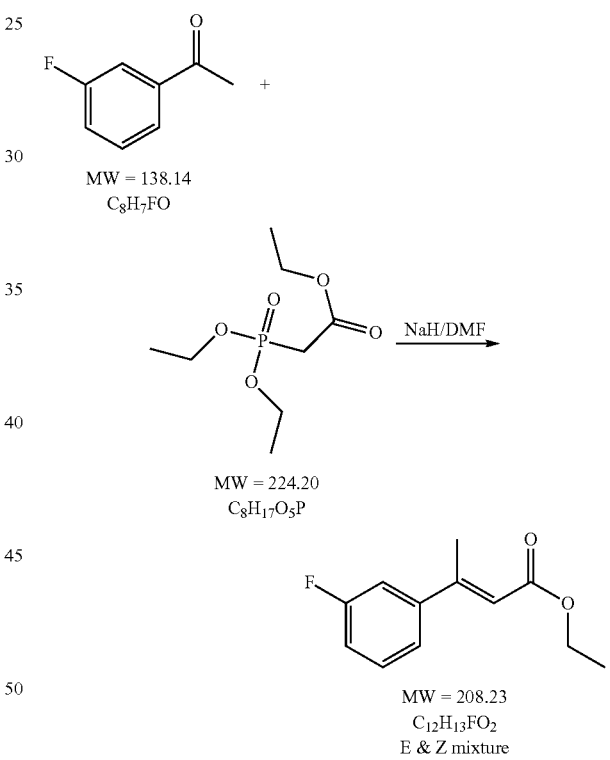

A solution of (R)-3-phenylbutyric acid (4 g, 24.36 mmol) in $CH_2Cl_2$ (75 mL) and DMF (0.1 mL) was treated with oxalyl chloride (3.0 mL, 34.0 mmol) at 0° C. under static nitrogen. The reaction solution was stirred at room temperature overnight under nitrogen. The excess dichloromethane was removed under reduced pressure. The resulting residue was azeotroped by toluene (50 mL).

Ammonia (gas) was bubbled through the solution of the acid chloride [(R)-3-phenylbutyrl chloride] in anhydrous THF (100 mL) at 5 degrees Celsius for 15 minutes. The reaction mixture was stirred overnight at room temperature under static nitrogen.

In a 3-necked, 500-mL round-bottomed flask, a suspension of sodium hydride (60% in oil, 1.1 eq. 80 mmol, 3.20 g) in N,N-dimethylformamide (DMF, 100 mL) under nitrogen was treated drop-wise with a solution of triethyl phosphonoacetate (1.2 eq. 87 mmol, 19.50 g) in DMF (50 mL). After the addition, the reaction mixture was heated in a water bath (100° C.) until all visible signs of the sodium hydride were gone (30 minutes). The mixture was cooled to ambient temperature and then treated with a solution of 3'-fluoroacetophenone (1.0 eq. 10 g, 72.4 mmol) in DMF (50 mL). The reaction mixture was stirred for 2 hours at ambient temperature and a 1-mL aliquot was removed and quenched in water (~2 mL). Diethyl ether (~2 mL) was added to this and the mixture was equilibrated. Analysis of the organic layer by GC/MS showed complete consumption of the starting benzophenone. As a result, the reaction mixture was quenched by the addition of water. The mixture was transferred to a large round-bottomed flask and the majority of the solvents were removed using a rotary evaporator. The mixture was cooled and transferred to a separatory funnel using [a] diethyl ether (500 mL) and water (250 mL). The mixture was equilibrated and the aqueous layer was removed. The organic layer was washed an additional 3 times with water (3×250 mL). GC/MS analysis of this solution showed only product (with no remaining phosphonoacetate). The organic solution was dried over anhydrous MgSO$_4$, filtered, and concentrated to afford 18.09 g of crude material (containing oil from the sodium hydride).

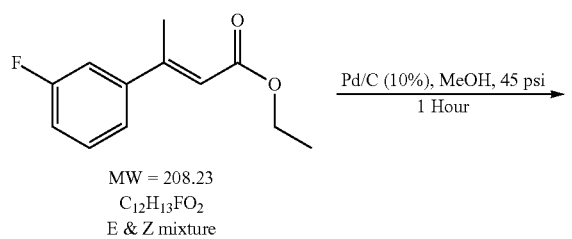

A solution of crude of [3-(3-fluorophenyl)-but-2-enoic acid ethyl ester] (9 g, 0.015 mmol) in methanol (75 mL) was treated with Pd/C (10%, 450 mg). The reaction mixture was subjected to hydrogenation at 45 psi for 1 hour. The reaction mixture was passed through a Celite plug to remove palladium on carbon. The filtrate was concentrated under reduced pressure. This afforded 10.1 g of a colorless oil [3-(3-fluorophenyl)butyric acid ethyl ester]. The material was determined to be 94% pure by GC/MS analysis. This product was used without purification (to remove mineral oil).

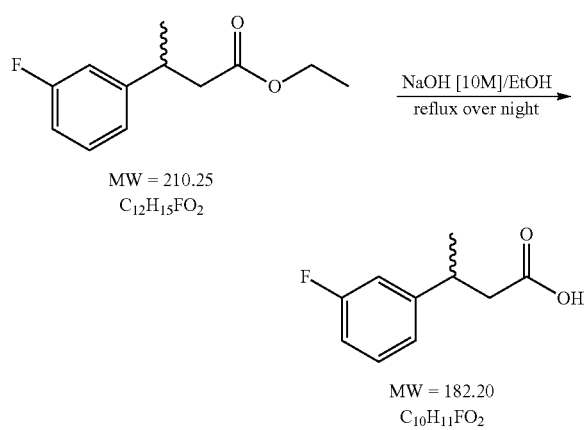

A crude solution of 3-(3-fluorophenyl)butyric acid ethyl ester, 10.1 g, 48 mmol] in ethanol (50 mL) was treated with 10 M NaOH solution (50 mL, 857 mmol). The reaction mixture was refluxed overnight. The reaction mixture was dried under reduced pressure in order to get rid of the ethyl alcohol. The resulting residue was re-dissolved in 150 mL of water. The mixture was transferred to a separatory funnel using water (50 mL) and diethyl ether (200 mL). The mixture was equilibrated and the ether layer was removed. The aqueous layer was acidified by HCl solution (pH~2) and extracted with diethyl ether (300 mL). The organic layer was dried over magnesium sulfate, filtered, and concentrated under reduced pressure. This afforded 8.1 g of an orange viscous oil, 3-(3-fluorophenyl)butyric acid (92.6% yield). This material was determined to be 100% pure by GC/MS analysis.

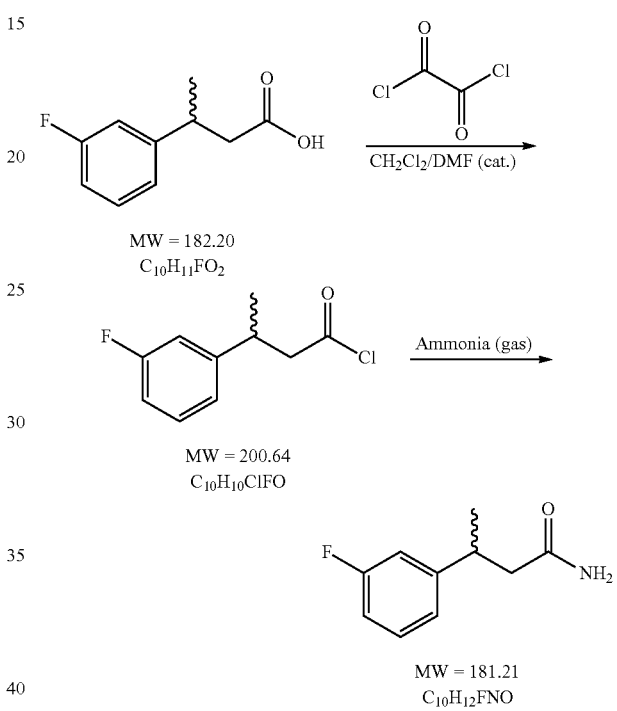

A solution of 3-(3-fluorophenyl)butyric acid (8.1 g, 44.46 mmol) in CH$_2$Cl$_2$ (100 mL) and DMF (0.7 mL) was treated with oxalyl chloride (5.43 mL, 7.9 mmol) at 0° C. under static nitrogen. The reaction solution was stirred at room temperature overnight under nitrogen. The excess dichloromethane was removed under reduced pressure. The resulting residue was azeotroped by toluene (70 mL).

Ammonia (gas) was bubbled through the solution of the acid chloride [3-(3-fluoro-phenyl)butyryl chloride] in anhydrous THF (100 mL) at 5 degrees Celsius for 15 minutes. The reaction mixture was stirred overnight at room temperature under static nitrogen.

The white precipitate (ammonium chloride) was filtered and washed with THF (200 mL). The filtrate and wash-solution were combined and evaporated under reduced pressure. The resulting white solid was re-dissolved in ethyl acetate (350 mL). The ethyl acetate layer was washed with H$_2$O, 1.0 M HCl, a saturated solution of sodium bicarbonate, and brine solution. The ethyl acetate solution was then dried over magnesium sulfate, filtered, and evaporated under reduced pressure. The resulting white solid was triturated with a chilled solution of diethyl ether and hexane (50:50). This afforded 6.8 g of off-white powder of 3-(3-fluorophenyl)butyramide (84% yield). This material was determined to be 100% pure by GC/MS analysis (a mixture of R and S enantiomers). $^1$H-NMR spectroscopy gave signals consistent with the product's structure and indicated greater than 98% purity.

Examples 5-14

Preparation of Compounds E-N

Compounds E-N were prepared using the corresponding acetophenones (shown in Table 1 below) with the method used for the preparation of Compound D in Example 4, above. In addition, Compound M (Example 13) and Compound N (Example 14) were prepared using the corresponding amines, i.e., methylamine and dimethylamine, respectively. All of the final products were determined to be 100% pure by GC/MS analysis. $^1$H-NMR spectroscopy of each final product gave signals consistent with its structure and indicated greater than 98% purity.

TABLE 1

| Example No. | Formula | Weight (g) | % Yield | Product Chemical Name | Corresponding Acetophenone |
|---|---|---|---|---|---|
| 5 | E | 3.2 | 91 | 3-(4-fluorophenyl)-butyramide | 4'-fluoroacetophenone |
| 6 | F | 5.7 | 79 | 3-[4-(trifluoromethyl)-phenyl]butyramide | 4'-(trifluoromethyl)acetophenone |
| 7 | G | 6.8 | 84 | 3-[3-(trifluoromethyl)-phenyl]butyramide | 3'-(trifluoromethyl)acetophenone |
| 8 | H | 3.8 | 81 | 3-[4-(trifluoromethoxy)-phenyl]butyramide | 4'-(trifluoromethoxy)acetophenone |
| 9 | I | 1.9 | 86 | 3-[3-(trifluoromethoxy)-phenyl]butyramide | 3'-(trifluoromethoxy)acetophenone |
| 10 | J | 2.3 | 84 | 3-(3-chloro-4-methoxy-phenyl)butyramide | 3'-chloro-4'-methoxyacetophenone |
| 11 | K | 3.6 | 70 | 3-(3,4-ethylenedioxy-phenyl)butyramide | 3',4'-ethylenedioxyacetophenone |
| 12 | L | 2.5 | 91 | 3-(3,4-methylenedioxy-phenyl)butyramide | 3',4'-methylenedioxyacetophenone |
| 13 | M | 2.7 | 90 | N-methyl-3-(3,4-methylenedioxy-phenyl)butyramide | 3',4'-methylenedioxyacetophenone |
| 14 | N | 2.3 | 73 | N,N-dimethyl-3-(3,4-methylenedioxy-phenyl)butyramide | 3',4'-methylenedioxyacetophenone |

Example 15

Preparation of Compound O [3-(4-Cyanophenoxy)butyramide]

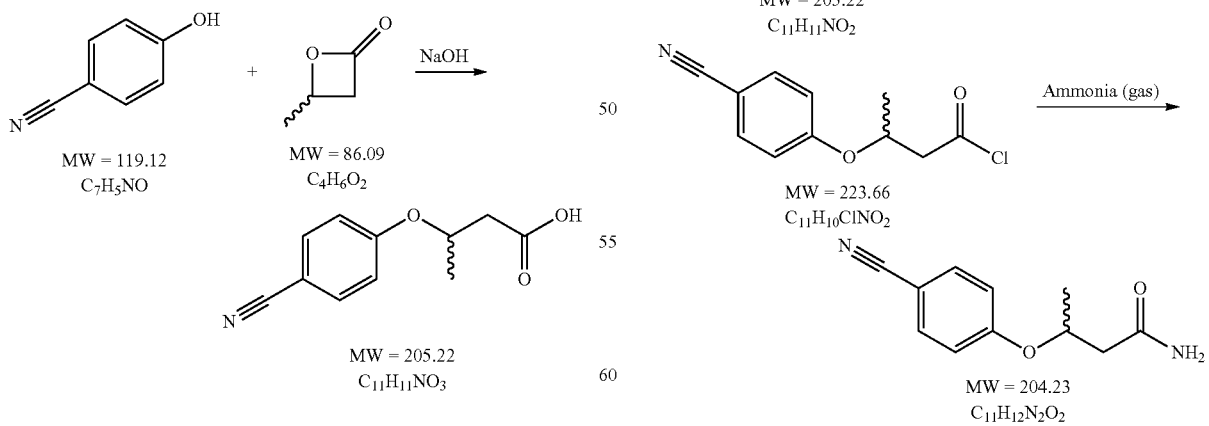

A solution of 4 g (0.1 mol) of sodium hydroxide in 100 mL of H$_2$O and 11.9 g (0.1 mol) of 4-cyanophenol was heated at reflux for 15 minutes. β-Butyrolactone (8.6 g, 0.1 mol) was added to the refluxing solution over 15 hours. The reaction was then cooled to room temperature. The reaction solution was transferred to a separatory funnel using water (200 mL) and diethyl ether (200 mL). The mixture was equilibrated and the ether layer was removed. The aqueous layer was acidified by HCl solution (pH~2) and extracted with ethyl acetate (300 mL). The ethyl acetate layer was dried over magnesium sulfate, filtered, and concentrated under reduced pressure to afford 10.78 g of crude product. This crude material was purified using a Biotage SP4 System (Column Si 65i, 9:1 CH$_2$Cl$_2$:MeOH), which afforded 9.87 g of a pale-yellow viscous oil [3-(4-cyanophenoxy)butyric acid], which solidified upon standing at room temperature. This material was determined to be 96% pure by GC/MS analysis. This material was used without further purification.

A crude solution of [3-(4-cyanophenoxy)butyric acid] (10.8 g, 52.6 mmol) in CH$_2$Cl$_2$ (100 mL) and DMF (0.21 mL) was treated with oxalyl chloride (6 mL, 68.4 mmol) at 0° C. under static nitrogen. The reaction solution was stirred at room temperature overnight under nitrogen. The excess dichloromethane was removed under reduced pressure.

Ammonia (gas) was bubbled through the solution of the acid chloride [3-(4-cyanophenoxy)butyryl chloride] in anhydrous CH$_2$Cl$_2$ (150 mL) at 5 degrees Celsius for 15 minutes. The reaction mixture was stirred overnight at room temperature under static nitrogen.

The white precipitate (ammonium chloride) was filtered and washed with CH$_2$Cl$_2$ (100 mL). The filtrate and wash-solution were combined and evaporated under reduced pressure. The resulting white solid was re-dissolved in ether (250 mL). The ether layer washed with H$_2$O, 1.0 M HCl, a saturated solution of sodium bicarbonate, and brine solution. The ether solution was then dried over magnesium sulfate, filtered, and evaporated under reduced pressure. Crude material was purified using a Biotage SP4 System (Column Si 40+M 0344-1, 95:5, CH$_2$Cl$_2$:MeOH). This afforded 2.987 g of an off-white solid [3-(4-cyanophenoxy)butyramide] (29% yield). This material was determined to be 97% pure by GC/MS analysis. $^1$H NMR spectroscopy gave signals consistent with the product's structure and indicated greater than 98% purity.

Example 16

Preparation of Compound P
[trans-2-phenylcyclopropane-1-carboxamide]

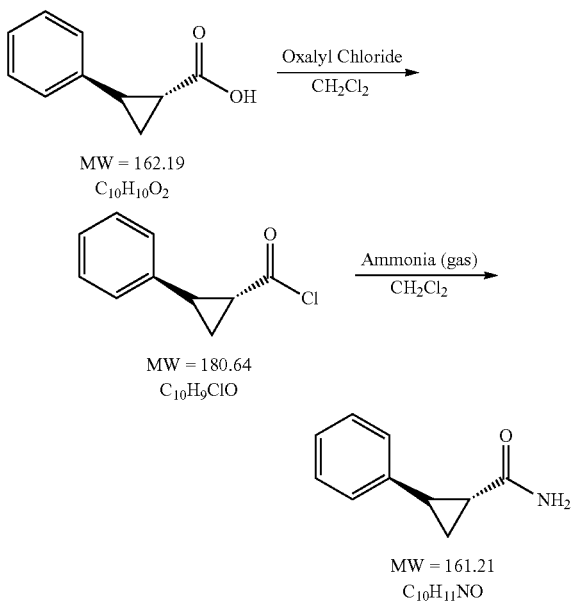

A solution trans-2-phenylcyclopropane-1-carboxylic acid (2.1 g., 12.8 mmol) in CH$_2$Cl$_2$ (50 mL) and DMF (0.20 mL) was treated with oxalyl chloride (1.5 mL, 16.7 mmol) at 0° C. under static nitrogen. The reaction solution was stirred at room temperature overnight under nitrogen. The excess dichloromethane was removed under reduced pressure.

Ammonia (gas) was bubbled through the solution of the acid chloride [trans-2-phenylcyclopropane-1-carboxyl chloride] in anhydrous CH$_2$Cl$_2$ (100 mL) at 5 degrees Celsius for 15 minutes. The reaction mixture was stirred overnight at room temperature under nitrogen.

The reaction mixture was evaporated under reduced pressure and the resulting residue re-dissolved in an ethyl acetate/water mixture. The mixture was transferred to a reparatory funnel using H$_2$O (60 mL) and ethyl acetate (100 mL). The mixture was equilibrated and the aqueous phase was removed. The organic layer was washed with 1.0 M HCl (10 mL), H$_2$O (70 mL), and brine (75 mL), consecutively. The organic layer was dried over anhydrous magnesium sulfate, filtered, and [the] excess solvent was removed under reduced pressure. The resulting light-brown solid was purified using a Biotage SP4 System (Column Si 40+S 90:10 CH$_2$Cl$_2$:MeOH), which afforded 1.127 g of white powder [trans-2-phenylcyclopropane-1-carboxamide] (54% yield). This material was determined to be 100% pure by GC/MS analysis. $^1$H-NMR spectroscopy gave signals consistent with the product's structure and indicated greater than 98% purity.

Example 17

Preparation of Compound Q [trans-2-Phenylcyclopropane-carboxylic acid-((S)-1-carbamoyl-3-methylbutyl)amide]

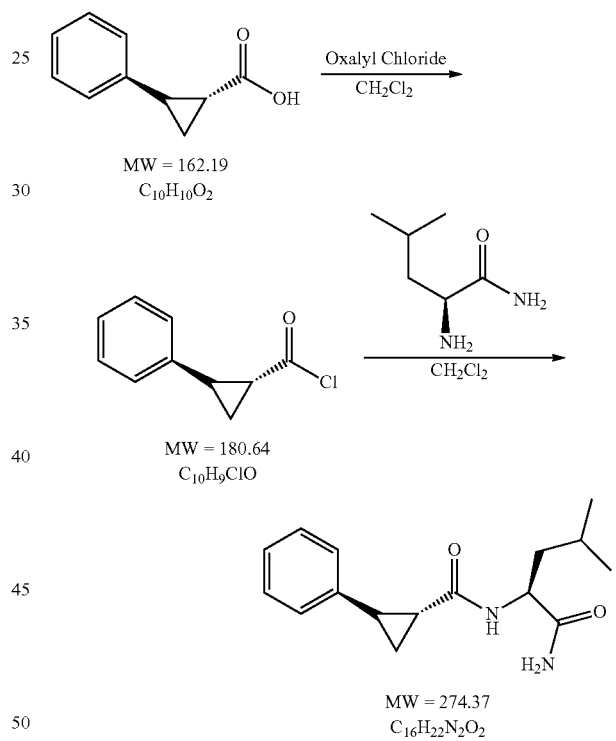

A solution of trans-2-phenylcyclopropane-1-carboxylic acid (0.905 g., 5.6 mmol) in CH$_2$Cl$_2$ (30 mL) and DMF (0.05 mL) was treated with oxalyl chloride (0.65 mL, 7.23 mmol) at 0° C. under static nitrogen. The reaction solution was stirred at room temperature overnight under nitrogen. The excess dichloromethane was removed under reduced pressure.

The solution of the acid chloride [trans-2-phenylcyclopropane-1-carboxyl chloride] in CH$_2$Cl$_2$ (50 mL) was added drop-wise in to a solution of H-Leu-NH$_2$ [L-leucine amide, (S)-2-amino-4-methyl-n-valeramide] (0.761 g, 5.8 mmol) and triethylamine (1.13 g, 11.1 mmol) in CH$_2$Cl$_2$ (60 mL) at zero degrees Celsius. The reaction mixture was stirred at room temperature under nitrogen overnight.

The reaction mixture was evaporated under reduced pressure and the resulting residue was re-dissolved in an ethyl acetate/water mixture. The mixture was transferred to a separatory funnel using H₂O (50 mL) and ethyl acetate (80 mL). The mixture was equilibrated and the aqueous phase was removed. The organic layer was washed with 1.0 M HCl (20 mL), H₂O (90 mL), and brine (120 mL), consecutively. The organic layer was dried over anhydrous magnesium sulfate, filtered, and the excess solvent was removed under reduced pressure. The resulting orange-brown solid was purified using a Biotage SP4 System (Column Si 40+M 90:10, CH₂Cl₂:MeOH), which afforded 0.365 g of white powder [trans-2-phenylcyclopropanecarboxylic acid-((S)-1-carbamoyl-3-methylbutyl)-amide] (24% yield). This material was determined to be 100% pure by GC/MS analysis. ¹H-NMR spectroscopy gave signals consistent with the product's structure and indicated greater than 98% purity.

Example 18

Preparation of Compound U
[2-[1-(4-Methoxyphenyl)cyclopropyl]-acetamide]

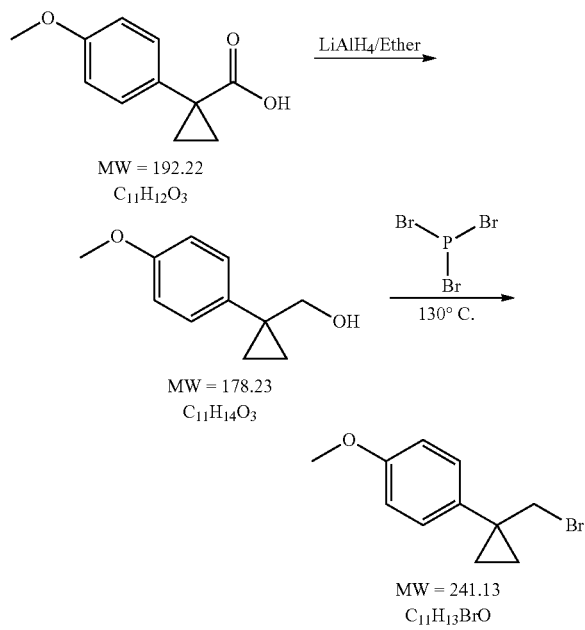

A stirred suspension of lithium aluminum hydride (0.211 mol) in anhydrous ether (200 mL) is treated with 1-(4-methoxyphenyl)-1-cyclopropanecarboxylic acid (0.1406 mol) in 100 mL of ether at 0° C. The reaction mixture is then stirred at room temperature under nitrogen overnight. The reaction mixture is quenched by the drop-wise addition of 100 mL of deionized H₂O. The mixture is filtered and the cake solid is washed with diethyl ether (1 L). The filtrate mixture (ether and water) is transferred into a separatory funnel. The organic layer is separated from the aqueous layer and washed with brine solution. The ether layer is dried over magnesium sulfate, filtered, and concentrated under reduced pressure at room temperature. This affords [1-(4-methoxy-phenyl)-cyclopropyl]-methanol.

A neat solution of [1-(4-methoxyphenyl)cyclopropyl] methanol (0.074 mol) is treated with phosphorous tribromide (0.081 mol) drop-wise at 0° C. under static nitrogen. The reaction solution is heated to 130° C. and the temperature is maintained for 6 hours. The reaction mixture is cooled down to room temperature and the orange precipitate is filtered off. The orange precipitate is washed with 200 mL of diethyl ether. The filtrate is transferred into a separatory funnel using 150 mL of water and 200 mL of diethyl ether. The mixture is equilibrated and the aqueous layer is extracted one more time with 200 mL of diethyl ether. The ether extracts and etherwash are combined and washed with saturated sodium bicarbonate solution and brine. Then the ether extracts are dried over magnesium sulfate and the excess diethyl ether is removed under reduced pressure at 30° C. This affords 1-(1-bromomethyl-cyclopropyl)-4-methoxybenzene. The crude material is converted into the corresponding nitrile without further purification.

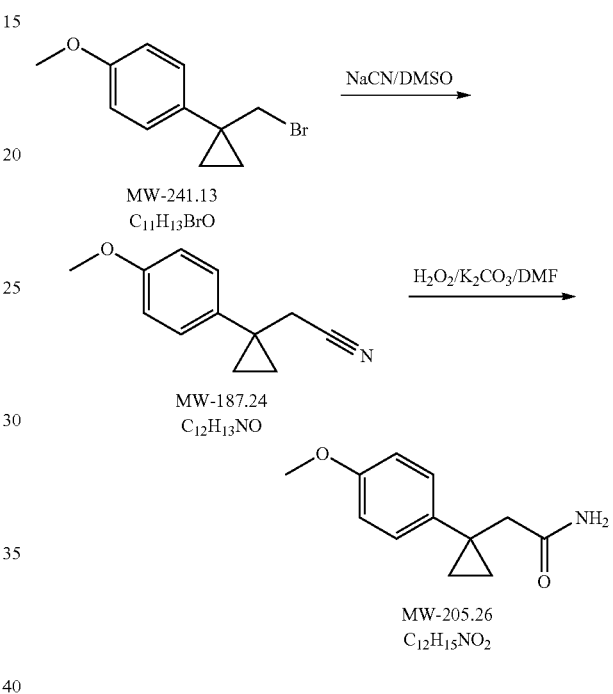

A crude solution of 1-(1-bromomethyl-cyclopropyl)-4-methoxybenzene (60.3 mmol) in dimethyl sulfoxide (60 mL) is treated with sodium cyanide (180.7 mmol). The reaction mixture is heated to 95 degrees Celsius overnight under nitrogen. The reaction mixture is transferred to a separatory funnel using brine (150 mL) and chloroform (300 mL). The reaction mixture is equilibrated and the aqueous layer is removed. The aqueous layer is extracted an additional two times with chloroform (2×300 mL). The combined organic extract is dried over anhydrous MgSO₄, filtered, and concentrated under reduced pressure to afford [1-(4-methoxyphenyl)cyclopropyl]acetonitrile. This crude material is used in the next step (hydrolysis of the nitrile to the corresponding amide) without further purification. [Alternatively, the corresponding carboxylic acid can be obtained from this material by acid hydrolysis (e.g., using sulfuric acid).]

A solution of [1-(4-methoxyphenyl)cyclopropyl]acetonitrile (60.4 mmol) in DMSO (75 mL) is treated with H₂O₂ (50% w/w) (434 mmol) and potassium carbonate (121 mmol) at zero degrees Celsius. The reaction mixture is stirred at room temperature over the weekend. The reaction mixture is transferred into a separatory funnel using water (100 mL) and CH₂Cl₂ (200 mL). The mixture is equilibrated and the CH₂Cl₂ layer is removed. The aqueous layer is extracted two additional times with CH₂Cl₂ (2×300 mL). The combined CH₂Cl₂ extracts are washed 5 consecutive times with water (5×200 mL) followed by a brine (500 mL) wash, dried over anhydrous MgSO₄, filtered, and concentrated under reduced pressure, which affords 2-[1-(4-methoxyphenyl)-cyclopropyl]-acetamide.

Example 19

Preparation of Compound V
[3-(4-Chlorophenoxy)-3-methylbutyramide]

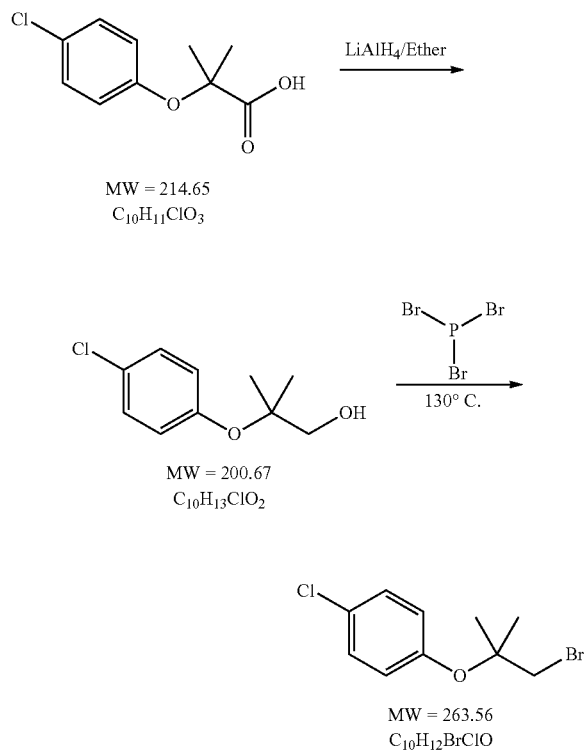

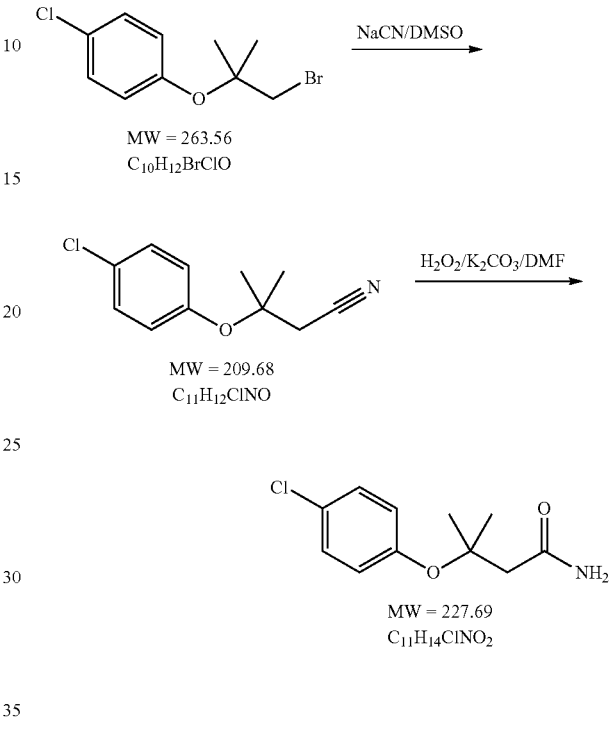

A stirred suspension of lithium aluminum hydride (0.211 mol) in anhydrous ether (200 mL) is treated with 2-(4-chlorophenoxy)-2-methylpropanoic acid (0.1406 mol) in 100 mL of ether at 0° C. The reaction mixture is stirred at room temperature under nitrogen overnight. The reaction mixture is quenched by the drop-wise addition of 100 mL of deionized H₂O. The mixture is filtered and the cake solid is washed with diethyl ether (1 L). The filtrate mixture (ether and water) is transferred into a separatory funnel. The organic layer is separated from the aqueous layer and washed with brine solution. The ether layer is dried over magnesium sulfate, filtered, and concentrated under reduced pressure at room temperature. This affords 2-(4-chlorophenoxy)-2-methylpropan-1-ol.

A neat solution of 2-(4-chlorophenoxy)-2-methylpropan-1-ol (0.074 mol) is treated with phosphorous tribromide (0.081 mol) drop-wise at 0° C. under static nitrogen. The reaction solution is heated to 130° C. and the temperature is maintained for 6 hours. The reaction mixture is cooled down to room temperature and the orange precipitate is filtered off. The orange precipitate is washed with 200 mL of diethyl ether. The filtrate is transferred into a separatory funnel using 150 mL of water and 200 mL of diethyl ether. The mixture is equilibrated and the aqueous layer is extracted one more time with 200 mL of diethyl ether. The ether extracts and ether-wash are combined and washed with saturated sodium bicarbonate solution and brine. Then the ether extract is dried over magnesium sulfate and the excess diethyl ether is removed under reduced pressure at 30° C. This affords 1-(2-bromo-1,1-dimethylethoxy)-4-chlorobenzene. The crude 1-(2-bromo-1,1-dimethylethoxy)-4-chlorobenzene is converted into the corresponding nitrile without further purification.

A crude solution of 1-(2-bromo-1,1-dimethylethoxy)-4-chlorobenzene (60.3 mmol) in dimethyl sulfoxide (60 mL) is treated with sodium cyanide (180.7 mmol). The reaction mixture is heated to 95 degrees Celsius overnight under nitrogen. The reaction mixture is transferred into a separatory funnel using brine (150 mL) and chloroform (300 mL). The reaction mixture is equilibrated and the aqueous layer is removed. The aqueous layer is extracted an additional two times with chloroform (2×300 mL). The combined organic extracts are dried over anhydrous MgSO₄, filtered, and concentrated under reduced pressure to afford 3-(4-chlorophenoxy)-3-methylbutyronitrile. This crude material is used in the next step (hydrolysis of the nitrile into the corresponding amide) without further purification. [Alternatively, the corresponding carboxylic acid can be obtained from this material by acid hydrolysis (e.g., using sulfuric acid).]

A solution of 3-(4-chlorophenoxy)-3-methylbutyronitrile (60.4 mmol) in DMSO (75 mL) is treated with H₂O₂ (50% w/w) (434 mmol) and potassium carbonate (121 mmol) at zero degrees Celsius. The reaction mixture is stirred at room temperature over the weekend. The reaction mixture is transferred into a separatory funnel using water (100 mL) and CH₂Cl₂ (200 mL). The mixture is equilibrated and the CH₂Cl₂ layer is removed. The aqueous layer is extracted two additional times with CH₂Cl₂ (2×300 mL). The combined CH₂Cl₂ extracts are washed 5 consecutive times with water (5×200 mL) followed by a brine (500 mL) wash, dried over anhydrous MgSO₄, filtered, and concentrated under reduced pressure, which affords 3-(4-chlorophenoxy)-3-methylbutyramide.

Example 20

Preparation of Compound AG
[(R)-3-(4-Trifluoromethylphenyl)-butyramide]

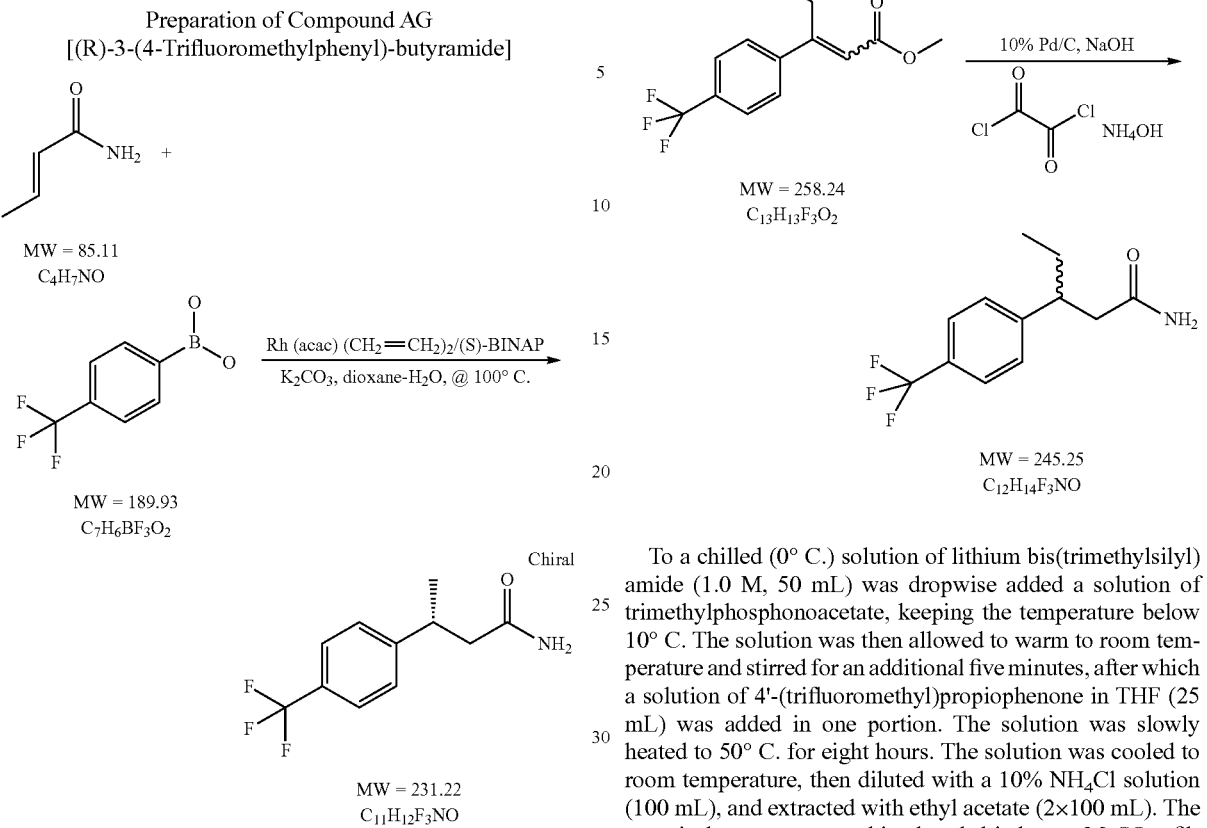

Acetylacetonatobis(ethylene)rhodium(I) (0.3 mmol), (S)-(−)-2,2'-Bis(diphenyl-phosphino)-1,1'-binaphthalene (0.045 mmol), 4-(trifluoromethyl)phenylboronic acid (2 mmol), $K_2CO_3$ (0.5 mmol), and but-2-enoic acid amide (1 mmol) are added into a 25-mL round-bottomed flask containing a magnetic stirrer bar, a septum inlet, and a reflux condenser. The flask is flashed with argon and then charged with 1,4-dioxane (3 mL) and de-ionized $H_2O$ (0.5 mL). The reaction mixture is stirred for 16 hours at 100° C. The (R)-3-(4-trifluoromethylphenyl)butyramide is extracted with ethyl acetate, washed with brine, and dried over anhydrous magnesium sulfate. Chromatography over silica gel gives the desired product.

Example 21

Preparation of Compound AA
[3-(4-Trifluoromethylphenyl)-pentanamide]

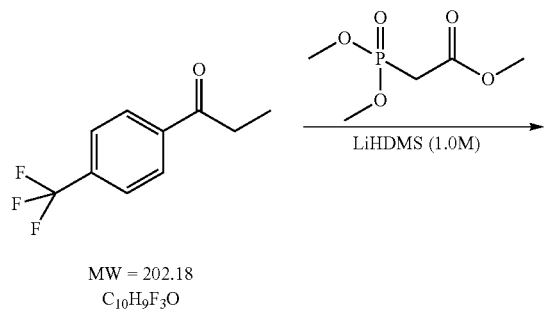

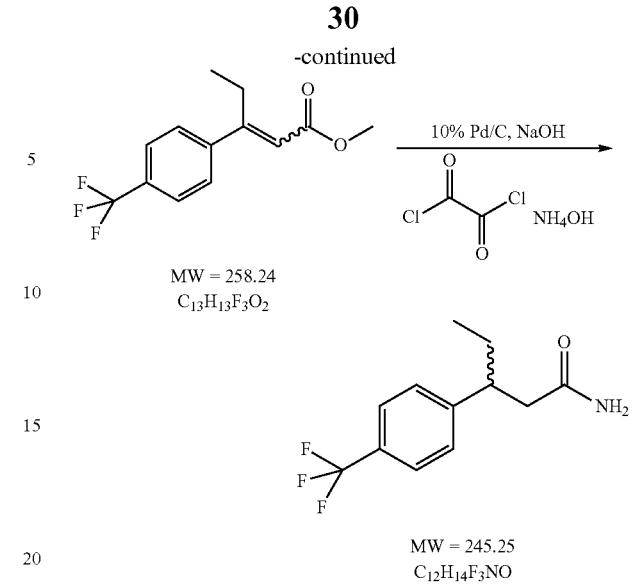

To a chilled (0° C.) solution of lithium bis(trimethylsilyl) amide (1.0 M, 50 mL) was dropwise added a solution of trimethylphosphonoacetate, keeping the temperature below 10° C. The solution was then allowed to warm to room temperature and stirred for an additional five minutes, after which a solution of 4'-(trifluoromethyl)propiophenone in THF (25 mL) was added in one portion. The solution was slowly heated to 50° C. for eight hours. The solution was cooled to room temperature, then diluted with a 10% $NH_4Cl$ solution (100 mL), and extracted with ethyl acetate (2×100 mL). The organic layers were combined and dried over $MgSO_4$, filtered, and the filtrate concentrated to a white solid which was recrystallized from hexane/ethyl acetate to give 5.42 grams of 3-(4-trifluoromethylphenyl)pent-2-enoic acid methyl ester intermediate (85% yield).

To a solution of 3-(4-trifluoromethylphenyl)pent-2-enoic acid methyl ester in THF/MeOH was added a solution of sodium hydroxide in $H_2O$ (15 mL). The resulting solution was stirred at room temperature for 12 hours, and acetic acid (3 grams) was added. The solution was then concentrated to an oil. The oil was dissolved in ethyl acetate (100 mL) and washed with $H_2O$ (3×100 mL). The ethyl acetate extracts were combined and dried over $MgSO_4$, filtered, and concentrated to a semi-solid which was then dissolved in MeOH/THF (2:1, 50 mL) and shaken with 10% Pd/C under 50 psi of hydrogen pressure for 24 hours. TLC showed that the reaction was incomplete. Additional 10% Pd/C was added (500 mg) and the suspension was shaken for an additional 24 hours. The suspension was then filtered and the filtrate concentrated to a semi-solid (4.97 g). The solid was dissolved in $CH_2Cl_2$ (30 mL) and the resulting solution cooled to 0° C. To this solution was added oxalyl chloride followed by one drop of DMF from a 9-inch disposable pipette. The solution was stirred for 8 hours and then concentrated to a solid which was dissolved in additional $CH_2Cl_2$ (30 mL). The solution was again concentrated to a semi-solid which was dissolved in additional $CH_2Cl_2$ (50 mL), and the resulting solution added dropwise to a chilled (5° C.) and mechanically stirred solution of $NH_4OH$ (10 mL) over approximately five minutes. The suspension was then concentrated to a gummy/aqueous mixture which was extracted with ethyl acetate (2×100 mL). The ethyl acetate extracts were combined and dried over $MgSO_4$, filtered, and the filtrate concentrated to a crude amber-solid which was adsorbed onto silica gel (50 g) using $CH_2Cl_2$/THF.

The solid was then chromatographed on silica gel (EtOAc/hexane) to give 2.25 grams of off-white solid (37% yield). This material was determined to be 100% pure by LC/MS. H-NMR gave signals consistent with the product's structure and indicated greater than 98% purity.

Example 22

Preparation of Compound AW
[3-(4-Isopropylphenyl)butyramide]

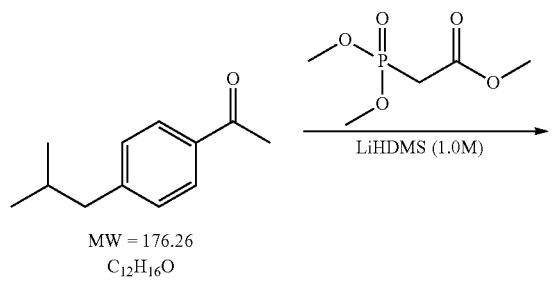

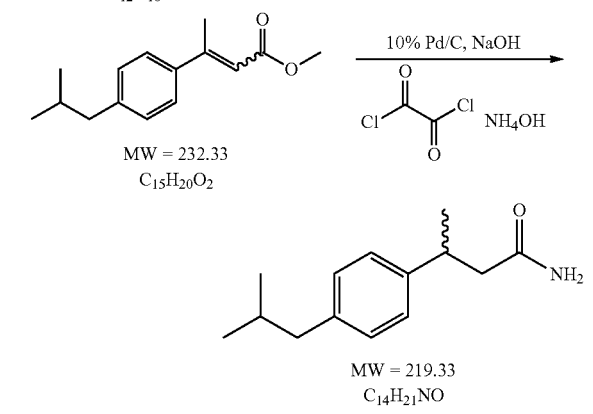

To a chilled (0° C.) solution of lithium bis(trimethylsilyl) amide (1.0 M, 56 mL) was dropwise added a solution of trimethylphosphonoacetate, keeping the temperature below 10° C. The solution was then allowed to warm to room temperature and stirred for an additional five minutes after which a solution of p-isobutylacetophenone in THF (25 mL) was added in one portion. The solution was slowly heated to 65° C. and allowed to reflux for thirty hours. The solution was cooled to room temperature then diluted with a 10% NH$_4$Cl solution (100 mL), and extracted with ethyl acetate (2×100 mL). The organic layers were combined and dried over MgSO$_4$, filtered, and filtrate concentrated to a white solid which was recrystallized from hexane/ethyl acetate to give 5.93 grams of 3-(4-isobutylphenyl)but-2-enoic acid methyl ester intermediate (89.9% yield).

To a solution of 3-(4-isobutylphenyl)but-2-enoic acid methyl ester in THF/MeOH was added a solution of sodium hydroxide in H$_2$O (15 mL). The resulting solution was stirred at room temperature for 12 hours and acetic acid (3 grams) was added. The solution was then concentrated to an oil. The oil was dissolved in ethyl acetate (150 mL) and washed with H$_2$O (3×100 mL). The ethyl acetate extracts were combined and dried over MgSO$_4$, filtered, and concentrated to a solid (4.98 g) which was then dissolved in MeOH/THF (2:1, 50 mL) and shaken with 10% Pd/C under 50 psi of hydrogen pressure for 24 hours. TLC showed that the reaction was incomplete. Additional 10% Pd/C was added (500 mg) and the suspension was shaken for an additional 24 hours. The suspension was then filtered and the filtrate concentrated to a solid (4.75 g). The solid was dissolved in CH$_2$Cl$_2$ (30 mL) and the resulting solution cooled to 0° C. To this solution was added oxalyl chloride followed by one drop of DMF from a 9-inch disposable pipette. The solution was stirred for six hours and then concentrated to a solid which was dissolved in additional CH$_2$Cl$_2$ (30 mL). The solution was again concentrated to a semi-solid which was dissolved in additional CH$_2$Cl$_2$ (50 mL), and the resulting solution added dropwise to a chilled (5° C.) and mechanically stirred solution of NH$_4$OH (10 mL) over approximately five minutes. The suspension was then concentrated to a solid/aqueous mixture which was extracted with ethyl acetate (2×100 mL). The ethyl acetate extracts were combined and dried over MgSO$_4$, filtered, and the filtrate concentrated to a crude solid which was adsorbed onto silica gel (50 g) using CH$_2$Cl$_2$/THF. The solid was then chromatographed on silica gel (EtOAc/Hexane) to give 2.5 grams of off-white solid (40% yield). This material was determined to be 100% pure by LC/MS. $^1$H-NMR gave signals consistent with the product's structure and indicated greater than 98% purity.

Example 23

Preparation of Compound AE
[3-(6-Methoxynaphthalen-2-yl)-butyramide]

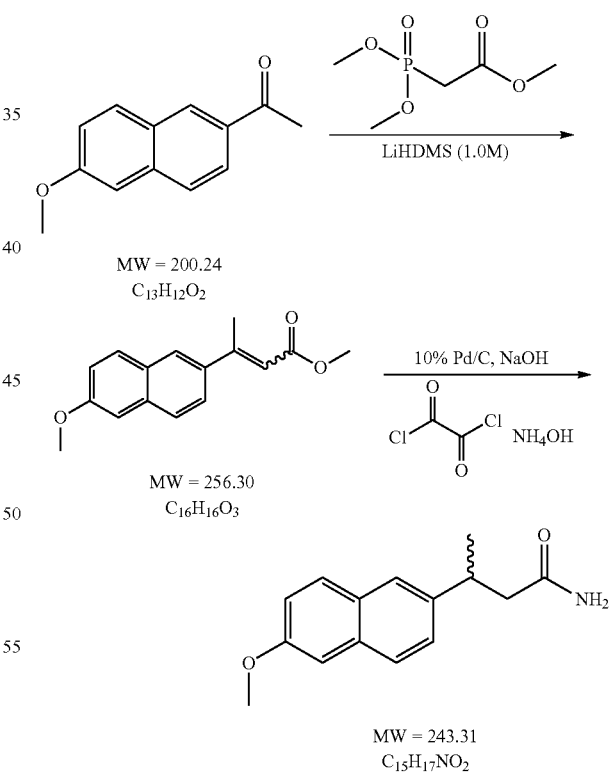

To a chilled (0° C.) solution of lithium bis(trimethylsilyl) amide (1.0 M, 50 mL) was dropwise added a solution of trimethylphosphonoacetate, keeping the temperature below 10° C. The solution was then allowed to warm to room temperature and stirred for an additional ten minutes after which a solution of 2-acetyl-6-methoxynaphthalene in THF (20 mL)

was added in one portion. The solution was slowly heated to 50° C. for fourteen hours. The solution was cooled to room temperature then diluted with a 10% NH₄Cl solution (100 mL), and extracted with ethyl acetate (2×100 mL). The organic layers were combined and dried over MgSO₄, filtered, and filtrate concentrated to a white solid which was recrystallized from hexane/ethyl acetate to give 5.88 grams of 3-(6-methoxynaphthalen-2-yl)but-2-enoic acid methyl ester intermediate (92% yield).

To a solution of 3-(6-methoxynaphthalen-2-yl)but-2-enoic acid methyl ester in THF/MeOH was added a solution of sodium hydroxide in H₂O (15 mL). The resulting solution was stirred at room temperature for 12 hours and acetic acid (3 grams) was added. The solution was then concentrated to a solid residue. The solid was dissolved in ethyl acetate (150 mL) and washed with H₂O (3×100 mL). The ethyl acetate extracts were combined and dried over MgSO₄, filtered, and concentrated to a solid which was then dissolved in MeOH/THF (2:1, 50 mL) and shaken with 10% Pd/C under 50 psi of hydrogen pressure for 24 hours. TLC showed that the reaction was incomplete. Additional 10% Pd/C was added (500 mg) and the suspension was shaken for an additional 24 hours. The suspension was then filtered and the filtrate concentrated to a semi-solid (4.97 g). The solid was dissolved in CH₂Cl₂ (30 mL) and the resulting solution cooled to 0° C. To this solution was added oxalyl chloride followed by one drop of DMF from a 9-inch disposable pipette. The solution was stirred for six hours and then concentrated to a solid which was dissolved in additional CH₂Cl₂ (30 mL). The solution was again concentrated to a semi-solid which was dissolved in additional CH₂Cl₂ (50 mL), and the resulting solution added dropwise to a chilled (5° C.) and mechanically stirred solution of NH₄OH (10 mL) over approximately fifteen minutes. The suspension was then concentrated to a gummy/aqueous mixture which was extracted with ethyl acetate (2×100 mL). The ethyl acetate extracts were combined and dried over MgSO₄, filtered, and the filtrate concentrated to a crude solid which was adsorbed onto silica gel (50 g) using CH₂Cl₂/THF. The solid was then chromatographed on silica gel (EtOAc/hexane) to give 1.87 grams of off-white solid (32% yield). This material was determined to be 100% pure by LC/MS. H-NMR gave signals consistent with the product's structure and indicated greater than 98% purity.

Example 24

Preparation of Compound AX
[3-(2-Fluoro-biphenyl-4-yl)butyramide]

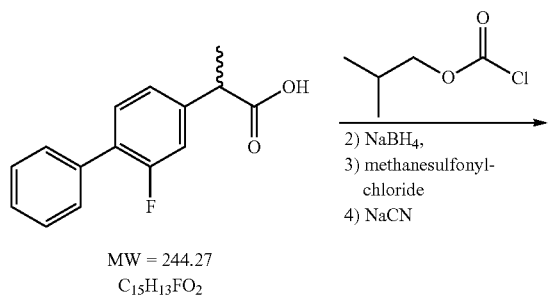

MW = 244.27
C₁₅H₁₃FO₂

2) NaBH₄,
3) methanesulfonyl-
   chloride
4) NaCN

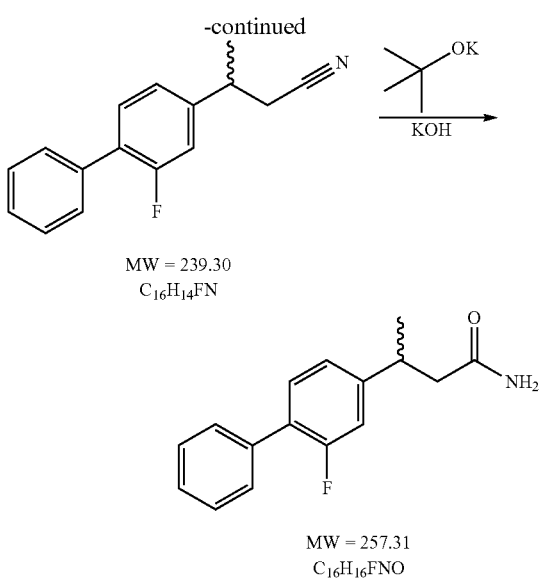

MW = 239.30
C₁₆H₁₄FN

MW = 257.31
C₁₆H₁₆FNO

To a chilled (0° C.) solution of 2-(2-fluoro-biphenyl-4-yl) propionic acid in THF was added isobutyl chloroformate followed by dropwise addition of TEA. The resulting white slurry was allowed to stir for 1 hour and then diluted with THF (50 mL) and filtered. The filter cake was washed with additional THF (50 mL) and the filtrate was concentrated to approximately 50 mL using a rotary evaporator. The concentrated filtrate was then stirred at −20° C. and a solution of NaBH₄ in H₂O (20 mL) was dropwise added over a period of 15 minutes. The resulting suspension was stirred for 2 hours at 0° C., diluted with water (200 mL), and extracted with ethyl acetate (2×100 mL). The ethyl acetate layers were combined and washed with 1.0 N HCl solution (100 mL) followed by a 5% bicarbonate solution wash (100 mL). The ethyl acetate solution was then concentrated to an oily residue of 2-(2-fluoro-biphenyl-4-yl)propanol (4.47 g, 95% yield).

To a chilled (0° C.) solution of 2-(2-fluoro-biphenyl-4-yl) propanol in CH₂Cl₂ was added methanesulfonyl chloride followed by dropwise addition of TEA. The resulting white slurry was allowed to stir for 1 hour and then diluted with H₂O (200 mL). The suspension was extracted with CH₂Cl₂ (2×100 mL). The CH₂Cl₂ layers were combined and with water (2×100 mL) and a 5% NH₄OH solution (100 mL). The CH₂Cl₂ layer was then washed with additional H₂O (200 mL) and dried over MgSO₄. The CH₂Cl₂ layer was concentrated to an oily residue which was dissolved in anhydrous DMF (50 mL). This solution was treated with NaCN and stirred at 60° C. for 14 hours. The TLC indicated one major less polar eluting product (relative to mesylate) and several minor less polar eluting products relative to both the major and mesylate products. The reaction was cooled to room temperature and diluted with H₂O (100 mL). The solution was extracted with ethyl acetate (2×100 mL), dried over MgSO₄, and concentrated to an oily residue which was chromatographed on silica gel (90% Hex, 10% EtOAc) to give 3-(2-fluoro-biphenyl-4-yl)butyronitrile as an oil which slowly solidified on standing at room temperature (2.05 g, 49% yield).

To a solution of 3-(2-fluoro-biphenyl-4-yl)butyronitrile in tert-butyl alcohol was added 1.87 g of finely powdered potassium hydroxide. The resulting suspension was stirred and heated to 70° C. for 2.5 hours and cooled to room temperature. The reaction suspension was diluted with 1.0 N HCl solution (100 mL) and extracted with ethyl acetate (2×100 mL). The ethyl acetate extracts were combined and washed with 5% bicarbonate solution (100 mL) and then with H$_2$O (100 mL). The organics were then dried over MgSO$_4$, and concentrated to a white solid which was re-crystallized several times with EtOAc/Hex to give white flaky prisms (1.62 g, 75% yield).

Example 25

Preparation of Compound AY
[3-(4-Morpholin-4-yl-phenyl)-butyramide]

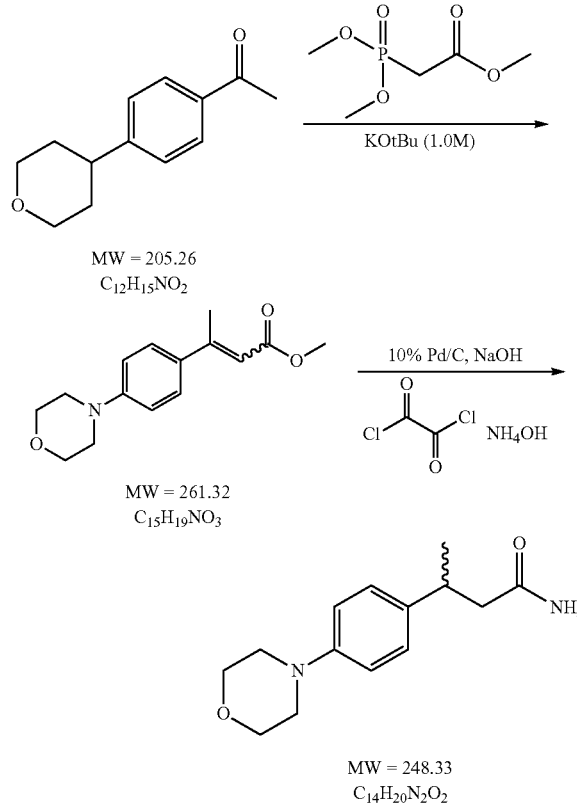

To a chilled (0° C.) solution of potassium tert-butoxide (1.0 M, 37.1 mL) was dropwise added a solution of trimethylphosphonoacetate, keeping the temperature below 25° C. The solution was then allowed to warm to room temperature and stirred for an additional five minutes, after which a solution of 4-morpholinoacetophenone in THF (20 mL) was added in one portion. The solution was slowly heated to 60° C. for 36 hours. The solution was cooled to room temperature, then diluted with a 1.0N HCl solution (100 mL), and extracted with ethyl acetate (2×100 mL). The organic layers were combined and dried over MgSO$_4$, filtered, and the filtrate concentrated to a white solid which was recrystallized from hexane/ethyl acetate to give 3.33 grams of 3-(4-morpholinophenyl)but-2-enoic acid methyl ester intermediate (69.9% yield).

To a solution of 3-(4-morpholinophenyl)but-2-enoic acid methyl ester in THF/MeOH (1:1) was added a solution of sodium hydroxide in H$_2$O (15 mL). The resulting solution was stirred at room temperature for 15 hours and acetic acid (3 grams) was added. The pH of the solution was measured at 6.5. The solution was then concentrated to an oil. The oil was dissolved in ethyl acetate (150 mL) and washed with H$_2$O (3×100 mL). The ethyl acetate extracts were combined and dried over MgSO$_4$, filtered, and concentrated to an amorphous solid which was then dissolved in MeOH (50 mL) and shaken with 10% Pd/C under 50 psi of hydrogen pressure for 8 hours. TLC showed that the reaction was complete. The suspension was then filtered and the filtrate concentrated to a semi-solid (2.77 g). The semi-solid was dissolved in CH$_2$Cl$_2$ (30 mL) and the resulting solution cooled to 0° C. To this solution was added oxalyl chloride followed by one drop of DMF from a 9-inch disposable pipette. The solution was stirred for four hours and then concentrated to a solid which was dissolved in additional CH$_2$Cl$_2$ (30 mL). The solution was again concentrated to a semi-solid which was dissolved in additional CH$_2$Cl$_2$ (50 mL), and the resulting solution added dropwise to a chilled (5° C.) and mechanically stirred solution of NH$_4$OH (15 mL) over approximately five minutes. The solution was then concentrated to a solid/aqueous mixture which was extracted with ethyl acetate (2×100 mL). The ethyl acetate extracts were combined and dried over MgSO$_4$, filtered, and the filtrate concentrated to a crude solid which was adsorbed onto silica gel (50 g) using CH$_2$Cl$_2$/THF. The solid was then chromatographed on silica gel (EtOAc/hexane) to give 2.1 grams of beige plates (46% yield). This material was determined to be 100% pure by LC/MS. H-NMR gave signals consistent with the product's structure and indicated greater than 98% purity.

Example 26

Preparation of Compound Q-1 [trans-2-Phenylcyclopropane-carboxylic acid-((S)-1-carbamoyl-propyl)amide]

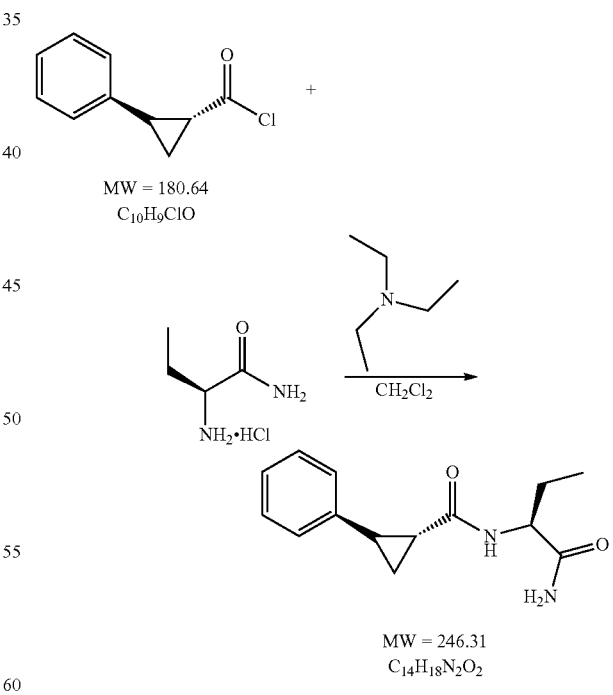

A solution of trans-2-phenyl-cyclopropanecarbonylchloride in CH$_2$Cl$_2$ (20 mL) was added dropwise into a solution of L-2-aminobutanamide hydrochloride (1.61 g, 11.6 mmol) and triethylamine (3.36 g, 33.2 mmol) in CH$_2$Cl$_2$ (60 ml) at zero degree Celsius. The reaction mixture stirred at room temperature under nitrogen overnight.

The reaction mixture was evaporated under reduced pressure and resulting residue re-dissolved in ethyl acetate/water mixture. The mixture was transferred into a separatory funnel using $H_2O$ (50 mL) and ethyl acetate (80 mL). The mixture was equilibrated and the aqueous phase was removed. The organic layer was washed with 1.0M HCl (20 mL), $H_2O$ (90 mL) and brine (120 mL) consecutively. The organic layer was dried over anhydrous magnesium sulfate, filtered, and excess solvent was removed under reduced pressure. The resulting orange-brown solid was purified using a Biotage SP4 System (Column Si 40+M 90:10, $CH_2Cl_2$/MeOH), which afforded 0.365 g of white powder (24% yield). This material was determined to be 100% pure by GC/MS. $^1$H-NMR gave signals consistent with the product's structure and indicated greater than 98% purity.

Figure 4A:
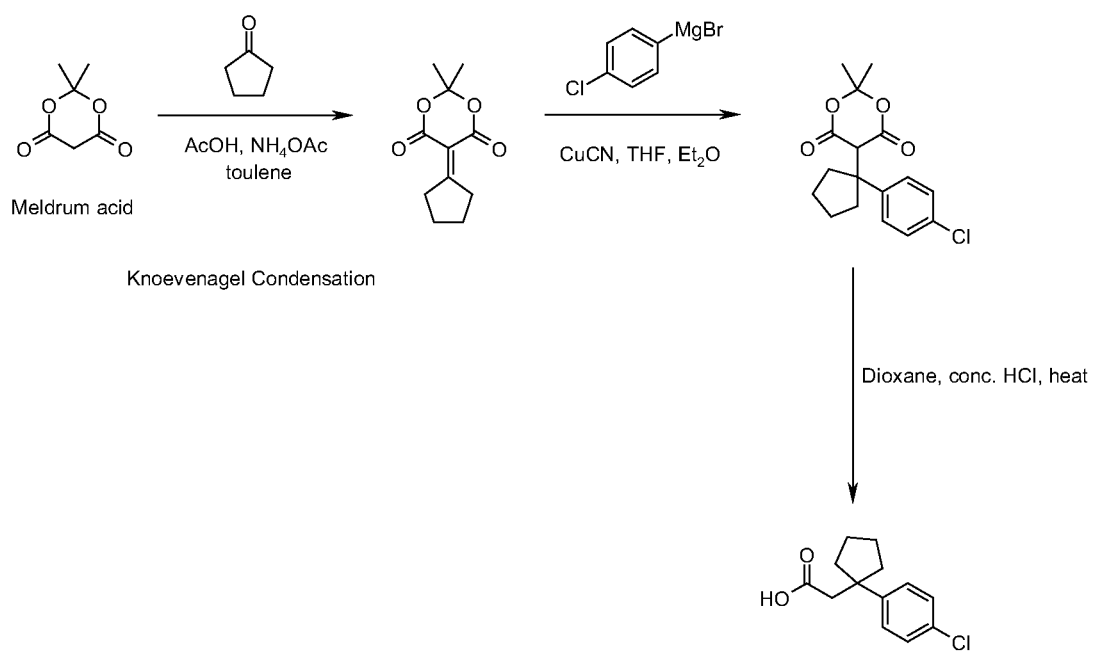
FIGS. 4A-4O illustrate examples of the syntheses of various compounds and key intermediates.
Figure 4B:
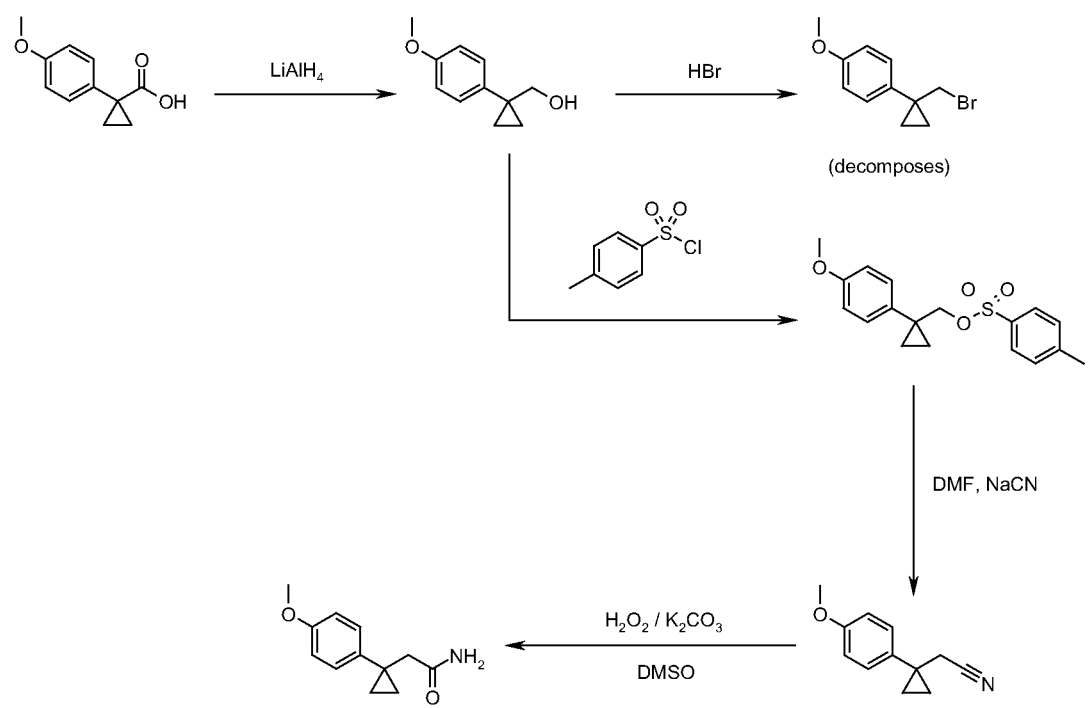
Figure 4C:
Figure 4D:
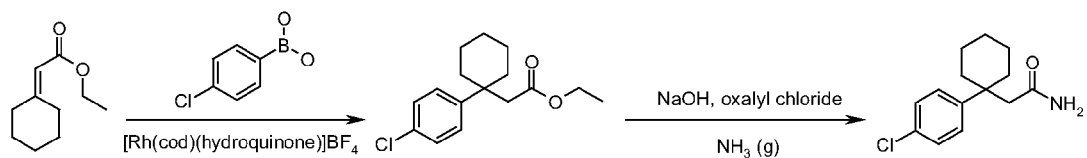
Figure 4E:
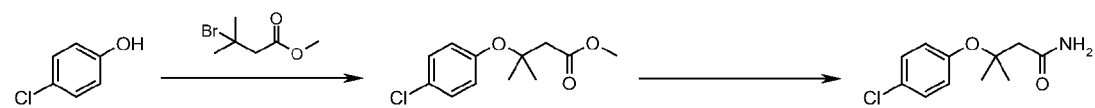
Figure 4F:
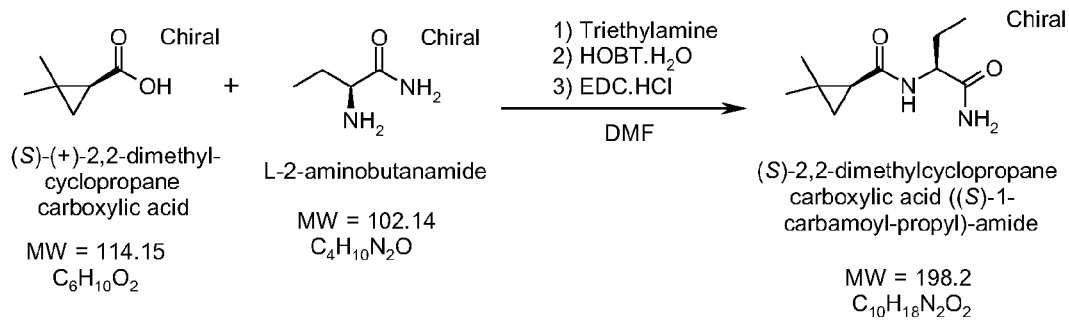
Figure 4G:
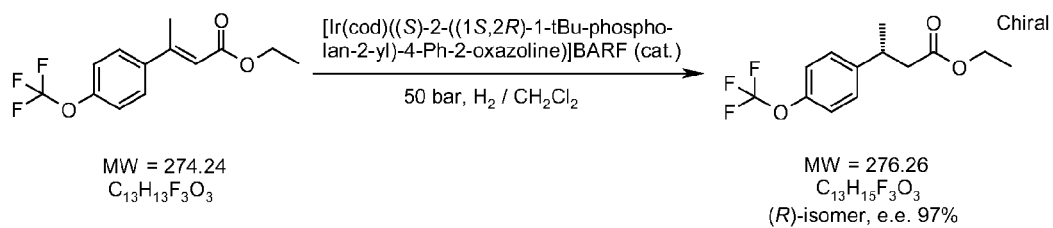
Figure 4H:
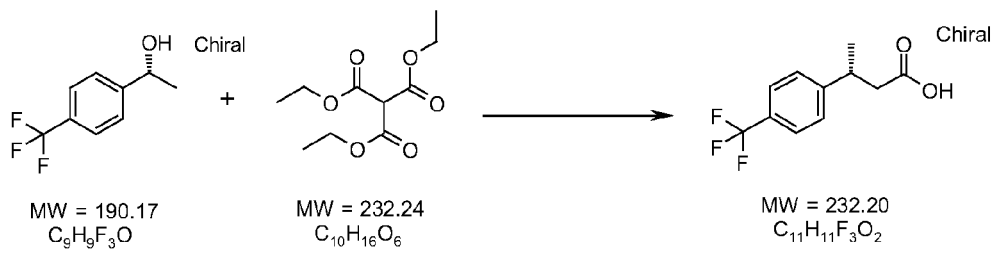
Figure 4I:
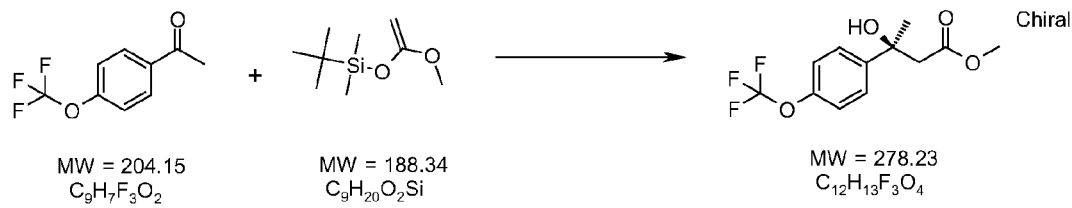
Figure 4J:
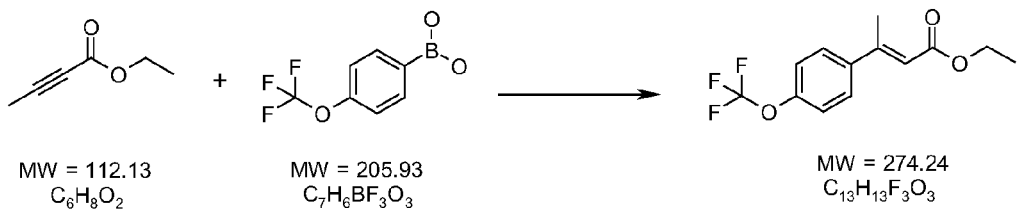
Figure 4K:
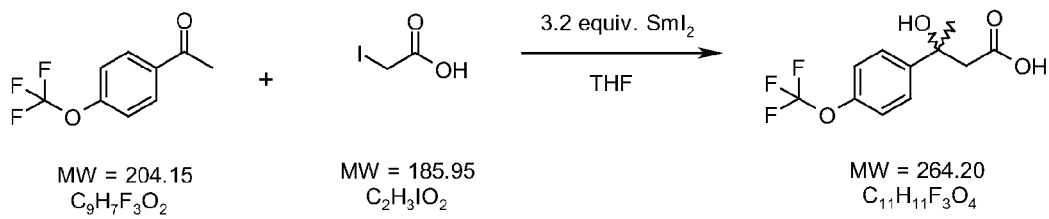
Figure 4L:
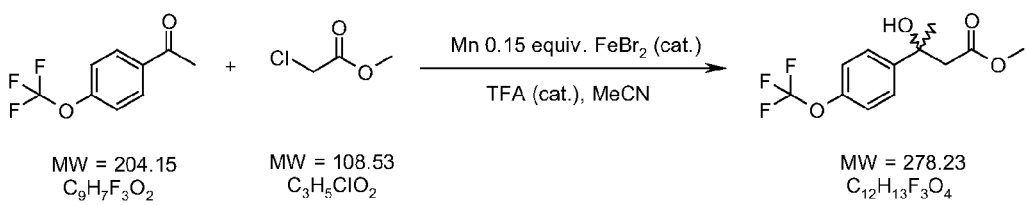
Figure 4M:
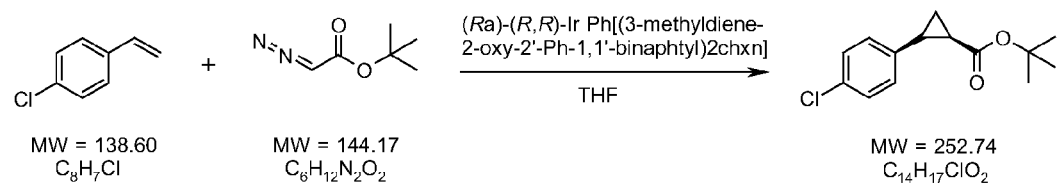
Figure 4N:
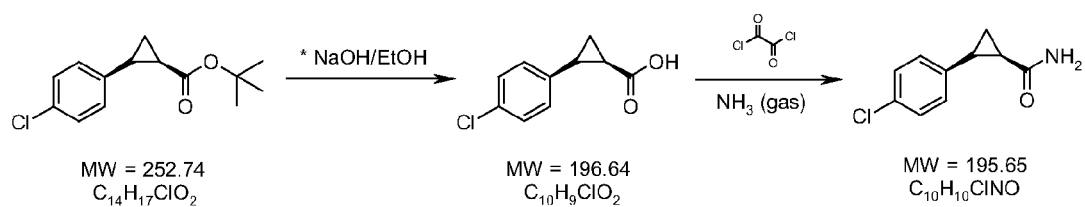
Figure 4O:
Figure 5:
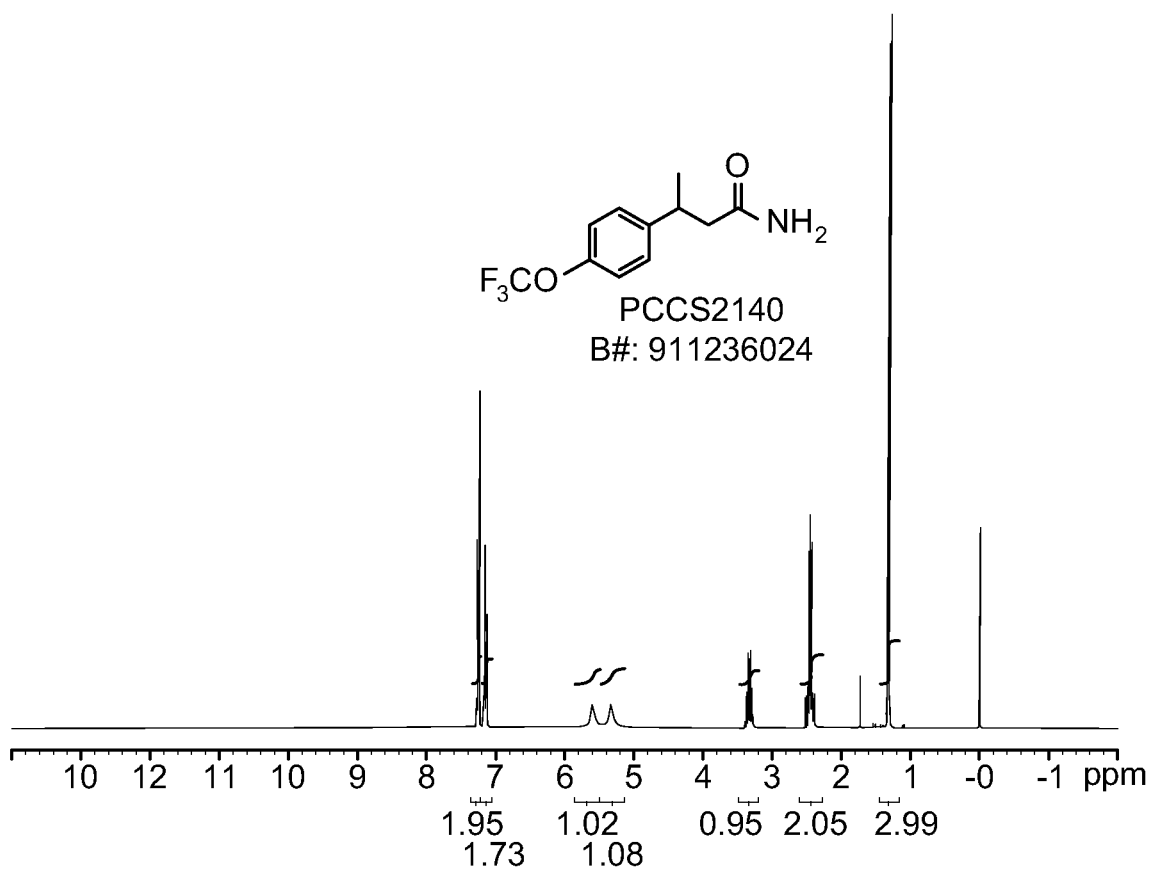
FIG. 5 shows a $^1$H-NMR spectrum of compound H.
Figure 6A:
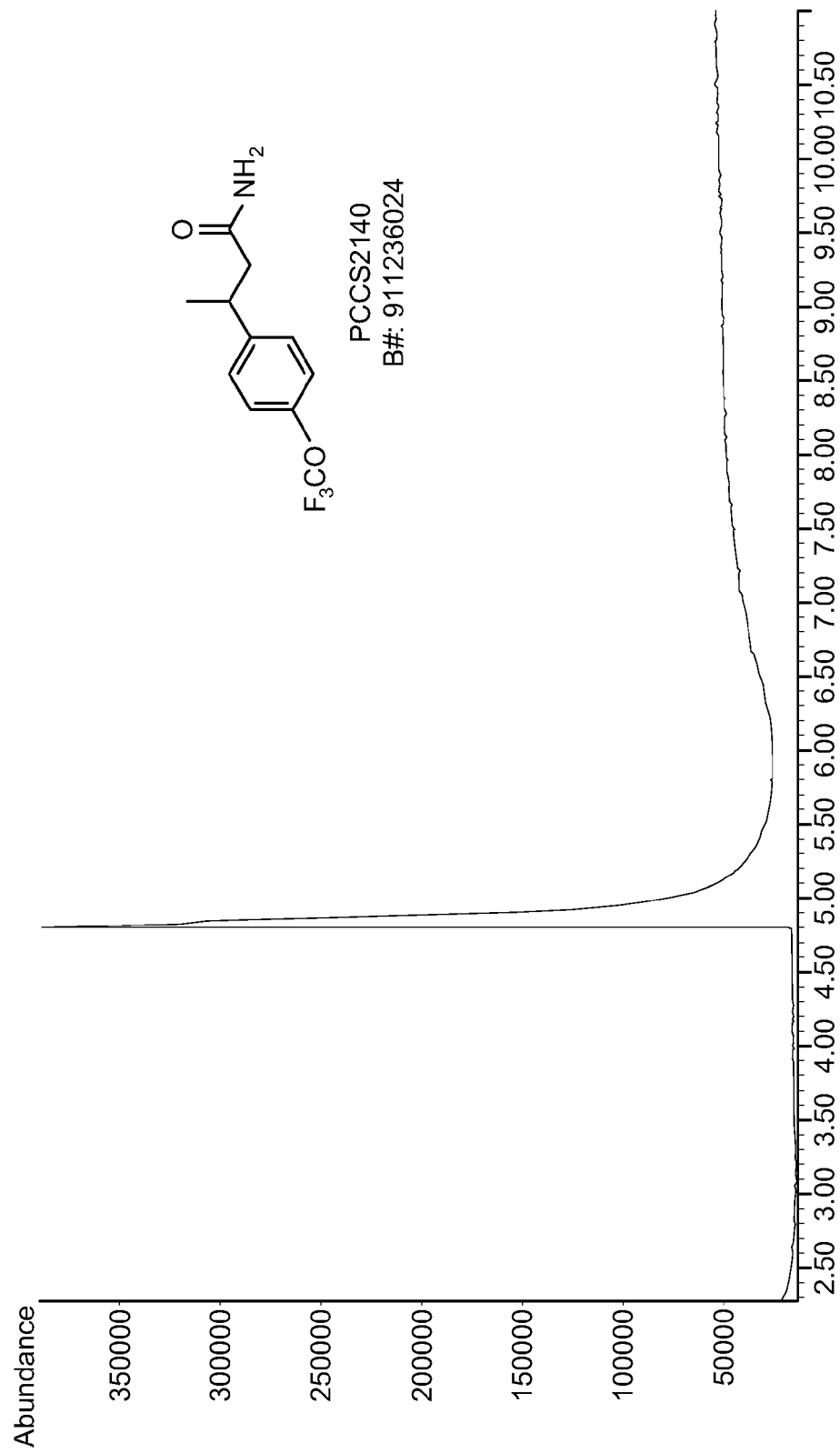
FIG. 6A shows an LC/MS Total Ion Chromatogram of compound H.
Figure 6B:
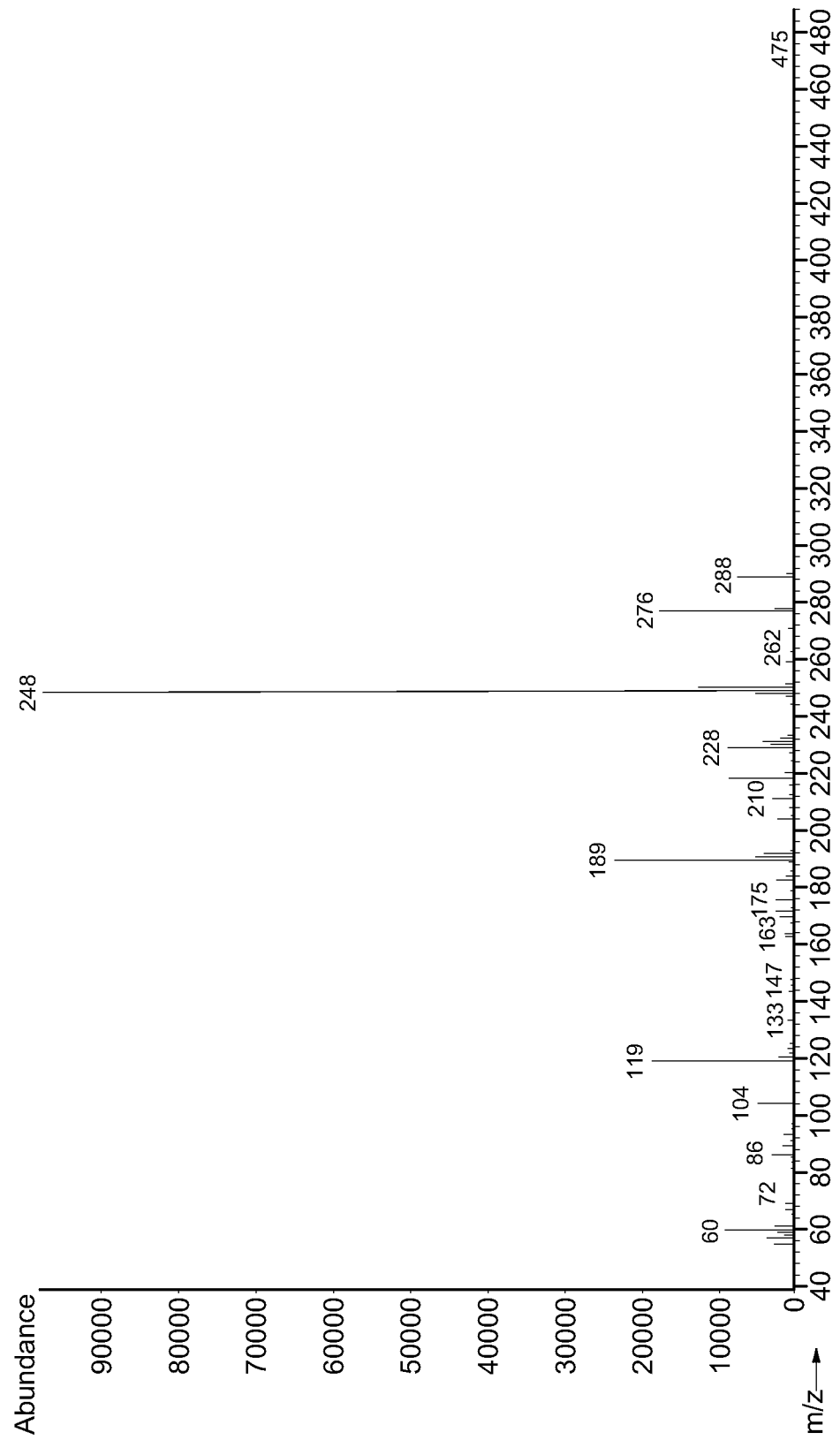
FIG. 6B shows a mass spectrum of compound H.
Figure 7A:
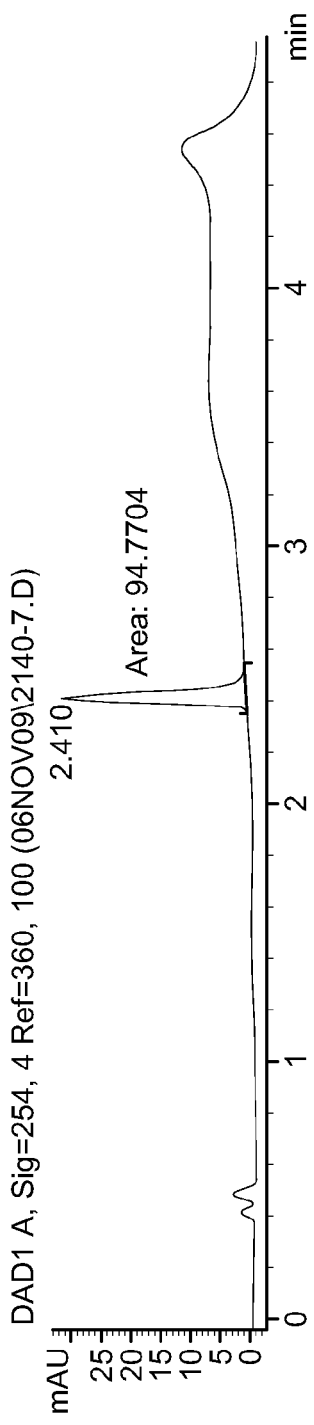
FIGS. 7A-C illustrate LC chromatograms of compound H with UV monitoring at 254, 215, and 215 nm, respectively.
Figure 7B:
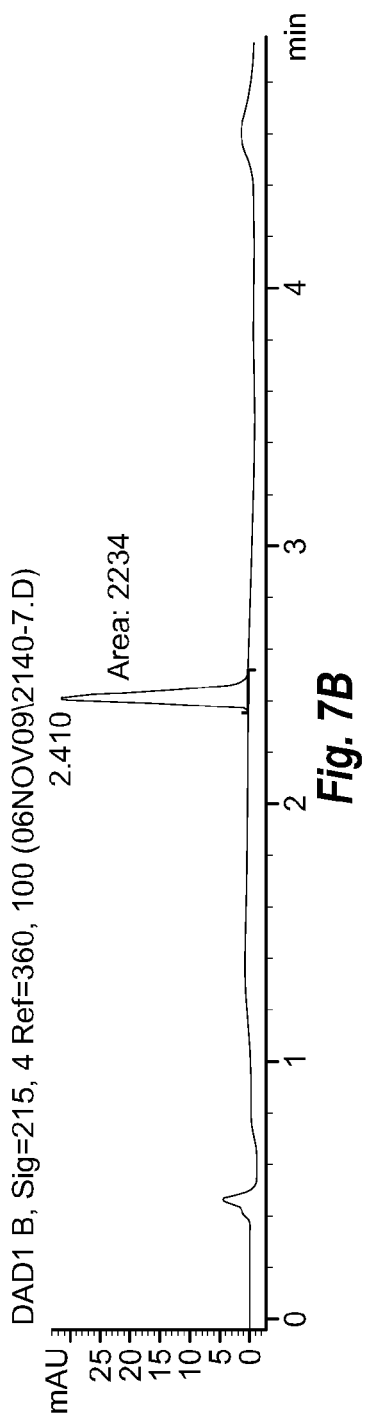
Figure 7C:
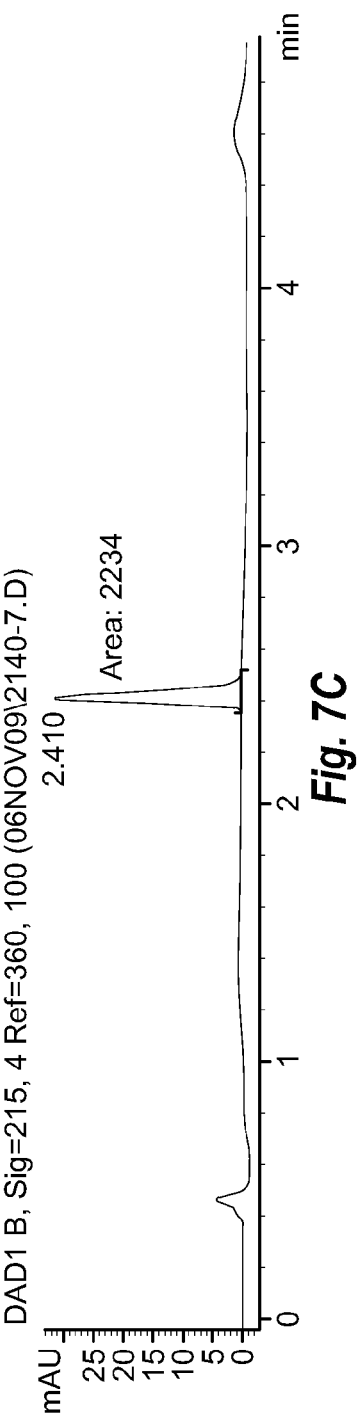
Figure 8:
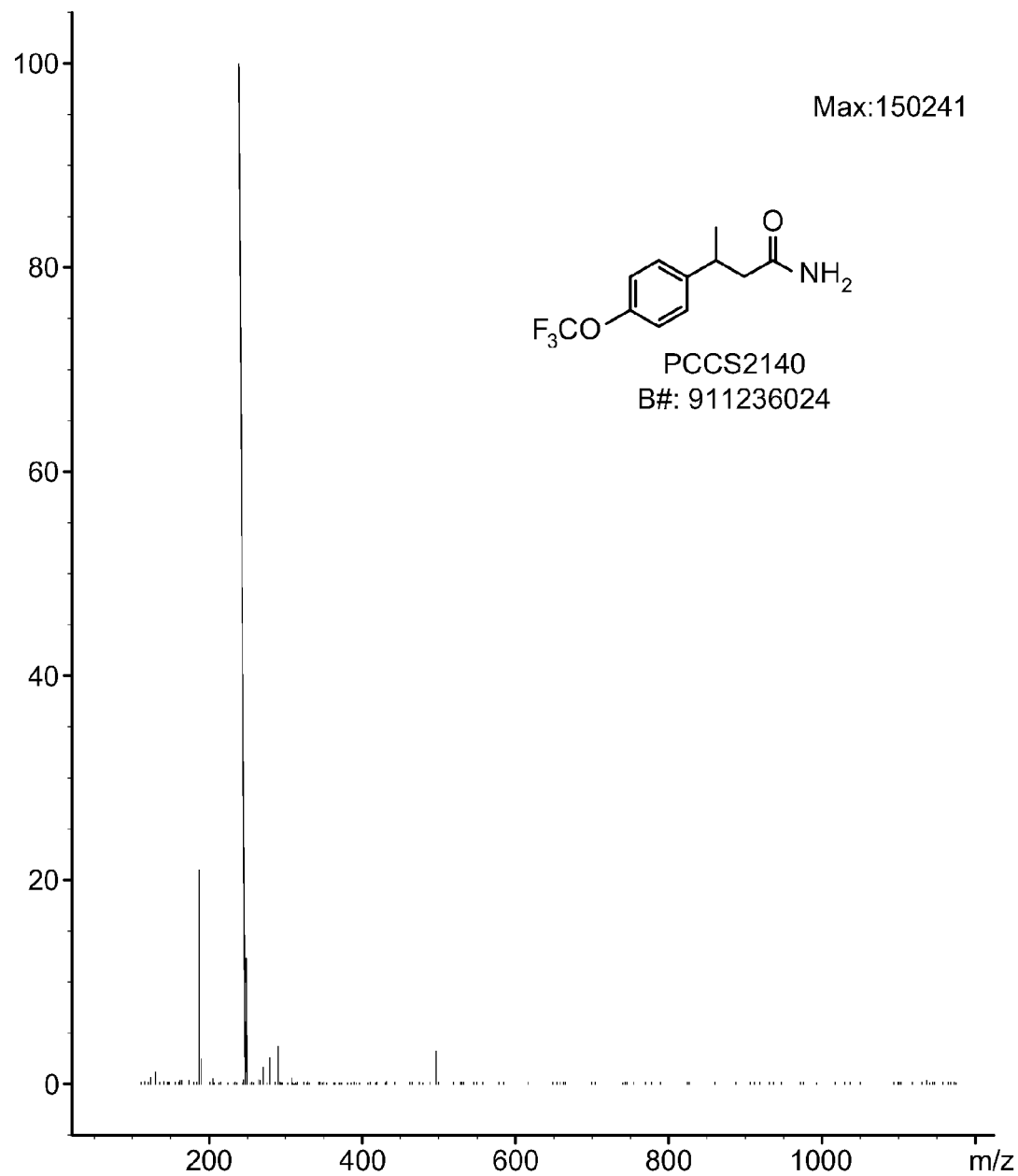
FIG. 8 shows another mass spectrum of compound H.

FIGS. 4A-4O illustrate additional examples of the syntheses of various compounds and key intermediates (Schemes 1-15), drawn from the literature of synthetic organic chemistry, from which skilled artisans will be able to envision the preparation of various additional compounds of the present invention.

Example 27

Synthesis of Racemic Compound H overnight. The mixture was cooled to ambient temperature and transferred to a 5 L round-bottom flask. The solvent was removed by rotovap and the residue was diluted with hexanes (2.0 L). The solid was removed by filtration and washed with hexanes (1.0 L). The filtrate was concentrated and purified by silica gel chromatography to afford the compound 3 (94.2 g, 82.5%) as a colorless oil.

Preparation of Compound 4:

To compound 3 (130.0 g, 0.474 mol) in ethanol (350 mL) was added 6N NaOH (474 mL, 1.9 mol, 6.0 eq.). The reaction mixture was stirred at room temperature overnight. The mixture was then concentrated to dryness under reduced pressure. The resulting residue was re-dissolved in water (500 mL) and extracted by ether (2×300 mL). The aqueous phase was neutralized by 3N HCl to pH~2 and extracted by ethyl acetate (2×500 mL). The combined organic layers were dried over $MgSO_4$, filtered and concentrated to dryness to give the compound 4 (106.0 g, 90.8%) as a white solid.

Preparation of Compound 5:

To the compound 4 (106.0 g, 0.431 mol) in THF (600 mL) was added Pd/C (10%, 5.0 g). The mixture was subjected to hydrogenation at ambient pressure overnight and filtered through a Celite plug. The filtrate was concentrated to afford compound 5 (107.0 g, 100%) as a colorless oil which solidified upon standing at room temperature.

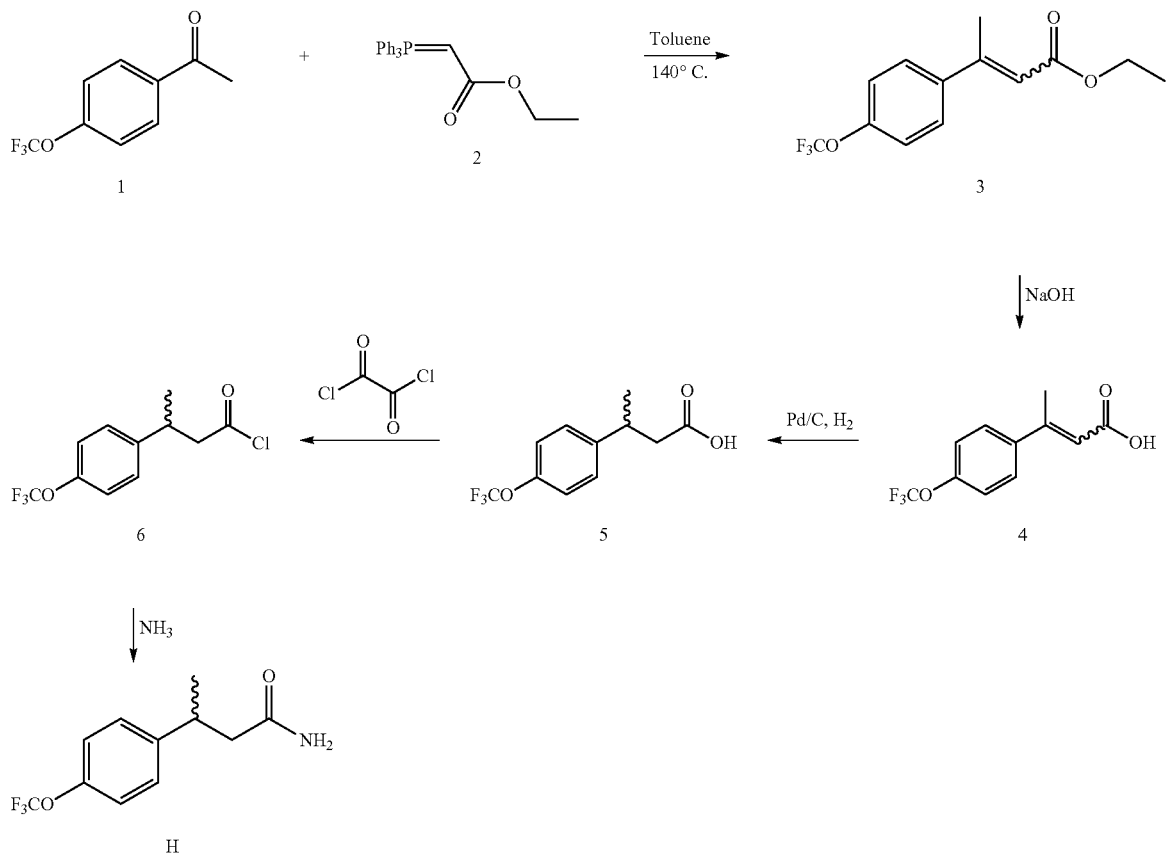

Preparation of Compound 3:

To a one-gallon autoclave was added 4'-trifluoromethoxyacetophenone (85.0 g, 0.416 mol), (carbethoxymethylene)triphenylphosphorane (159.6 g, 0.458 mol, 1.1 eq.) and toluene (1.0 L). The mixture was heated to 140° C. and stirred Preparation of Compound 6:

To a solution of compound 5 (70.0 g, 0.282 mol) in DCM (1.0 L), was added DMF (1.0 mL) and oxalyl chloride (34.9 mL, 0.40 mol, 1.47 eq.) at 0° C. The reaction mixture was stirred at room temperature overnight. The solvent and excess reagent were removed under reduced pressure. The resulting residue was azeotroped by toluene (300 mL) to give compound 6 (crude) which was used for the next step without further purification.

Preparation of Compound H:

To a solution of compound 6 (crude) in anhydrous THF (1.2 L) was bubbled ammonia (gas) for 30 min. at 5° C. The reaction mixture was stirred at room temperature overnight. The solid was filtered and washed with THF (500 mL). The filtrate was evaporated under reduced pressure. The resulting solid was dissolved in ethyl acetate (2.0 L), washed with water (500 mL), 1.0M HCl (300 mL), sat. NaHCO$_3$ (500 mL), and brine (500 mL), and dried over MgSO$_4$. After filtration and evaporation of the solvent, the obtained solid was triturated with ether/hexanes (1:1, 300 mL) and dried in a vacuum oven (40° C./2 h) to give compound 7 (61.0 g, 87.5%) as a white solid: mp=84-86° C.

Analytical data for compound H [300 MHz proton nuclear magnetic resonance (NMR) spectrum, gas chromatography/mass spectrometry (GC/MS), liquid chromatography/mass selective detection (LC/MSD), and mass spectrum (MS)] are shown in FIGS. 5-8.

Example 28

Baseline Separation of Racemic Compound H into its Enantiomers, Compounds BX and BY, by Means of Chiral Liquid Chromatography (LC)

Separation

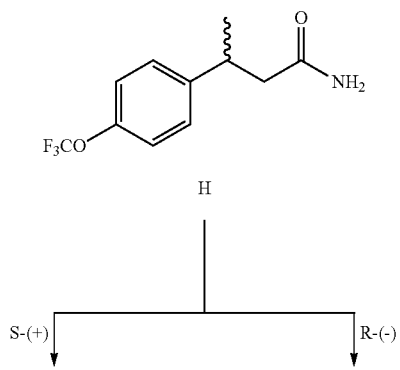

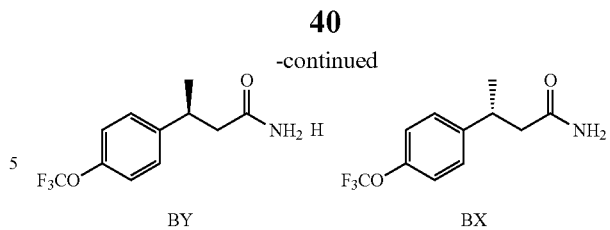

The objective of this work was to chirally separate a total of 37.7 g of racemic compound 7 to obtain an approximate 85% yield of both (each) of its enantiomers. The enantiomeric purity requirement was >98% e.e. for both of the enantiomers.

Preparative Chromatographic Conditions

The operating conditions used for the separation process were as follows:

Column: R, R-WhelkO-1 10 μm, 5 cm id×25 cm L

Mobile Phase Hex/MTBE/EtOH/TFA=50/45/5/0.1

Flow rate: 60 ml/min

Temperature: 25° C.

UV detection: 210 nm

Separation and Isolation

Feed solubility was 15 g/L in the mobile phase. Stirring and heating were required to dissolve the feed. The feed solution was filtered through a 0.2-μm filter before use. A total of 37.7 g of racemate was processed. Injection volume was 20 ml every 14.5 min.

The fractions collected from the chromatographic process were concentrated using bench-top rotary evaporators at 40° C. and 50 mbar. The products did not crystallize and remain liquidly after overnight under vacuum. The weight of each peak was well over the expected amount. It was decided to wash the products with water to remove the extra weight, most likely resulting from the TFA used in the mobile phase. Each peak was dissolved in dichloromethane and washed twice with water. The weights which remained after drying in a vacuum overnight at 40° C. were still slightly higher than expected. Subsequently the products were dissolved in ethyl acetate and then washed twice with sodium bicarbonate before drying under vacuum overnight. The results of the separation are shown below in Table 2.

TABLE 2

| Peak # | 1 | 2 |
|---|---|---|
| Optical Rotation | (−) | (+) |
| Structure | Chiral structure | Chiral structure |
| Compound # | BX | BY |
| Name | R-(−)-3-(4-Trifluoromethoxy-phenyl) butyramide | S-(+)-3-(4-Trifluoromethoxy-phenyl) butyramide |
| Retention Time (min) | 12.96 | 15.89 |
| Weight (g) | 15.8 | 17.3 |
| % e.e. | 99.7 | 99.1 |
| Yield | 83.8% | 91.8% |

*Angew. Chem. Int. Ed.* 2007, 46, 2623-2626

Figure 9:
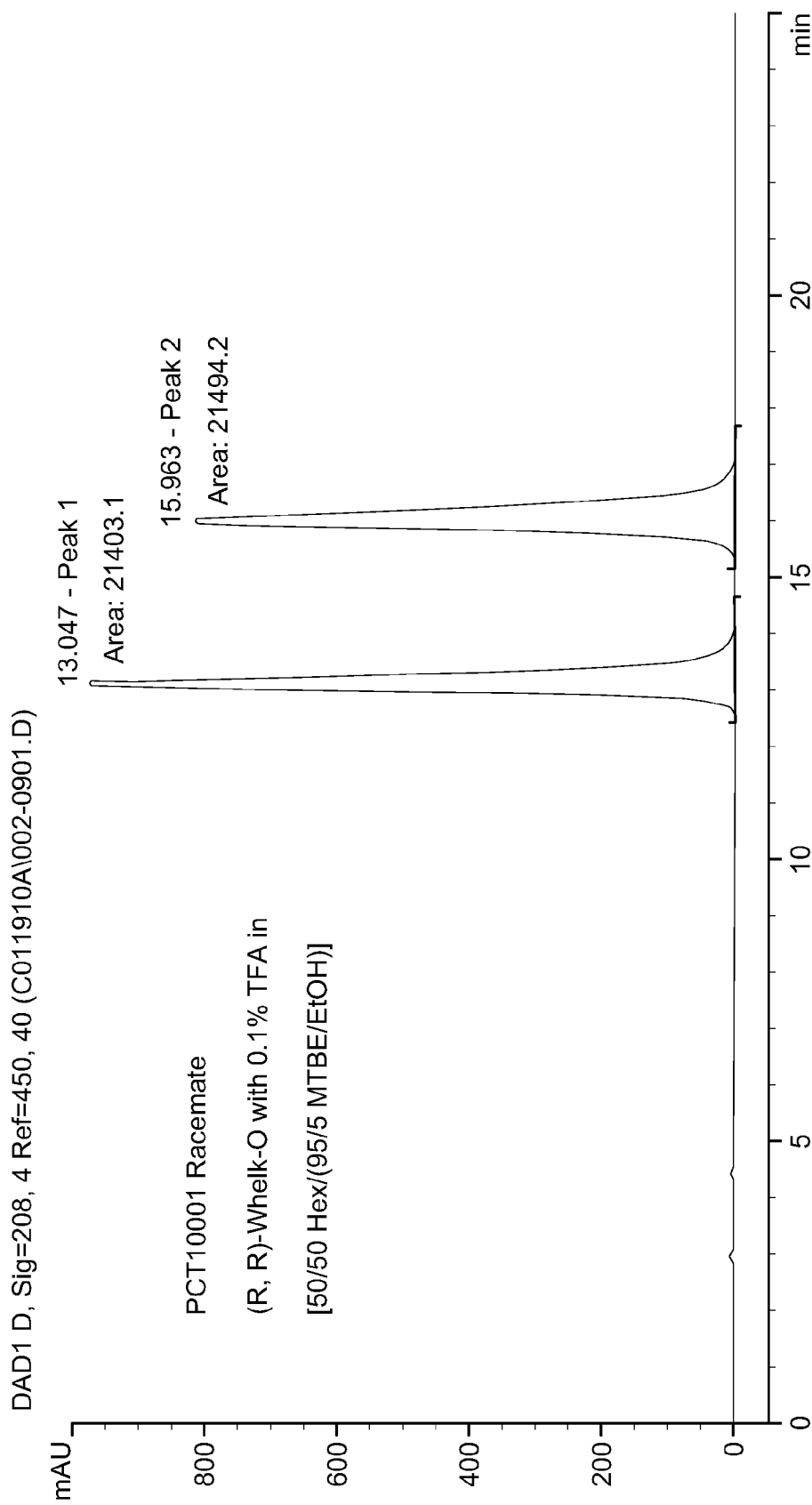
FIG. 9 shows a chiral liquid chromatographic separation of the two enantiomers of compound H, with UV monitoring at 208 nm.
Figure 10:
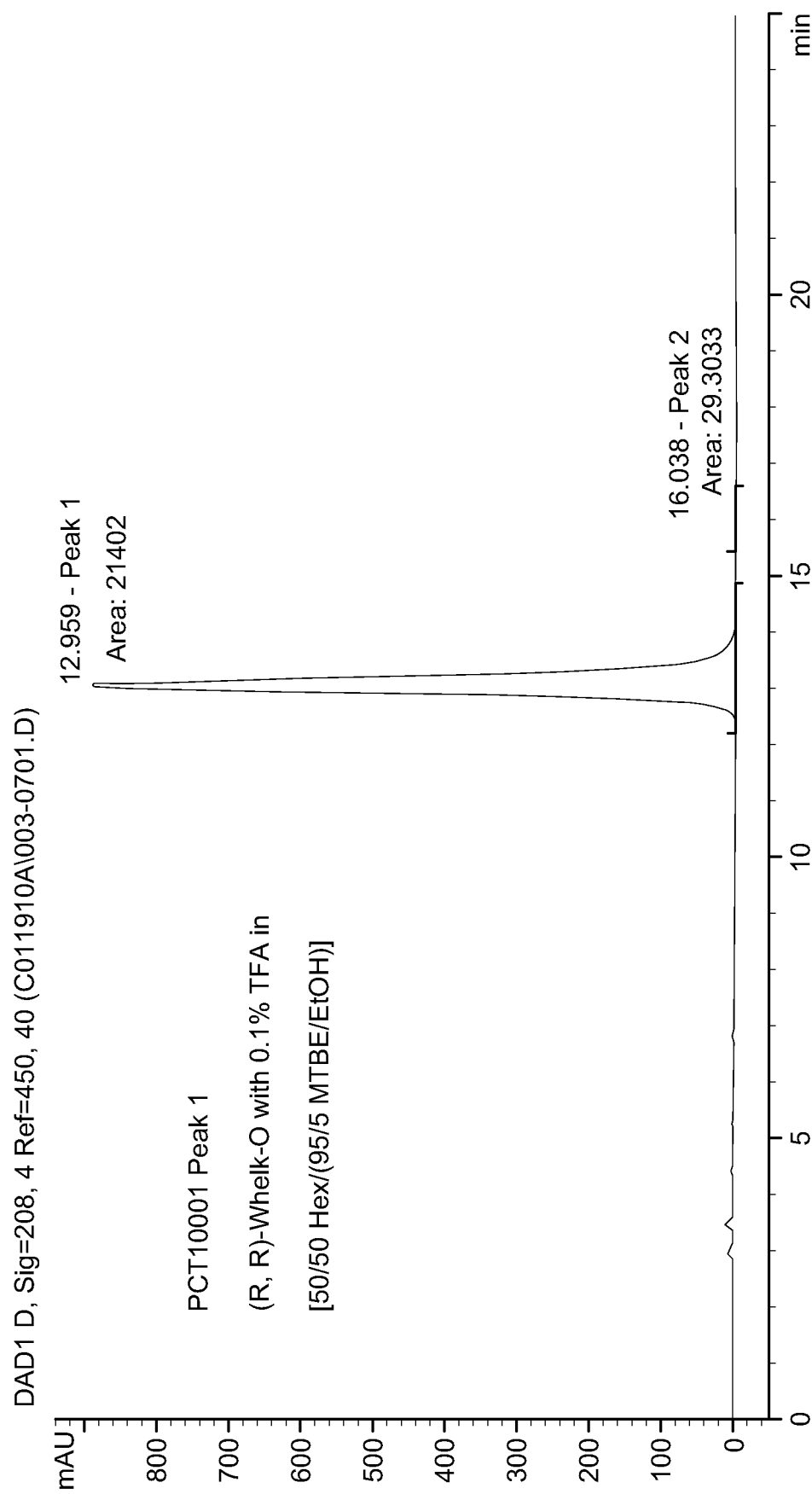
FIGS. 10 and 11 show liquid chromatograms of the separated individual enantiomers of compound H, with UV monitoring at 208 nm.
Figure 11:
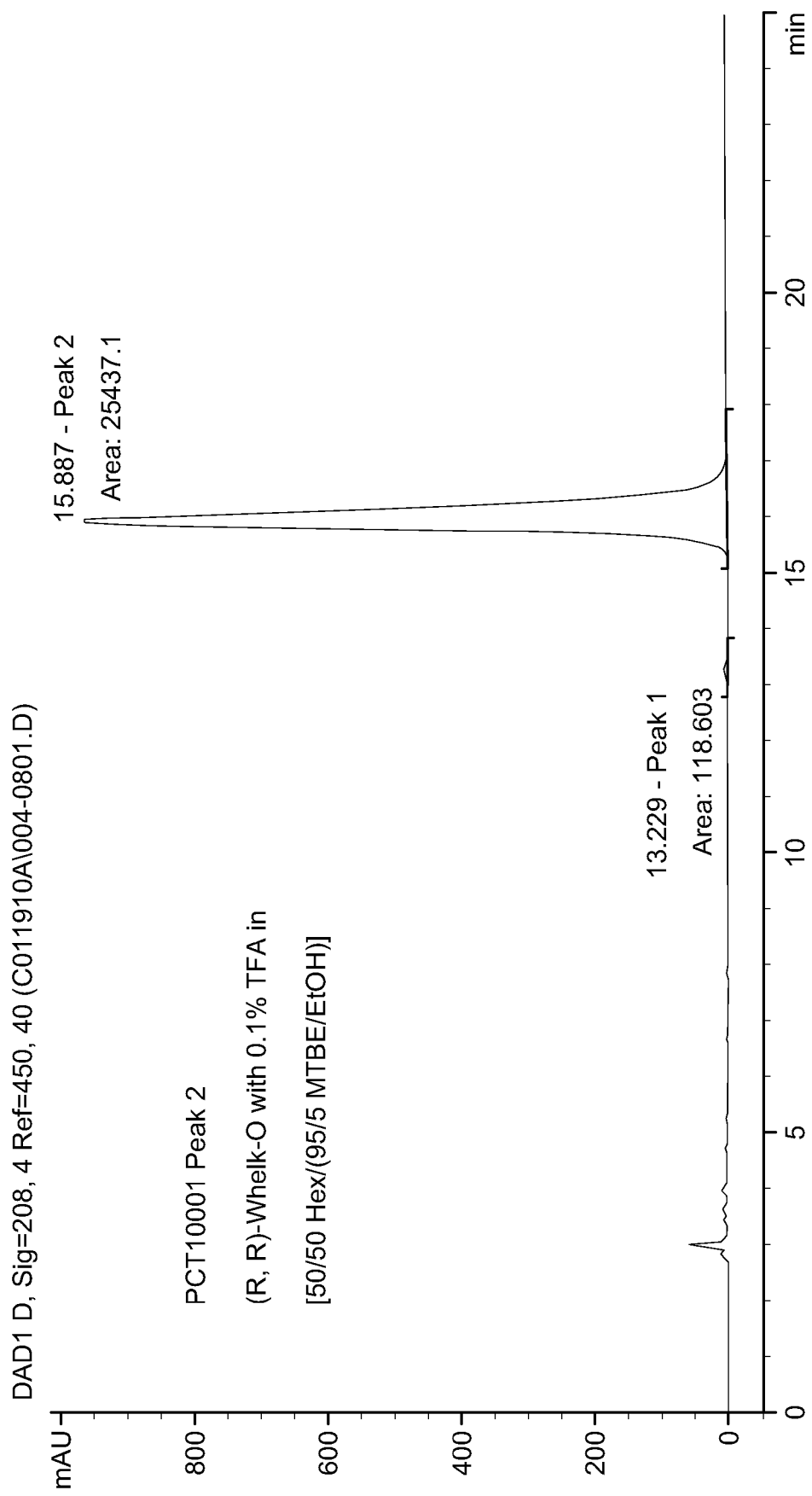

The enantiomeric excesses were determined by chiral HPLC [(R,R)-Whelk-O-1 10 μm, 5 cm id×25 cm L]. The absolute configuration was assigned by comparison of the retention times of the two enantiomers with previously reported data. Results are shown below in FIGS. 9-11. For a recent review of hydrogenation of olefins with P,N ligands, see:

(a) Pfaltz, A.; Blankenstein, J.; Hilgraf, R.; Hormann, E.; McIntyre, S.; Menges, F.; Schonleber, M.; Smidt, S. P.; Wustenberg, B.; Zimmermann, N. *Adv. Synth. Catal.* 2003, 345, 33 and references cited therein.
(b) Kallstrom, K.; Hedberg, C.; Brandt, P.; Bayer, A.; Andersson, P. G. *J. Am. Chem. Soc.* 2004, 126, 14308-14309.
(c) Durry, W. J., III; Zimmerman, N.; Keenan, M.; Hayashi, M.; Kaiser, S.; Goddard, R.; Pfaltz, A. *Angew. Chem., Int. Ed. Engl.* 2004, 43, 70.
(d) Bunlaksananusorn, T.; Polborn, K.; Knochel, P. *Angew. Chem., Int. Ed. Engl.* 2003, 42, 3941.
(e) Xu, G.; Gilbertson, S. R. *Tetrahedron Lett.* 2003, 44, 953.
(f) Brauer, D. J.; Kottsieper, K. W.; Boβenbach, S.; Stelzer, O. *Eur. J. Inorg. Chem.* 2003, 1748.
(g) Tang, W.; Wang, W.; Zhang, X. *Angew. Chem., Int. Ed.* 2003, 42, 943.
(h) Menges, F.; Neuburger, M.; Pfaltz, A. *Org. Lett.* 2002, 4, 4713.
(i) Hou, D.; Reibenspies, J.; Colacot, T. J.; Burgess, K. *Chem. Eur. J.* 2001, 7, 5391.

The entireties of which are incorporated herein by reference.

Example 29

Synthesis of Compound BX (I.E., the R Enantiomer of Compound H) by an Alternative Separation Route

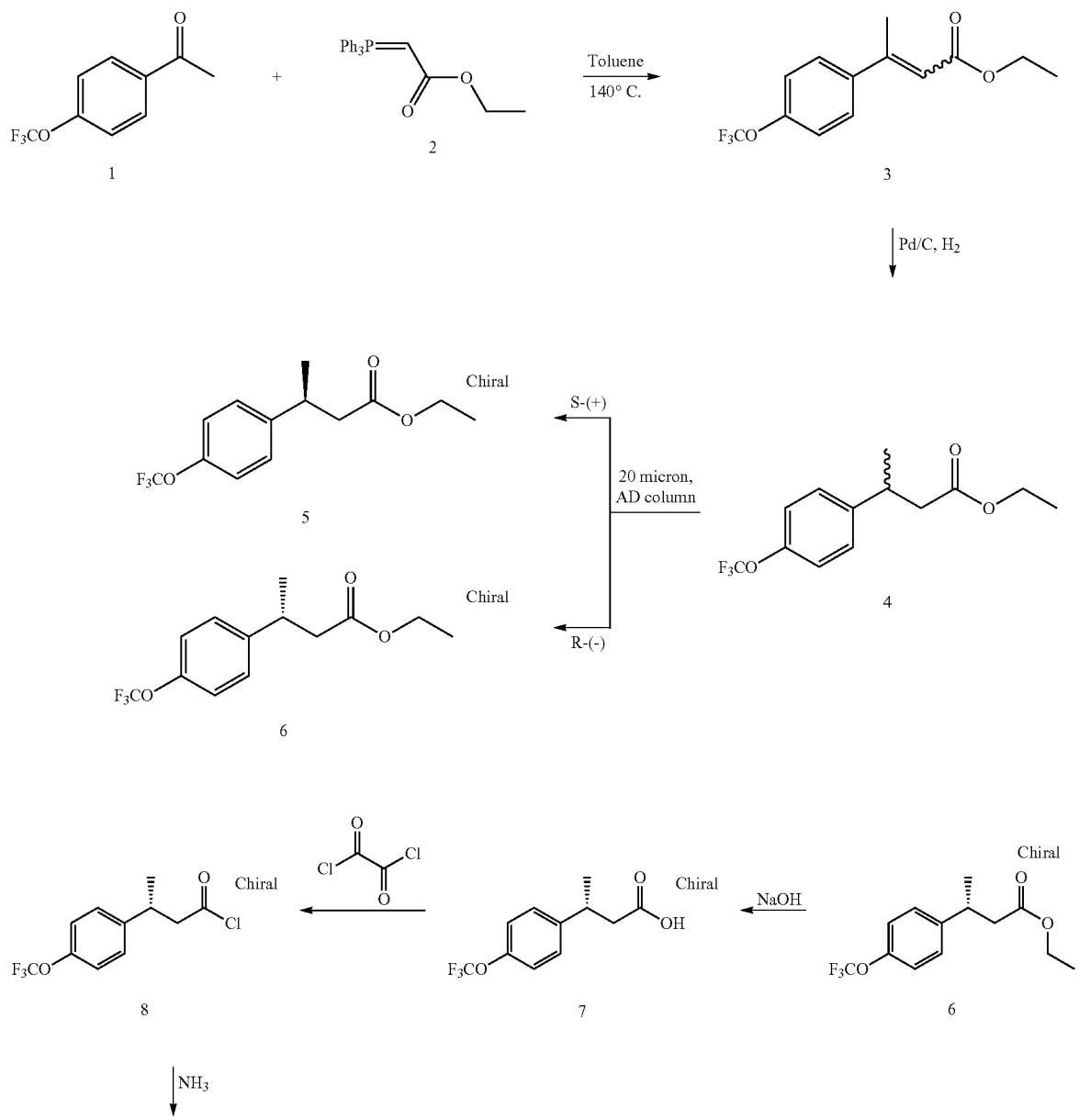

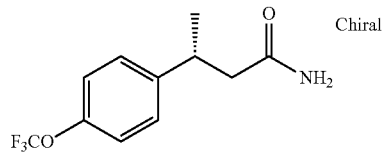

BX

Examples 30-41
Preparation of Various Primary Amides

TABLE 3

| Example No. | Formula | Weight (g) | % Yield | Product Chemical Name | Corresponding Carboxylic Acid |
|---|---|---|---|---|---|
| 30 | AL | 1.76 | 74 | 3-Cyclopropyl-3-ρ-tolyl-propionamide | 3-cyclopropyl-3-(4-methylphenyl) propanoic acid |
| 31 | AQ | 1.69 | 81 | 3-(4-Fluoro-phenyl)-4-methyl-pentanoic acid-amide | 3-(4-Fluorophenyl)-4-methyl pentanoic acid |
| 32 | AR | 0.420 | 18 | 3-(4-Chloro-phenyl)-4-methyl-pentanoic-acid-amide | 3-(4-Chlorophenyl)-4-methyl pentanoic acid |
| 33 | Y | 1.12 | 56 | 3-Cyclopropyl-3-(4-fluoro-phenyl)propionamide | 3-Cyclopropyl-3-(4-fluorophenyl) propanoic acid |
| 34 | X | 1.42 | 71 | 3-(4-Chloro-phenyl)-3-cyclopropyl-propionamide | 3-Cyclopropyl-3-(4-chlorophenyl)propanoic acid |
| 35 | AO | 1.25 | 62 | 3-Cyclopropyl-3-(4-fluoro-3-methyl phenyl)-propionamide | 3-Cyclopropyl-3-(4-fluoro-3-methylphenyl)propanoic acid |
| 36 | AM | 1.68 | 80 | 3-Cyclopropyl-3-(4-methoxy-phenyl)-propionamide | 3-cyclopropyl-3-(4-methoxyphenyl)propanoic acid |
| 37 | AP | 1.62 | 74 | 3-Cyclopropyl-3-(2,3dihydro-benzo[1,4]dioxin-6-yl)propionamide | (5-methyl-2,3-dihydro-1-benzofuran-2-yl)acetic acid |
| 38 | AN | 1.57 | 72 | 3-Cyclopropyl-3-(4-methoxy-3-methyl-phenyl)propionamide | 3-cyclopropyl-3-(4-methoxy-3-methylphenyl)propanoic acid |
| 39 | AS | 2.15 | 98 | 3-(4-Methoxy-3-methyl-phenyl)-4-methylpentanoic acid amide | 3-(4-methoxy-3-methylphenyl)-4-methylpentanoic acid |
| 40 | AB | 1.30 | 30 | 3-(4-Methoxy-phenyl)-pentanoicacid amide | 3-(4-Methoxy-phenyl)-pentanoic acid |
| 41 | BB | 1.73 | 86 | 2,2-Diphenyl-cyclopropanecarboxylicacid amide | 2,2-Diphenyl-cyclopropanecarboxylic acid |

The primary amides listed in Table 3 (Examples 30-41) were prepared from the corresponding carboxylic acids using the method of Example 1.

Examples 42-59
Preparation of Various Secondary and Tertiary Amides

The secondary and tertiary amides listed in the Table 4 (Examples 42-59) were prepared using the corresponding acid chlorides and amines by the method of Example 2. In certain cases (i.e., when the amines used were amino acids), the amine hydrochlorides were first rendered as free bases using excess tri-ethylamine.

TABLE 4

| Example No. | Formula | Weight (g) | % Yield | Product Chemical Name | Corresponding Amine |
|---|---|---|---|---|---|
| 42 | BC | 0.793 | 88 | N-Methyl-3-(4-trifluoromethoxyphenyl)-butyramide | Methylamine |

TABLE 4-continued

| Example No. | Formula | Weight (g) | % Yield | Product Chemical Name | Corresponding Amine |
|---|---|---|---|---|---|
| 43 | BD | 0.783 | 90 | N,N-Dimethyl-3-(4-trifluoromethoxy-phenyl)-butyramide | N,N-dimethylamine |
| 44 | BE | 0.685 | 85 | N-Ethyl-N-methyl-3-(4-trifluoromethoxy-phenyl)-butyramide | N-Ethylmethylamine |
| 45 | BF | 0.910 | 52 | N-Ethyl-3-(4-trifluoromethoxy-phenyl)-butyramide | Ethylamine |
| 46 | BG | 0.280 | 13 | 1-Pyrrolidin-1-yl-3-(4-trifluoromethoxy-phenyl)-butan-1-one | Pyrrolidine |
| 47 | BH | 1.30 | 64 | 1-Piperidin-1-yl-3-(4-trifluoromethoxy-phenyl)-butan-1-one | Piperidine |
| 48 | BI | 0.705 | 32 | 1-Morpholin-4-yl-3-(4-trifluoromethoxy-phenyl)-butan-1-one | Morpholine |
| 49 | BJ | 0.900 | 36 | 1-(4-Methyl-piperazin-1-yl)-3-(4-trifluoromethoxy-phenyl)-butan-1-one hydrochloride | 1-Methylpiperazine |
| 50 | BK | 1.89 | 87 | 1-(4-Methyl-piperidin-1-yl)-3-(4-trifluoromethoxy-phenyl)-butan-1-one | 4-Methylpiperidine |
| 51 | BL | 1.50 | 61 | N-(2-Methoxy-ethyl)-3-(4-trifluoromethoxy-phenyl)-butyramide | 2-Methoxyethylamine |
| 52 | BM | 1.20 | 50 | N-(3-Methoxy-propyl)-3-(4-trifluoromethoxy-phenyl)-butyramide | 3-Methoxypropylamine |
| 53 | BN | 1.50 | 63 | 1-[3-(4-Trifluoromethoxy-phenyl)-butyryl]-piperidine-4carboxylic acidamide | 4-Piperidinecarboxamide |
| 54 | BO | 0.870 | 83 | (S)-4-Methyl-2-[3-(4-trifluoromethoxy-phenyl)-butyrylamino]-pentanoic acid amide | L-Leucinamide |
| 55 | BP | 0.760 | 39 | (R)-4-Methyl-2-[3-(4-trifluoromethoxy-phenyl)-butyrylamino]-pentanoic acid amide | D-Leucinamide |
| 56 | BQ | 0.430 | 23 | (S)-1-[3-(4-Trifluoromethoxy-phenyl)-butyryl]-pyrrolidine-2-carboxylicacid amide | S-Prolinamide |
| 57 | BR | 0.507 | 27 | N-((S)-1-Carbamoyl-propyl)-3-(4-trifluoromethoxy-phenyl)-butyramide | L-2-Aminobutanamide |
| 58 | BS | 0.460 | 24 | N-((S)-1-Carbamoyl-ethyl)-3-(4-trifluoromethoxy-phenyl)-butyramide | L-Alaninamide |
| 59 | BT | 1.16 | 46 | 1-[3-(4-Trifluoromethoxy-phenyl)-butyryl]-piperidine-3-carboxylic acid amide | Nipecotamide |

Example 60

Preparation of Compounds BU (3-[2-(trifluoromethoxy)-phenyl]butyramide), BV (3-[4-chlorophenyl]butyramide), and BW (3-[3,4-dichloro-phenyl]butyramide)

Compounds BU, BV, and BW were prepared from the corresponding acetophenones by the same method used in the preparation of Examples 4-14, except that for the preparation of BV and BW, platinum was used as the catalyst instead of palladium, and ambient pressure was used (instead of higher pressure, e.g., 45 psi).

Example 61

Synthesis of Compound CC (3-hydroxy-3-(4(trifluoromethoxy)-phenyl)butanamide)

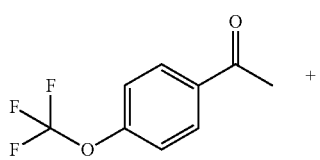

+

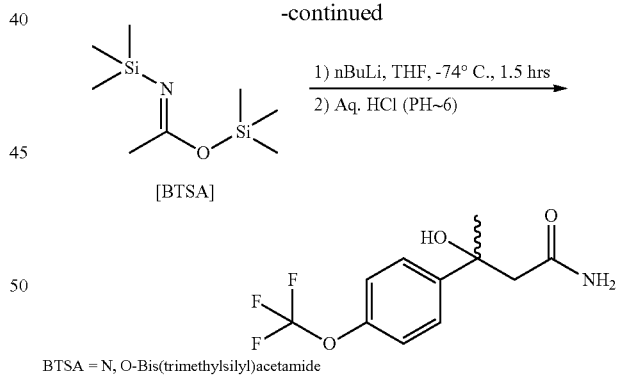

BTSA = N, O-Bis(trimethylsilyl)acetamide

Figure 12:
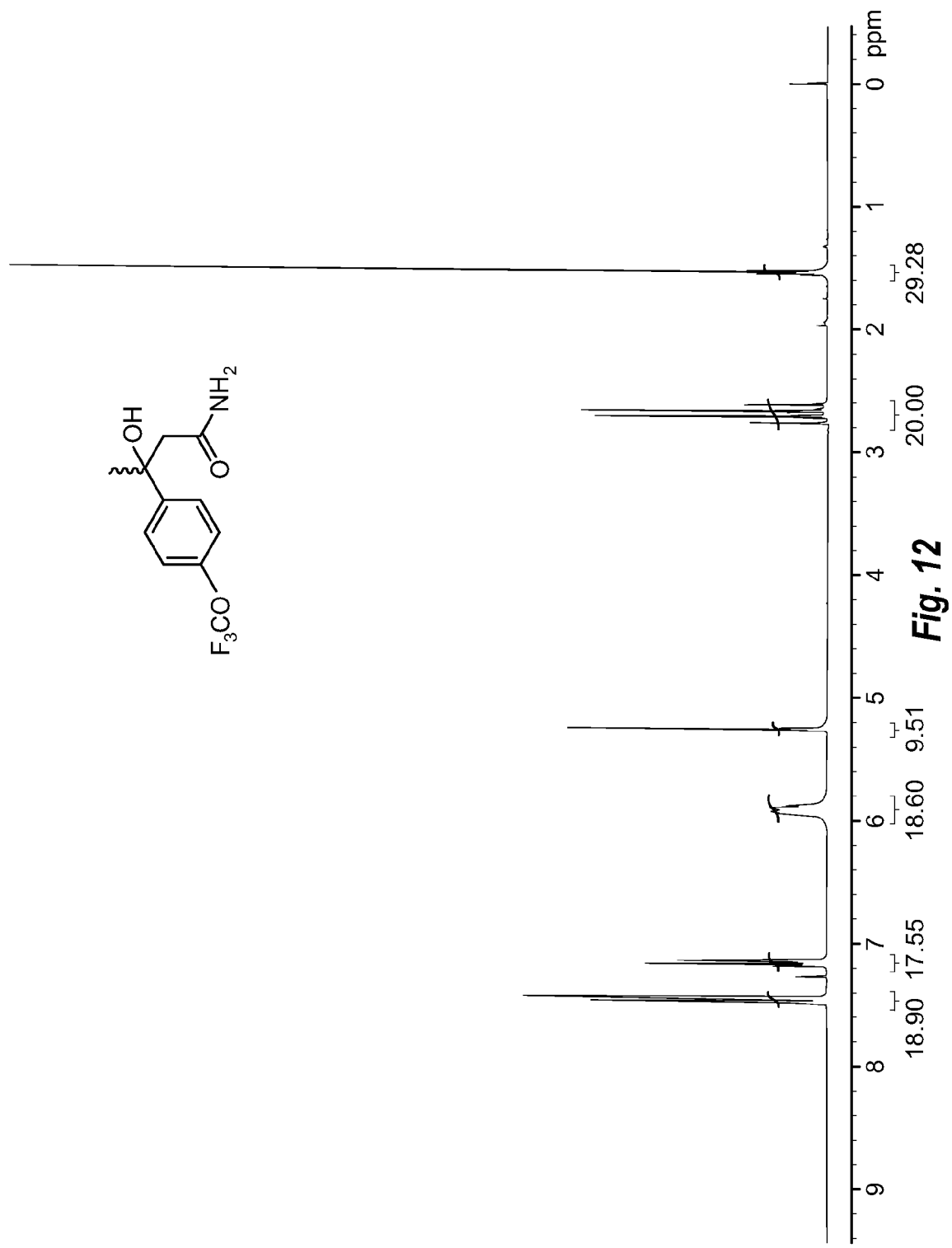
FIG. 12 shows a $^1$H-NMR spectrum of compound CC.
Figure 13:
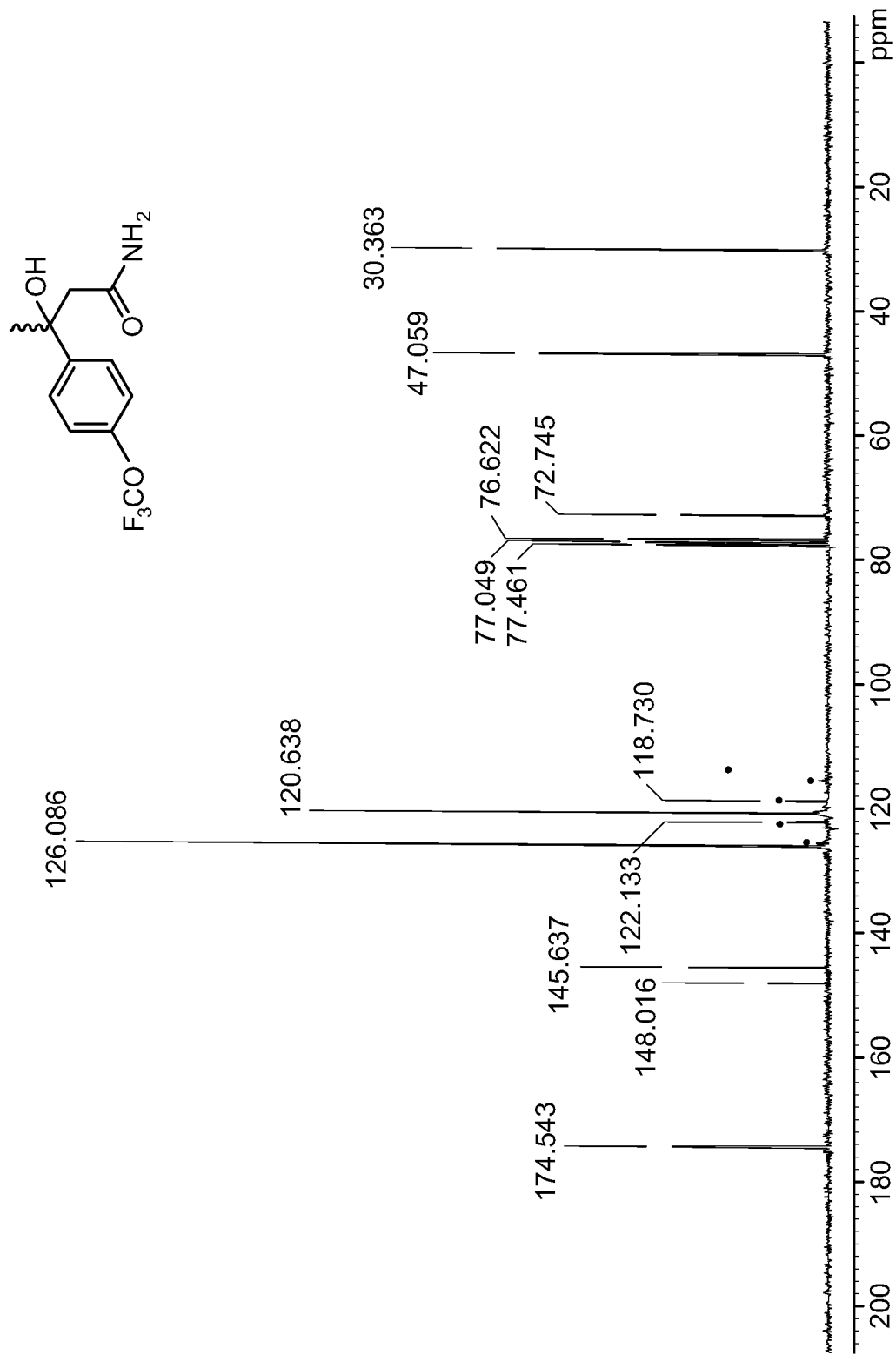
FIG. 13 shows a $^{13}$C-NMR spectrum of compound CC.

In a 250 mL three necked flask equipped with a stirring bar, an internal thermocouple and a rubber septum was placed BTSA (49 mmol, 12 mL) in 90 mL THF at −73° C. A hexanes solution of n-BuLi (1.6 M, 49 mmol, 30.6 mL) was added dropwise (strongly exothermic) through a syringe over 25-30 min while maintaining the temperature below −69° C. The mixture was stirred for 15-20 min then a THF (80 mL) solution of the ketone (54 mmol, 11.02 g) was added over 25-30 min while maintaining the temperature below −70° C. After stirring 90 min at around −73° C. the cooling bath was removed and added 1N aq.HCl until pH 5-6. The cold solution was diluted with 400 mL EtOAc and transferred into a separating funnel. The organic layer was separated and washed with water, brine then dried (MgSO$_4$). After concentration the crude solid was suspended in 150 mL hexanes and warmed up to 45° C. while spinning on a rotary evaporator for ~10 min. The solid was filtered and further washed with 50 mL hexanes then dried to a constant weight. Yield: 10.2 g (79%). $^1$H-NMR spectroscopy (FIGS. 12 and 13) of each final product gave signals consistent with its structure and indicated greater than 98% purity.

Example 62

Synthesis of Compounds CD and CE

Figure 14:
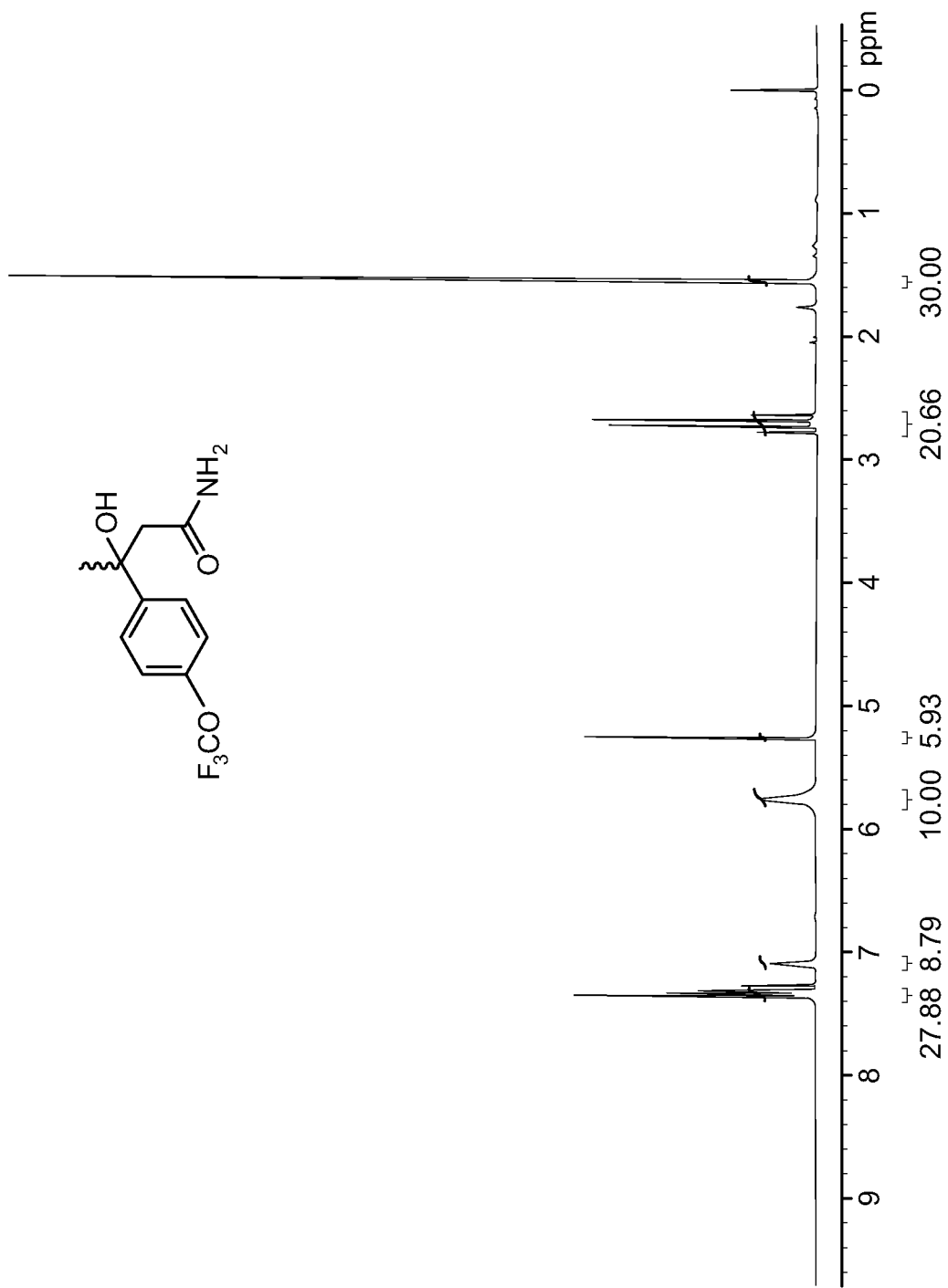
FIGS. 14 and 15 show additional $^1$H-NMR spectra of compound CC.
Figure 15:
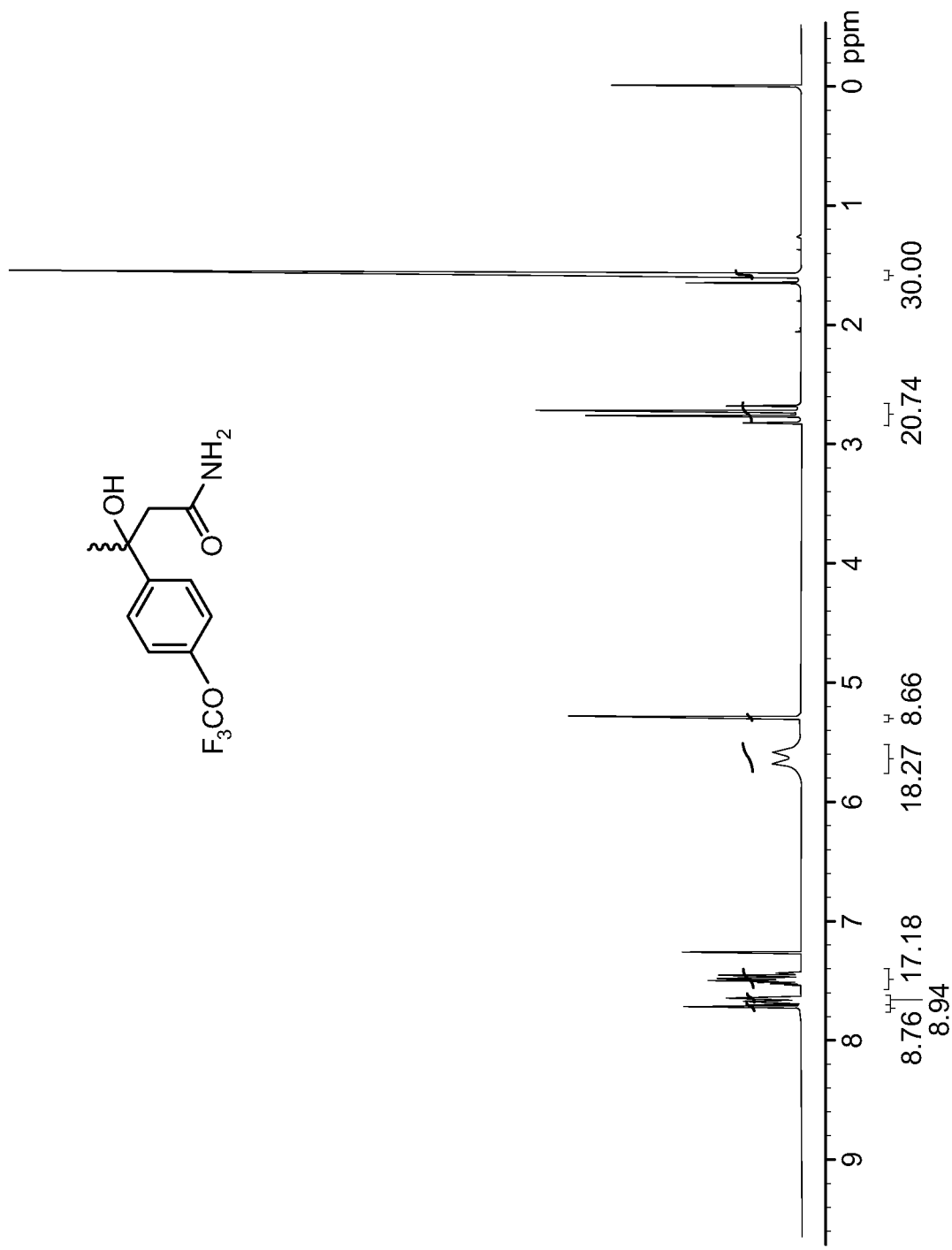

Compounds CD and CE were synthesized using the corresponding 3'-substituted acetophenones via the method used for the preparation of Compound CC in Example 61, above. $^1$H-NMR spectroscopy (FIGS. 14 and 15) of each final product gave signals consistent with its structure and indicated greater than 98% purity.

Example 63

Demonstration of Biological Activity in Rodent Anticonvulsant Models of Epilepsy The anticonvulsant activities of various compounds of the invention were demonstrated in vivo in various rodent (mouse and rat) models of epilepsy. The animal testing was performed as described in White et al., "Discovery and preclinical development of antiepileptic drugs," in *Antiepileptic Drugs*, 5$^{th}$ ed., Levy et al. (Eds.), Lippincott Williams and Wilkins, Philadelphia, Pa., 2002 (968 pp.), pp. 36-48, and references contained therein, which are hereby incorporated herein in their entirety. The results for compounds A, G, H, I, and F are summarized below in Tables 5 and 6.

TABLE 5

ANTICONVULSANT PROFILES OF COMPOUNDS OF THE PRESENT INVENTION, FOLLOWING I.P. ADMINISTRATION TO MICE
MID$_{50}$ or ED$_{50}$ (mg/kg) and (PI)*

| Compound | MID$_{50}$ | MES$^a$ (PI) | s.c. MET$^b$ (PI) | AGS$^c$ (PI) | 6 Hz (PI) |
|---|---|---|---|---|---|
| A | <100 | <100 | ≤100 | — | >30 (<3.3) |
| G | <100 | <100 | ≤100 | — | — |
| I | <100 | <100 | ≤100 | — | — |
| H | 158.98 | 76.11 (2.1) | 91.36 (1.74) | 22.5 (7.1) | 54.98 (2.9) |
| F | 208.37 | 85.32 (2.4) | 85.47 (2.4) | 41.30 (5) | 80.8 (2.6) |

MID$_{50}$ = median minimal motor impairment dose; ED$_{50}$ = median effective dose;
$^a$Maximal Electroshock Seizure test.
$^b$Subcutaneous Metrazol Seizure threshold.
$^c$Audiogenic Seizure susceptible.
(PI)* = Protective Index = MID$_{50}$/ED$_{50}$.

In addition to the compounds shown in Table 5 above, the following compounds also show activity in the MES test at 100 mg/kg: C, Q-2, Q-3, X, Y, AA, AE, AL, AM, AN, AO, AQ, AS, BD, BE, BG, BJ, BL, BR, BU and BV; and at 300 mg/kg: D, L, N, P, Q-1, AP, AR, AW, BF, BM, BN, and BS.

In addition to the compounds shown in Table 5 above, the following compound also shows activity in the s.c. MET test at 100 mg/kg: Y; and at 300 mg/kg: D, J, L, Q-1, Q-2, X, AA, AO, AP, AQ, AR, BC, BD, BF, BH, BI, and BM.

In addition to the compounds shown in Table 5 above, the following compounds also show activity in the 6 Hz (minimal clonic seizure) model at 100 mg/kg: Y, Q-1, Q-2, AA, AN, AX, AY, BB, BL, BK, and CA; at 200 mg/kg: AE and AW; and at 300 mg/kg: Q.

In the corneal kindled mouse model, compound F has an ED$_{50}$=60.6 mg/kg, and brought the seizure score down to zero at 100 mg/kg, indicating that it knocked out the epileptic focus.

Two tertiary amide compounds showed evidence of CNS-stimulating activity. Specifically, mice administered compound BE at 300 mg/kg i.p. exhibited tremors 30 minutes after injection, and those given compound BH exhibited vocalization and hyperactivity on injection lasting for 5-6 minutes. In addition, two further tertiary amide compounds, BJ and BT, produced diarrhea in the mice 30 minutes after i.p. injection of 100 mg/kg of each.

TABLE 6

MINIMAL MOTOR IMPAIRMENT AND PROFILES OF ANTICONVULSANT ACTIVITY OF COMPOUNDS OF THE PRESENT INVENTION IN RATS (ADMINISTERED P.O.)

| Compound | MID$_{50}$ (mg/kg) | MES (mg/kg) (PI) | s.c. MET (mg/kg) (PI) |
|---|---|---|---|
| A | 244.90 | 28.80 (8.5) | 45.00 (5.4) |
| H | >500 | 56.73 (>9) | 88.09 (>5.7) |
| F | >500 (none observed) | 26.39 (>19) | >250 |

In addition to the compounds shown in Table 6 above, the following compounds also show activity in the MES test at 30 mg/kg: G, I, P, X, AA, AM, AQ, AS, BE, BG, BJ, and BV.

In addition to the compounds shown in Table 6 above, compound G also shows activity in the s.c. MET test at 30 mg/kg.

In the Preliminary Hippocampal Kindling Screening in rats (i.p.), compounds A and H brought the seizure score down to zero at 65 and 100 mg/kg, respectively, indicating that they knocked out the epileptic focus. In the Hippocampal Kindled Rats model, compounds A, F and H showed activity with ED$_{50}$ values of 26, 29, and 61 mg/kg, respectively, and compound G showed activity by significantly lowering the seizure score at 100 mg/kg.

Example 64

Demonstration of Biological Activity in Rat Anticonvulsant Models of Status Epilepticus The anticonvulsant activities of various compounds of the present invention were also demonstrated in vivo in two rat models of status epilepticus. The animal testing was performed using the protocols developed in the Anticonvulsant Screening Program (ASP) at the National Institute of Neurological Disorders and Stroke (NINDS), National Institutes of Health (NIH). The results are summarized below in Table 7.

TABLE 7

Compound Activities in Status Epilepticus Models
(ASP/NINDS/NIH data)
(Pilocarpine-induced Status Epilepticus in Rats)

| Test Compound | Prevention | | Intervention @ 30 min | |
|---|---|---|---|---|
| | Protection | Dose (mg/kg) | Protection | Dose (mg/kg) |
| A* | 86% | 65 | 57% | 120 |
| B | 43% | 300 | nt | — |
| D | 100% | 200 | 75% | 400 |
| O | 50% | 450 | 0% | Inactive |
| L | 100% | 450 | 29% | 600 |
| M | 100% | 600 | 0% | Inactive |
| K | 50% | 300 | 38% | 600 |
| I* | 86% | 65 | 100% | 130 |
| H* | 86% | 200 | 97% | 176 |
| G* | 100% | 200 | 88% | 200 |
| F* | 14% | 65 | nt | — |
| J | 75% | 600 | 38% | 600 |
| P* | 100% | 450 | nt | — |
| Q-3* | 100% | 200 | nt | — |
| AW* | 75% | 450 | 25% | 200 |
| AP | 75% | 450 | 75% | 600 |
| AB | 100% | 450 | nt | — |
| AL* | 100% | 200 | nt | — |
| AM* | 100% | 200 | 38% | 400 |
| AQ | 86% | 65 | nt | — |
| AV | 25% | 600 | nt | — |
| AY* | 38% | 600 | nt | — |
| BU* | 100% | 65 | 50% | 127 |
| AS | 100% | 200 | nt | — |
| BF* | 88% | 200 | nt | — |
| Y | 88% | 65 | nt | — |
| AO* | 86% | 65 | 50% | 97 |
| BX | 100% | 100 | 50% | 155 |
| BZ | 100% | 200 | nt | — |
| CA* | 100% | 600 | nt | — |
| CB* | 100% | 200 | nt | — |
| CC | 100% | 200 | nt | — |

*Weight gain or weight maintenance in rats.

Example 65

Demonstration of Lack of Toxicity in In Vitro (LDH and Cell Proliferation) Assays Compounds A, I, H, and F were tested by Stem Cell Innovations, Inc. (Houston, Tex.) in their ACTIVTox® Human Liver Cell-based assays (using C3A hepatocyte cells). Specifically, the compounds were tested in the LDH release assay, which determines the release of Lactate DeHydrogenase (an indicator of cell death) at various concentrations of test compound.

A concentration of 100 µM of test compound is a much higher level of exposure to liver cells than would ever be expected under physiological conditions. Therefore, using 100 µM as a standard test concentration (for comparative purposes), the ratio of the absorbance (which measures the level of LDH release) resulting from the presence of the test compound versus the negative control is a value known as the "average (or mean) fold control" (Average Fold Control=Average of Absorbance/Average of Negative Control). An average fold control value below 1.75 indicates that the test compound has no cyto- or hepatotoxic activity in the LDH release assay.

The ACTIVTox data (see Table 8, below) show that the compounds A, I, H and F are not cyto- or hepatotoxic at physiologically relevant concentrations (i.e., <100 µM).

TABLE 8

Cytotoxic and hepatotoxic data (mean fold control
at 100 µM) from the ACTIVTox LDH release assay.

| Test Compound | LDH release, mean fold control (at 100 µM) |
|---|---|
| A | 1.05 |
| I | 1.03 |
| H | 1.32 |
| F | 1.47 |

Compounds A and I were also tested in the ACTIVTox Cell Proliferation Assay and were found to be non-toxic to proliferating cells at a concentration of 100 µM, with mean fold control values of 1.15 and 1.25, respectively.

Example 66

Demonstration of Analgesic Activity in the Mouse Formalin Pain Model and the Sciatic Nerve Ligation Model in Rats Compounds of the present invention are active in the mouse formalin pain model, significantly decreasing the animals' pain response in both the acute and inflammatory phases. Furthermore, such compounds have also been shown to exhibit significant analgesic effects against both:
  a) inflammatory (formalin-induced) pain, and
  b) neuropathic (sciatic nerve-ligation) pain.

Classical animal pain models, such as the formalin test (chemically induced nociception) and the sciatic nerve ligation model of chronic pain and painful neuropathy (including allodynia, hyperalgesia, and spontaneous pain) are described in Ramabadran, K. and M. Bansinath, "Evaluation of analgesic actions of morphine in various pain models in experimental animals," in L. D. Kapoor (Ed.), *Opium Poppy: Botany, Chemistry, and Pharmacology*, Haworth Press: New York, 1997; pp. 255-298.

The racemic compound H is active in the formalin pain model (mouse i.p.), significantly decreasing the animals' pain response in both the acute (to 63% of the control) and inflammatory (also to 63% of the control) phases at 76 mg/kg i.p. (at 0.5 hours). In the sciatic nerve-ligation model in rats, compound H also significantly increases the allodynic threshold to 455% of the control at a dose of 62 mg/kg at 0.5 hours.

One of the active enantiomers of H, i.e., BX, is also active in the mouse formalin pain model, significantly decreasing the animals' pain response in both the acute (to 84% of the control) and inflammatory (to 41% of the control) phases at 76 mg/kg i.p. (at 0.5 hours).

The other active enantiomer of H, i.e., BY, is also active in the mouse formalin pain model, significantly decreasing the animals' pain response in both the acute (to 53% of the control) and inflammatory (to 24% of the control) phases at 76 mg/kg i.p. (at 0.5 hours). It thus appears that BY is the more potent and effective analgesic enantiomer of H, although both of the enantiomers exhibit significant activity in the mouse formalin pain model.

At a dose of 100 mg/kg, compound G also exhibited a significant analgesic effect in the sciatic nerve-ligation model in rats, shown by a statistically significant increase of the allodynic threshold (to 275% of the control), especially at 1 hour post-administration. [The response (threshold for foot withdrawal) was measured in grams.] The allodynic threshold was observed to decrease in a time-dependent manner, with the analgesic effect (i.e., an increased allodynic threshold) still evident in the rats at 2 hours (219% of the control) and 4 hours (175% of the control) post-administration.

Example 67

Mechanism-of-Action Studies with Compound H

The mechanisms of action of many currently marketed anticonvulsant drugs are not fully understood. Although numerous molecular targets exist wherein anticonvulsants may exert an effect, the final common pathway appears to be through modulation of voltage-gated and/or neurotransmitter-gated ion channels. Thus, the common link among the various proposed mechanisms involves the ability of an anticonvulsant to modulate ion channel function. Presently, a number of prototype anticonvulsants are thought to exert their action (at least in part) by reducing sustained, high-frequency repetitive firing of action potentials by modulating voltage-dependent sodium (Na+) channels. The effect of promising candidate substances on voltage-gated Na+ channels can be assessed using state-of-the-art electrophysiological techniques. Mechanism-of-action studies for compound H (at 100 µM and lower concentrations) indicate the following:
  a) inactive at kainate (KA; at 100 µM, 99±1% of control at a holding potential of −70 mV) and GABA receptors (at 100 µM, 108±3% of control at a holding potential of −70 mV).
  b) very weak activity at sodium channels as measured by lack of inhibition of sodium currents (at 100 µM, 91±1% and 98±1% of controls at holding potentials of −60 and −90 mV, respectively).
  c) weak activity at NMDA receptors (at 100 µM [+glycine (1 µM)], enhancement of NMDA current to 119±7% of control at a holding potential of −70 mV).
  d) a novel molecular target (not yet identified) is implicated.

In connection with the weak antagonist activity seen at NMDA receptors, it is noteworthy that no evidence of psychotomimetic and/or stereotypical behaviors has been observed in any of the in vivo animal studies that were carried out with the compounds of the present invention, even when high doses were administered [see Kohl, B. K. and G. Dannhardt, "The NMDA receptor complex: A promising target for novel antiepileptic strategies," Curr. Med. Chem. 8 (11 Sep. 2001): 1275-1289].

The effects of compound H (at a concentration of 100 µM) on sodium currents were evaluated in electrophysiological studies at holding potentials of −60 and −90 mV (using 8 cells). The observed inhibition of sodium currents by compound H (expressed as % of control ±S.E.M.) was statistically significant, although the overall effect was actually very weak (i.e., 91±1% and 98±1%, respectively). By way of comparison, the % of control inhibited for typical sodium-channel-blocking drugs such as phenyloin or lamotrigine is about 50%. Since, in addition, compound H does not profile like these marketed drugs in the resistant seizure models, it appears that the compound of the invention (H) exerts its unique profile by a combination of mechanisms. This unique profile (including protective activity against both convulsive and non-convulsive seizures induced in the resistant status epilepticus models) further implicates a novel mechanism of action exerted by a unique target (which has not yet been identified) that explains its activity. With regard to possible non-traditional analgesic mechanisms involved in mitigating and relieving chronic neuropathic pain, it is noteworthy that the relatively new analgesic agent, tramadol (Nucynta®), acts in part as a weak, but fast-acting serotonin and norepinephrine reuptake inhibitor (traditionally antidepressant mechanisms), while several opioids (such as methadone) have NMDA antagonist activity in addition to their g-opioid agonist properties. Other CNS-active compounds which have shown analgesic properties as well as NMDA antagonist activity include the psychotropic agent ketamine, the centrally active potassium-channel opener, flupirtine (with weak NMDA antagonist properties), dextromethorphan, ketobemidone, and possibly piritramide. Furthermore, carbamazepine and oxcarbazepine act principally on sodium channels, tricyclic antidepressants may also work on sodium channels in peripheral nerves, and gabapentin and pregabalin work by blocking specific calcium channels on neurons.

Example 68

Demonstration of Activity in the Lamotrigine-Resistant Amygdala-Kindled Rat Model of Partial Epilepsy and the Gender Neutral Test Resistance to Lamotrigine can be induced in rats by treating them with the drug during the kindling acquisition phase (i.e., during kindling development in the epileptogenesis phase). Subsequently, the fully kindled Lamotrigine-refractory rats (i.e., now fully manifesting seizures) are also resistant (cross-tolerant) to carbamazepine, phenyloin, and topiramate, but not to valproate (or diazepam or the clinical Phase III drug candidate, retigabine).

The Lamotrigine-resistant amygdala-kindled rat model (LRM) may thus serve as an early model of drug-resistant (i.e., pharmacoresistant, refractory) epilepsy to identify novel AEDs for further evaluation in more extensive model systems, including the phenyloin-resistant kindled rat [see Engel, J., T. A. Pedley, J. Aicardi, and M. A. Dichter (Eds.), Epilepsy: A Comprehensive Textbook, Volume 1, $2^{nd}$ ed., Lippincott, Williams and Wilkins, 2007, p. 1477].

The LRM thus serves to identify novel broad-spectrum AEDs which may be effective in the treatment of drug-resistant epilepsies. Up to 35% of epilepsy patients continue to suffer from uncontrolled seizures because of their drug-resistant epilepsies. In such cases, the patients do not respond to standard AEDs such as lamotrigine (Lamictal®), carbamazepine (Tegretol®), phenyloin (Dilantin®), and topiramate (Topamax®).

The only currently marketed AED which is effective in this animal model (LRM) is the very broad-spectrum agent, valproate. Since compound H is also active in the LRM, it thus shares valproate's wide-ranging anticonvulsant and antiepileptic activities.

The Gender Neutral test demonstrates the differences between the genders in the way that they respond to AEDs. In this test, compound H was found to be equally efficacious in both genders, unlike, e.g., phenyloin (Dilantin®) which is significantly less effective in male kindled rats than it is in female kindled rats [see Ebert, U., C. Rundfeldt, and W. Loscher, "Sex differences in the anticonvulsant efficacy of phenyloin in amygdala-kindled rats," Brain Res. 638(1-2; 28 February): 45-52 (1994)].

Example 69

In Vitro Human CYP-450 Studies

Out of eight human CYP-450 enzymes tested, compound H has either no or only a remote possibility of inhibiting four of the tested enzymes (3A4, 2E1, 2B6 and 1A2). On the other hand, it is an inhibitor for 2C19, 2D6, 2A6 and 2C9. The Ki values range from 29 to 174 µM.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references recited herein are incorporated herein in their entirety by specific reference.

What is claimed is:

1. A pharmaceutical composition, comprising a therapeutically effective amount of at least one compound of Formula BX or Formula BY admixed with at least one of a pharmaceutically acceptable carrier or an excipient

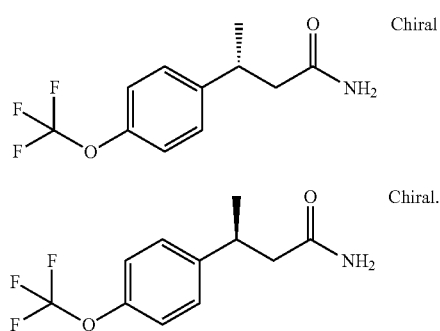

2. The pharmaceutical composition as in claim 1, wherein the therapeutically effective amount of at least one of Formula BX or Formula BY ranges from 22.5 mg/kg to 200 mg/kg.

3. A pharmaceutical composition comprising a therapeutically effective amount of a compound of Formula BX admixed with at least one of a pharmaceutically acceptable carrier or an excipient

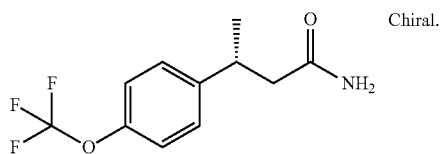

4. A composition for treating or preventing acute or chronic pain comprising an analgesic effective amount at least one of

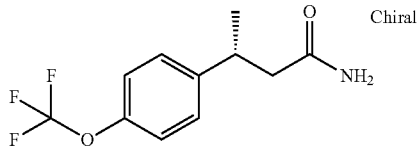

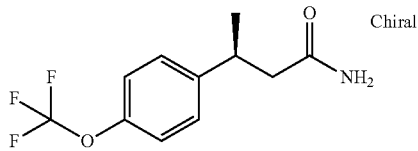

admixed with pharmaceutical acceptable carrier or excipient.

5. A composition for treating or preventing convulsion or seizure comprising an anticonvulsant effective amount at least one of

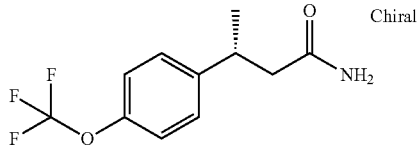

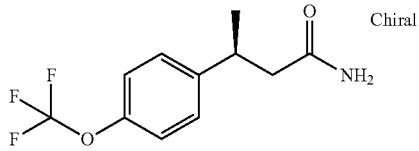

admixed with pharmaceutical acceptable carrier or excipient.

* * * * *